US008771816B2

(12) United States Patent
DesLauriers et al.

(10) Patent No.: US 8,771,816 B2
(45) Date of Patent: Jul. 8, 2014

(54) CONTROLLING MELT FRACTURE IN BIMODAL RESIN PIPE

(71) Applicant: Chevron Phillips Chemical Company LP, The Woodlands, TX (US)

(72) Inventors: Paul J. DesLauriers, Owasso, OK (US); Yongwoo Inn, Bartlesville, OK (US); Qing Yang, Bartlesville, OK (US); Ashish M. Sukhadia, Bartlesville, OK (US); David C. Rohlfing, Bloomington, IN (US); Pamela L. Maeger, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 9 days.

(21) Appl. No.: 13/660,777

(22) Filed: Oct. 25, 2012

(65) Prior Publication Data
US 2013/0323450 A1  Dec. 5, 2013

Related U.S. Application Data

(60) Provisional application No. 61/654,018, filed on May 31, 2012.

(51) Int. Cl.
B29C 47/00 (2006.01)
C08F 110/02 (2006.01)
F16L 9/00 (2006.01)
F16L 9/12 (2006.01)

(52) U.S. Cl.
CPC ............. C08F 110/02 (2013.01); F16L 9/00 (2013.01); F16L 9/12 (2013.01)
USPC ........................................ 428/36.9; 264/40.1

(58) Field of Classification Search
CPC ............. C08F 110/02; F16L 9/00; F16L 9/12

USPC ........................................ 428/36.9; 264/40.1
See application file for complete search history.

(56) References Cited

U.S. PATENT DOCUMENTS 3,248,179 A  4/1966  Norwood
3,920,782 A  11/1975  Cogswell (Continued)

OTHER PUBLICATIONS

Aaltonen, Päivi, et al., "Synthesis of functional polyethylenes with soluble metallocene/methylaluminoxane catalyst," Macromolecules, 1995, pp. 5353-5357, vol. 28, No. 15, American Chemical Society.

(Continued)

Primary Examiner — N. Edwards
(74) Attorney, Agent, or Firm — Rodney B. Carroll; Cheryl L. Huseman; Conley Rose, P.C.

(57) ABSTRACT

A method of preparing a medium-density polyethylene pipe comprising melting a multimodal metallocene-catalyzed polyethylene resin to form a molten polyethylene, wherein the multimodal metallocene-catalyzed polyethylene resin has a density of from about 0.925 g/ml to about 0.942 g/ml, a magnitude of slip-stick greater than about 300 psi, a stress for smooth to matte transition of greater than about 90 kPa of stress, and a shear rate for smooth to matte transition greater than about $10\,\text{s}^{-1}$, wherein the magnitude of slip-stick, stress for smooth to matte transition, and shear rate for smooth to matte transition are determined by a capillary rheology test; and forming the molten polyethylene resin into pipe. A pipe prepared from a multimodal metallocene-catalyzed polyethylene resin having a density of from about 0.925 g/ml to about 0.942 g/ml, a magnitude of slip-stick greater than about 300 psi; a stress for smooth to matte transition of greater than about 90 kPa, and a shear rate for smooth to matte transition greater than about $10\,\text{s}^{-1}$, wherein the magnitude of slip-stick, stress for smooth to matte transition, and shear rate for smooth to matte transition are determined by a capillary rheology test.

20 Claims, 7 Drawing Sheets

(56) References Cited

U.S. PATENT DOCUMENTS

| | | | |
|---|---|---|---|
| 4,187,269 A | 2/1980 | Hutchinson et al. | |
| 4,267,146 A | 5/1981 | Kurtz et al. | |
| 4,282,177 A | 8/1981 | Kurtz et al. | |
| 4,348,349 A | 9/1982 | Kurtz | |
| 4,360,494 A | 11/1982 | Kurtz | |
| 4,501,885 A | 2/1985 | Sherk et al. | |
| 4,522,776 A | 6/1985 | Ramamurthy | |
| 4,552,712 A | 11/1985 | Ramamurthy | |
| 4,554,120 A | 11/1985 | Ramamurthy | |
| 4,588,790 A | 5/1986 | Jenkins, III et al. | |
| 4,713,205 A | 12/1987 | Su | |
| 4,948,543 A | 8/1990 | Pawlowski et al. | |
| 5,204,032 A | 4/1993 | Ramamurthy et al. | |
| 5,210,142 A | 5/1993 | Kale et al. | |
| 5,320,798 A | 6/1994 | Chambon et al. | |
| 5,352,749 A | 10/1994 | DeChellis et al. | |
| 5,436,304 A | 7/1995 | Griffin et al. | |
| 5,455,314 A | 10/1995 | Burns et al. | |
| 5,459,187 A | 10/1995 | Taylor et al. | |
| 5,550,193 A | 8/1996 | Chiu et al. | |
| 5,565,175 A | 10/1996 | Hottovy et al. | |
| 5,575,979 A | 11/1996 | Hanson | |
| 5,854,352 A | 12/1998 | Chisholm et al. | |
| 6,100,320 A | 8/2000 | Cobb et al. | |
| 6,218,472 B1* | 4/2001 | Debras et al. | 525/191 |
| 6,239,235 B1 | 5/2001 | Hottovy et al. | |
| 6,262,191 B1 | 7/2001 | Hottovy et al. | |
| 6,833,415 B2 | 12/2004 | Kendrick et al. | |
| 7,056,744 B2 | 6/2006 | DesLauriers et al. | |
| 7,226,886 B2 | 6/2007 | Jayaratne et al. | |
| 7,312,283 B2 | 12/2007 | Martin et al. | |
| 7,632,086 B2 | 12/2009 | Veariel et al. | |
| 8,048,679 B2 | 11/2011 | DesLauriers et al. | |
| 2004/0198911 A1 | 10/2004 | Van Dun et al. | |
| 2010/0304051 A1* | 12/2010 | Henschke et al. | 428/17 |
| 2011/0172322 A1* | 7/2011 | Michel et al. | 521/144 |
| 2013/0232450 A1* | 9/2013 | Dearman et al. | 715/835 |
| 2013/0319131 A1* | 12/2013 | Inn et al. | 73/841 |
| 2013/0325363 A1* | 12/2013 | DesLauriers et al. | 702/27 |

OTHER PUBLICATIONS

Ansari, Mahmoud, et al., "Rheology of Ziegler-Natta and metallocene high-density polyethylenes: broad molecular weight distribution effects," Rheol Acta, 2011, pp. 17-27, vol. 50, Springer-Verlag.

Blyler, Jr., L. L., et al., "Capillary flow instability of ethylene polymer melts," Polymer Engineering and Science, Jul. 1970, pp. 193-203, vol. 10, No. 4.

Brochard, F., et al., "Shear-dependent slippage at a polymer/solid interface," Langmuir, 1992, pp. 3033-3037, vol. 8, No. 12, American Chemical Society.

Busse, W. F., "Two decades of high-polymer physics: A survey and forecast," Physics Today, Sep. 1964, pp. 32-41 plus cover page, American Institute of Physics.

Cogswell, F.N., "Stretching flow instabilities at the exits of extrusion dies," Journal of Non-Newtonian Fluid Mechanics, 1977, pp. 37-47, vol. 2, Elsevier Scientific Publishing Company, Amsterdam.

Dealy, John, et al., "Structure and rheology of molten polymers," 2006, 1 page, Hanser Verlag.

Denn, Morton M., "Extrusion instabilities and wall slip," Annu. Rev. Fluid Mech., 2001, pp. 265-287, vol. 33, Annual Reviews.

El Kissi, N., et al., "Sharkskin and cracking of polymer melt extrudates," J. Non-Newtonian Fluid Mech., 1997, pp. 271-290, vol. 68, Elsevier Science B.V.

Filing receipt and specification for provisional patent application entitled "Controlling melt fracture in bimodal resin pipe," by Yongwoo Inn, et al., filed May 31, 2012 as U.S. Appl. No. 61/654,018.

Filing receipt and specification for patent application entitled "Controlling melt fracture in bimodal resin pipe," by Yongwoo Inn, et al., filed Oct. 25, 2012 as U.S. Appl. No. 13/660,747.

Filing receipt and specification for patent application entitled "Controlling melt fracture in bimodal resin pipe," by Paul J. DesLauriers, et al., filed Oct. 25, 2012 as U.S. Appl. No. 13/660,750.

Filing receipt and specification for International application entitled "Controlling melt fracture in bimodal resin pipe," filed May 29, 2013 as International Application No. PCT/US2013/043154.

Fodor, Jeffrey, et al., "On the detection of flow-induced fractionation in melts of homopolymers by normal-mode microdielectrometry," Macromolecules, 1992, pp. 3511-3520, vol. 25, No. 13, American Chemical Society.

Honerkamp, J., et al., "Determination of the relaxation spectrum by a regularization method," Macromolecules, 1989, pp. 4372-4377, vol. 22, No. 11, American Chemical Society.

Hubert, L., et al., "Physical and mechanical properties of polyethylene for pipes in relation to molecular architecture. II. Short-term creep of isotropic and drawn materials," Journal of Applied Polymer Science, 2002, pp. 2308-2317, vol. 84, Wiley Periodicals, Inc.

Inn, Yong W., et al., "Application of creep test to obtain the linear viscoelastic properties at low frequency range for polyethylene melts," Applied Rheology, 2012, pp. 15260-1 to 15260-8, vol. 22, Issue 1.

Inn, Yong Woo, "Visual oberservation of development of sharkskin melt fracture in poybutadiene extrusion," Rheol Acta, 1998, pp. 573-582, vol. 37, No. 6, Steinkopff Verlag.

Joseph, Daniel D., et al., "Letter to the editor: Steep wave fronts on extrudates of polymer melts and solutions," J. Rheol., Mar./Apr. 1996, pp. 317-320, vol. 40, No. 2, The Society of Rheology, Inc.

Joseph, Daniel D., "Steep wave fronts on extrudates of polymer melts and solutions: lubrication layers and boundary lubrication," J. Non-Newtonian Fluid Mech., 1997, pp. 187-203, vol. 70, Elsevier Science B.V.

Koopmans, Rudy, et al., "Polymer melt fracture," 2010, 3 pages of cover, publishing information, and description, CRC Press.

Laurent, E., "Comprehensive evaluation of the long-term mechanical properties of PE100 resins meeting the requirements of modern installation techniques," Oct. 2001, pp. 63-73 plus cover page, Woodhead Publishing Limited.

Migler, K. B., et al., "Extensional deformation, cohesive failure, and boundary conditions during sharkskin melt fracture," J. Rheol., Mar./Apr. 2002, pp. 383-400, vol. 46, No. 2, The Society of Rheology, Inc.

Muñoz-Escalona, A., et al., "Rheology of metallocene-catalyzed monomodal and bimodal polyethylenes," Polymer Engineering and Science, Nov. 1999, pp. 2292-2303, vol. 39, No. 11.

Park, Hee Eon, et al., "Wall slip and spurt flow of polybutadiene," J. Rheol., Sep./Oct. 2008, pp. 1201-1239, vol. 52, No. 5, The Society of Rheology, Inc.

Pomar, Gabriel, et al., "Extrudate distortions in linear low-density polyethylene," J. Non-Newtonian Fluid Mech., 1994, pp. 143-151, vol. 54, Elsevier Science B.V.

Raju, V. R., et al., "Properties of amorphous and crystallizable hydrocarbon polymers. I. Melt rheology of fractions of linear polyethylene," Journal of Polymer Science: Polymer Physics Edition, 1979, pp. 1183-1195, vol. 17, John Wiley & Sons, Inc.

Schreiber, H. P., "Molecular dependence of flow instability in polyethylene," Polymer Letters, 1969, pp. 851-860, vol. 7.

Schreiber, H. P., et al., "Molecular fractionation in capillary flow of polymer fluids," Polymer Letters, 1965, pp. 723-727, vol. 3.

Schreiber, H. P., et al., "Molecular fractionation in the flow of polymeric fluids," Transactions of the Society of Rheology, 1966, pp. 275-297, vol. 10, No. 1.

Shelby, M. David, et al., "Shear field induced diffusion and molecular weight fractionation during polymer processing," Polymer Engineering and Science, Jul. 2004, pp. 1283-1294, vol. 44, No. 7, Society of Plastics Engineers.

Struglinski, Mark J., et al., "Effects of polydispersity on the linear viscoelastic properties of entangled polymers. 1. Experimental observations for binary mixtures of linear polybutadiene," Macromolecules, 1985, pp. 2630-2643, vol. 18, No. 12, American Chemical Society.

Wagner, H. L., et al., "Some effects of molecular weight distribution on the melt rheology of high density polyethylene," SPE Transactions, Jul. 1962, pp. 222-226.

(56) References Cited

OTHER PUBLICATIONS

Wang, Shi-Qing, et al., "Exploring molecular origins of sharkskin, partial slip, and slope change in flow curves of linear low density polyethylene," J. Rheol., Sep./Oct. 1996, pp. 875-898, vol. 40, No. 5, The Society of Rheology, Inc.

Wang, Shi-Qing, et al., "Superfluid-like stick-slip transition in capillary flow of linear polyethylene melts. 1. General features," Macromolecules, 1996, pp. 2627-2632, vol. 29, No. 7, American Chemical Society.

Whitlock, L. Ronald, et al., "Experimental investigation of the concept of molecular migration within sheared polystyrene," Journal of Polymer Science: Part A-2, 1972, pp. 877-886, vol. 10, John Wiley & Sons, Inc.

Yamaguchi, Masayuki, et al., "Relation between molecular structure and flow instability for ethylene/α-olefin copolymers," Polymer, 2002, pp. 5249-5255, vol. 43, Elsevier Science Ltd.

Piau, J.M., et al., Influlence of upstream instabilities and wall slip on melt fracture and sharkskin phenomena during silicones extrusion through orifice dies, Jo. of Non-Newton. Fluid Mech., 1990, pp. 145-180, vol. 34.

Rohlfing, D. C., et al., "Melt-rheological characteristics of metallocene-catalyzed polyethylenes," in Metallocene-based Polyolefins, edited by J. Scheirs, et al., 2000, pp. 419-434, John Wiley & Sons, New York.

Ansari, Mahmoud, et al., "Melt Fracture of Two Broad Molecular Weight Distribution High-Density Polyethylenes," XP055110091, Polymer Engineering and Science, 2012, pp. 795-804, Society of Plastics Engineers.

Ansari, Mahmoud, et al., "Slip effects in HDPE flows," Journal of Non-Newtonian Fluid Mechanics, XP028340589, 2012, pp. 18-29, vol. 167-168, Elsevier B.V.

Foreign communication from a related counterpart application—International Search Report and Written Opinion, PCT/US2013/043154, Apr. 3, 2014, 10 pages.

Hatzikiriakos, Savvas G., "Wall slip of molten polymers," Progress in Polymer Science, XP028448103, 2012, pp. 624-643, vol. 37, Elsevier Ltd.

\* cited by examiner

CONTROLLING MELT FRACTURE IN BIMODAL RESIN PIPE

CROSS-REFERENCE TO RELATED APPLICATIONS

The present application is a non-provisional of and claims priority to U.S. Provisional Application No. 61/654,018, filed on May 31, 2012 and entitled "Controlling Melt Fracture in Bimodal Resin Pipe," which is incorporated by reference herein in its entirety.

TECHNICAL FIELD

The present disclosure relates to polyethylene compositions and pipe made from same, more specifically to multimodal polyethylene compositions having improved processing characteristics.

BACKGROUND

Polymeric pipes have replaced metal pipes in many applications such as high-pressure fluid transportation. Polymeric pipes have several advantages over metal pipes including being of relatively lighter weight, more corrosion resistant, inexpensive, more thermally and electrically insulative, tougher, more durable and more easily shaped during manufacture. Such pipes are exposed to numerous stresses during their lifetime that may result in cracks or breaks that are expensive to repair, especially in situations where the pipe is buried in a structure or underground. As such polymeric pipes may be required to meet industry-defined standards depending on their intended use.

Polymeric material used in the fabrication of pipe has often been optimized to provide a more durable end-use article. One such optimization may involve the use of a multimodal polymer composition as the polymeric material. A challenge to the use of a multimodal polymer composition as the polymeric material in the fabrication of pipe is that these compositions, when melted to form a polymer melt, may display poor processing characteristics such as melt fractures, which are surface irregularities that occur during the extrusion process when the production rate is increased. The poor processing characteristics of these materials may result in a reduced production rate and/or product having undesirable physical properties and/or appearance. Thus there is a need for improved polymeric compositions and methods of making and using same to fabricate polymeric pipe.

SUMMARY

Disclosed herein is a method of preparing a medium-density polyethylene pipe comprising melting a multimodal metallocene-catalyzed polyethylene resin to form a molten polyethylene, wherein the multimodal metallocene-catalyzed polyethylene resin has a density of from about 0.925 g/ml to about 0.942 g/ml, a magnitude of slip-stick greater than about 300 psi, a stress for smooth to matte transition of greater than about 90 kPa, and a shear rate for smooth to matte transition greater than about $10\ s^{-1}$, wherein the magnitude of slip-stick, stress for smooth to matte transition, and shear rate for smooth to matte transition are determined by a capillary rheology test; and forming the molten polyethylene resin into pipe.

Also disclosed herein is a pipe prepared from a multimodal metallocene-catalyzed polyethylene resin having a density of from about 0.925 g/ml to about 0.942 g/ml, a magnitude of slip-stick greater than about 300 psi; a stress for smooth to matte transition of greater than about 90 kPa, and a shear rate for smooth to matte transition greater than about $10\ s^{-1}$, wherein the magnitude of slip-stick, stress for smooth to matte transition, and shear rate for smooth to matte transition are determined by a capillary rheology test.

DETAILED DESCRIPTION

Figure 1A:
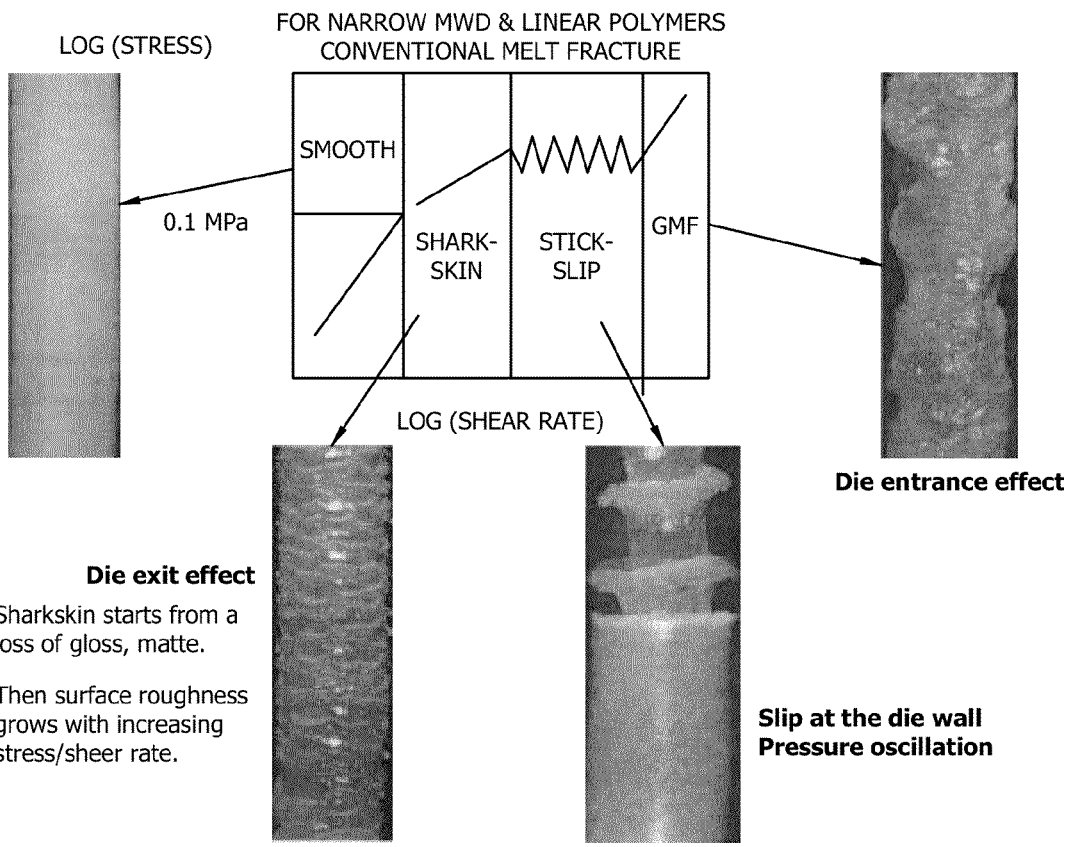
FIG. 1A is a schematic of the melt fracture behavior of a conventional unimodal polyethylene composition.

Disclosed herein are methods of identifying metallocene-catalyzed polyethylene resins having desired processing characteristics. In an embodiment, the method comprises obtaining a plurality of multimodal metallocene-catalyzed polyethylene resins and subjecting these resins to capillary rheometry in order to measure the shear stress as a function of shear rate. The rheometric measurements may be used to identify multimodal metallocene-catalyzed polyethylene resins having one or more desired processing characteristics.

Further disclosed herein are methods of making metallocene-catalyzed polyethylene resins (also termed a PE base resin), general features of said metallocene-catalyzed polyethylene resins, methods for identifying metallocene-catalyzed polyethylene resins having desired processing characteristics, methods of modifying metallocene-catalyzed polyethylene resins to provide desired processing characteristics, and methods of preparing articles from metallocene-catalyzed polyethylene resins having desired processing characteristics.

In an embodiment, a PE base resin of the present disclosure is produced by any olefin polymerization method, using various types of polymerization reactors and catalyst systems. As used herein, a "base resin" refers to a resin that has not undergone a modification to improve processability of the type described herein. In other words, base resin refers to the PE starting material that is accessed and modified according to the present disclosure. Accordingly, the base resin may include virgin PE resin or "fluff" as recovered from a polymerization process and prior to the addition of any additives or modifiers and/or includes PE resin recovered from a polymerization process that has undergone further processing such as pelletization, which may include the addition of a base additive package of the type commonly added to commercial PE resins (e.g., antioxidants, stabilizer). In an embodiment, the PE base resin has not undergone any modification (e.g., inclusion of processing aids.) to improve the melt fracture characteristics of the material. In an embodiment, the PE base resin does not include any polymer processing aids (PPAs) of the type known to those skilled in the art.

In an embodiment, the catalyst system for preparation of the PE base resin comprises at least two metallocene complexes. Herein, the term "metallocene" describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like. The metallocenes may be combined with a solid activator, an aluminum alkyl compound, an olefin monomer, and an olefin comonomer to produce the desired bimodal polyolefin. The activity and the productivity of the catalyst may be relatively high. As used herein, the activity refers to the grams of polymer produced per gram of solid catalyst charged per hour, and the productivity refers to the grams of polymer produced per gram of solid catalyst charged. Examples of such catalyst systems are disclosed in U.S. patent application Ser. No. 11/209,006, filed Aug. 22, 2005 and entitled "Polymerization Catalysts And Process For Producing Bimodal Polymers In A Single Reactor," and U.S. patent application Ser. No. 11/208,077, filed Aug. 19, 2005 and entitled "Polymerization Catalysts and Process for Producing Bimodal Polymers in a Single Reactor," each of which is incorporated herein in its entirety.

As used herein, "polymerization reactor" includes any reactor capable of polymerizing olefin monomers (e.g., ethylene) to produce homopolymers and/or copolymers (e.g., PE homopolymers and/or copolymers). Homopolymers and/or copolymers produced in the reactor may be referred to as resin and/or polymers. The various types of reactors include, but are not limited to those that may be referred to as batch, slurry, gas-phase, solution, high pressure, tubular, autoclave, or other reactor and/or reactors. Gas phase reactors may comprise fluidized bed reactors or staged horizontal reactors. Slurry reactors may comprise vertical and/or horizontal loops. High pressure reactors may comprise autoclave and/or tubular reactors. Reactor types may include batch and/or continuous processes. Continuous processes may use intermittent and/or continuous product discharge or transfer. Processes may also include partial or full direct recycle of un-reacted monomer, un-reacted comonomer, catalyst and/or co-catalysts, diluents, and/or other materials of the polymerization process.

Polymerization reactor systems of the present disclosure may comprise one type of reactor in a system or multiple reactors of the same or different type, operated in any suitable configuration. Production of polymers in multiple reactors may include several stages in at least two separate polymerization reactors interconnected by a transfer system making it possible to transfer the polymers resulting from the first polymerization reactor into the second reactor. Alternatively, polymerization in multiple reactors may include the transfer, either manual or automatic, of polymer from one reactor to subsequent reactor or reactors for additional polymerization. Alternatively, multi-stage or multi-step polymerization may take place in a single reactor, wherein the conditions are changed such that a different polymerization reaction takes place.

The desired polymerization conditions in one of the reactors may be the same as or different from the operating conditions of any other reactors involved in the overall process of producing the polymer of the present disclosure. Multiple reactor systems may include any combination including, but not limited to multiple loop reactors, multiple gas phase reactors, a combination of loop and gas phase reactors, multiple high pressure reactors or a combination of high pressure with loop and/or gas reactors. The multiple reactors may be operated in series or in parallel. In an embodiment, any arrangement and/or any combination of reactors may be employed to produce the polymer of the present disclosure.

According to one embodiment, the polymerization reactor system may comprise at least one loop slurry reactor. Such reactors are commonplace, and may comprise vertical or horizontal loops. Monomer, diluent, catalyst system, and optionally any comonomer may be continuously fed to a loop slurry reactor, where polymerization occurs. Generally, continuous processes may comprise the continuous introduction of a monomer, a catalyst, and/or a diluent into a polymerization reactor and the continuous removal from this reactor of a suspension comprising polymer particles and the diluent. Reactor effluent may be flashed to remove the liquids that comprise the diluent from the solid polymer, monomer and/or comonomer. Various technologies may be used for this separation step including but not limited to, flashing that may include any combination of heat addition and pressure reduction; separation by cyclonic action in either a cyclone or hydrocyclone; separation by centrifugation; or other appropriate method of separation.

Typical slurry polymerization processes (also known as particle-form processes) are disclosed in U.S. Pat. Nos. 3,248,179, 4,501,885, 5,565,175, 5,575,979, 6,239,235, 6,262,191 and 6,833,415, for example; each of which are herein incorporated by reference in their entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another embodiment, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 4,588,790, 5,352,749, and 5,436,304, each of which is incorporated by reference in its entirety herein.

According to still another embodiment, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another embodiment, the polymerization reactor may comprise a solution polymerization reactor wherein the monomer is contacted with the catalyst composition by suitable stirring or other means. A carrier comprising an organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide polymer properties include, but are not limited to temperature, pressure, type and quantity of catalyst or co-catalyst, and the concentrations of various reactants. Polymerization temperature can affect catalyst productivity, polymer molecular weight and molecular weight distribution. Suitable polymerization temperatures may be any temperature below the de-polymerization temperature, according to the Gibbs Free Energy Equation. Typically, this includes from about 60° C. to about 280° C., for example, and/or from about 70° C. to about 110° C., depending upon the type of polymerization reactor and/or polymerization process.

Suitable pressures will also vary according to the reactor and polymerization process. The pressure for liquid phase polymerization in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce polymers with certain physical and mechanical properties. The proposed end-use product that will be formed by the polymer and the method of forming that product may be varied to determine the desired final product properties. Mechanical properties include, but are not limited to tensile strength, flexural modulus, impact resistance, creep, stress relaxation and hardness tests. Physical properties include, but are not limited to density, molecular weight, molecular weight distribution, melting temperature, glass transition temperature, temperature melt of crystallization, density, stereoregularity, crack growth, short chain branching, long chain branching and rheological measurements.

The concentrations of monomer, co-monomer, hydrogen, co-catalyst, modifiers, and electron donors are generally important in producing specific polymer properties. Comonomer may be used to control product density. Hydrogen may be used to control product molecular weight. Co-catalysts may be used to alkylate, scavenge poisons and/or control molecular weight. The concentration of poisons may be minimized, as poisons may impact the reactions and/or otherwise affect polymer product properties. Modifiers may be used to control product properties and electron donors may affect stereoregularity.

In an embodiment, a PE base resin of the type described herein comprises a polymer blend, e.g., a blend of two or more component polymers such as a higher molecular weight (HMW) component and a lower molecular weight (LMW) component. The polymer blend may be of any type compatible with and able to produce a PE base resin of the type described herein. For example, the PE base resin may be a physical or mechanical blend of polymers, alternatively the PE base resin may be a reactor blend of polymers. In an embodiment, a process for the preparation of a PE base resin of the type disclosed herein comprises the preparation of each component of the PE base resin independent of the other components. The process may comprise polymerization of an alpha-olefin monomer in the presence of a catalyst system under a first set of reaction conditions to form a first component of the PE base resin. The process may further comprise polymerization of an alpha-olefin in the presence of a catalyst system under a second set of reaction conditions to form a second component of the PE base resin. The formation of the second component may be carried out in the presence of the first component (e.g., a reactor blend) or in the absence of the first component (and the two components subsequently blended, for example via mechanical blending, co-extrusion, etc.). It is to be understood adjustments of the reaction conditions to which the catalyst system is subjected during polymerization may substantively alter the resultant product. A process for preparation of a PE base resin may further comprise contacting the first and second components utilizing any appropriate methodology (e.g., mechanical mixing). In such an embodiment, the resultant PE base resin comprises a physical blend of the first and second component.

Alternatively, a process for the preparation of a PE base resin of the type disclosed herein comprises polymerization of an alpha-olefin monomer in the presence of at least two different catalytic materials or catalysts, for example a catalyst system comprising at least two transition metal complexes. For example, the catalyst system may comprise a first and a second transition metal complex wherein the first and second transition metal complexes are different. In an embodiment, the catalyst system comprises at least two metallocene complexes and results in the simultaneous formation of the two components of the PE base resin when both catalysts are employed in a single reactor. In the alternative, a first catalyst system comprising a first metallocene complex that may be associated with a first reactor. Alpha-olefin monomer may be contacted with the first catalyst system and reactor and conditions adjusted such that polymerization of the alpha-olefin monomer results and a first component of the PE base resin is produced. The first component may then be contacted with a second catalyst system and alpha-olefin monomer under conditions to result in the polymerization of the alpha-olefin monomer and formation of the second component of the PE base resin. In such an embodiment, the components of the PE base resin are produced sequentially. In the aforementioned embodiments employing at least two metallocene complexes, the PE base resin formed may be described as a reactor blend of the two components.

In an embodiment, the PE base resin comprises a multimodal PE resin. Herein, the "modality" of a polymer resin refers to the form of its molecular weight distribution curve, i.e., the appearance of the graph of the polymer weight fraction as a function of its molecular weight. The polymer weight fraction refers to the weight fraction of molecules of a given size. A polymer having a molecular weight distribution curve showing a single peak may be referred to as a unimodal polymer, a polymer having curve showing two distinct peaks may be referred to as bimodal polymer, a polymer having a curve showing three distinct peaks may be referred to as trimodal polymer, etc. Polymers having molecular weight distribution curves showing more than one peak may be collectively referred to as multimodal polymers or resins. Unless otherwise indicated herein, references to a PE base resin is understood to include a multimodal PE base resin, including but not limited to a resin having a HMW component and a LMW component that is produced from a catalyst system comprising at least two metallocene complexes (e.g., a dual-metallocene catalyst). In an embodiment, the PE base resin is a metallocene-catalyzed, multimodal (e.g., bimodal) polyethylene copolymer with 1-hexene. In an embodiment, the PE base resin is a dual-metallocene-catalyzed, multimodal (e.g., bimodal) polyethylene copolymer. Examples of suitable comonomers include without limitation unsaturated hydrocarbons having from 3 to 20 carbon atoms such as propylene, 1-butene, 1-pentene, 1-hexene, 3-methyl-1-butene, 4-methyl-1-pentene, 1-heptene, 1-octene, 1-nonene, 1-decene, and mixtures thereof. In an aspect, the comonomer is 1-hexene.

A polymer resin may have two or more components that may be distinguishable from one another, for example based upon their individual composition and/or molecular weight distribution. A molecular weight distribution curve may be prepared for each individual component of the polymer resin. For example, the molecular weight distribution curve for the individual components of the polymer resin may display a single peak and thus be unimodal. The molecular weight distribution curves for the individual components may be superimposed onto a common chart to form the weight distribution curve for the polymer resin as a whole. Upon such superimposition, the resultant curve for the polymer resin as a whole may be multimodal or show n distinct peaks corresponding to n polymer components of differing molecular weight distributions. For example, a bimodal polymer resin may show two distinct peaks corresponding to two individual components. For example, a bimodal polymer resin may have a first component that may be generally characterized as a higher molecular weight polymer component and a second component that may be generally characterized as a lower molecular weight polymer component. A trimodal polymer composition may show three distinct peaks corresponding to three individual polymer components. Alternatively, superimposition of the molecular weight distribution curves from the individual components may show a single peak that is broadened in comparison with the curves for the individual components corresponding to polymer fractions having different but overlapping molecular weight distributions. Such compositions while appearing unimodal may be deconvoluted into their individual component peaks and can thus be shown to be a multimodal composition.

The individual components of the PE base resin may comprise a homopolymer, a copolymer, or blends thereof. In an aspect, the components of the PE base resin may be a copolymer comprised of a polymer of ethylene with one or more comonomers such as alpha olefins. In an aspect, the PE base resin comprises a higher molecular weight (HMW) component and a lower molecular weight (LMW) component, for example a HMW copolymer component (e.g., a copolymer of ethylene and 1-hexene) and a LMW copolymer component (e.g., a copolymer of ethylene and 1-hexene). In an embodiment, the PE base resin is a dual-metallocene polyethylene having a HMW component comprised of polyethylene copolymer with 1-hexene and a LMW component comprised of polyethylene copolymer with 1-hexene.

In an embodiment, the PE base resin comprises a LMW component and a HMW component, wherein the LMW component is present in the PE base resin in a weight fraction of from about 0.3 to about 0.7, alternatively from about 0.4 to about 0.7 or alternatively from about 0.5 to about 0.65 based on total weight of the PE base resin, and the HMW component makes up the balance of the PE base resin. In an embodiment, PE base resins of the type disclosed herein may be characterized by a LMW component having a peak molecular weight ($M_p$) ranging from about 25 kg/mol to about 65 kg/mol, alternatively from about 35 kg/mol to about 60 kg/mol, or alternatively from about 40 kg/mol to about 50 kg/mol and a HMW component having a $M_p$ ranging from about 67 kg/mol to about 600 kg/mol, alternatively from about 200 kg/mol to about 600 kg/mol, or alternatively from about 400 kg/mol to about 500 kg/mol. Herein, the $M_p$ refers to the peak molecular weight.

It is to be understood that in the case of polymer blends (e.g., physical or reactor blends) the individual components of the blend may be described approximately herein. Thus, any metrics or characteristics provided herein for the individual components of a polymer blend are approximated for that portion of the material corresponding to the designated component and are provided as values for some portion of the material within the larger context of the entire blend. Thus where it is not possible to measure the characteristics of an individual component (e.g., reactor blend) such characteristics when represented herein may contain some contribution from other components of the blend.

The molecular weight distribution (MWD) of the PE base resin may be characterized by the ratio of the weight average molecular weight to the number average molecular weight, which is also referred to as the polydispersity index (PDI) or more simply as polydispersity. The number average molecular weight is the common average of the molecular weights of the individual polymers calculated by measuring the molecular weight of n polymer molecules, summing the weights, and dividing by n. The weight average molecular weight describes the molecular weight distribution of a polymer composition and is calculated according to equation 1:

$$M_n = \frac{\sum_i N_i M_i^2}{\sum_i N_i M_i} \quad (1)$$

where $N_i$ is the number of molecules of molecular weight $M_i$. All molecular weight averages are expressed in gram per mole (g/mol).

In an embodiment, the individual components of the PE base resin (e.g., the LMW component and the HMW component) have narrow molecular weight distributions (MWD). More specifically, the HMW component may have a PDI of from about 2 to about 5, alternatively from about 2 to about 4, or alternatively from about 2 to about 3. The LMW component may have a PDI of from about 2 to about 5, alternatively from about 2 to about 4, or alternatively from about 2 to about 3. The resultant PE base resin (i.e., including both the LMW and HMW components) may have a broad MWD of from about 5 to about 30, alternatively from about 5 to about 20, or alternatively from about 5 to about 10.

In an embodiment, a PE base resin prepared as described herein may display one or more types of melt fracture during polymer melt formation and processing such as extrusion molding. The type, extent, and conditions under which the polymer melt experiences melt fracture may vary depending on the polymer microstructure. In an embodiment, a method of identifying a PE base resin having desirable processing characteristics comprises obtaining a plurality of PE base resins of the type disclosed herein and measuring the shear stress as a function of shear rate for the plurality of base resins using capillary rheometry.

Capillary rheometry is a technique whereby a sample undergoes extrusion through a die of defined dimensions and the shear pressure drop across the die is recorded at set volumetric flow rates. In an embodiment, a PE base resin of the type disclosed herein is the subject of a capillary extrusion experiment to characterize the melt fracture behavior of the resin. The capillary extrusion experiment may be carried out using any suitable methodology. For example, the capillary extrusion experiments may be carried out at 190° C., using a dual-bore capillary rheometer (Rosand RH-7, Malvern) operated in constant speed mode. A capillary die with 1 mm diameter and of 16 mm length and an orifice die with 1 mm diameter may be used. The entrance angle for the dies can be 180°, and the contraction ratio from the reservoir barrel to the die may be about 15. A step shear rate test can be performed for a given sample to obtain the apparent wall shear rate ($\dot{\gamma}_A$) and apparent wall shear stress ($\sigma_A$) according to equation 2:

$$\dot{\gamma}_A = \frac{4Q}{\pi R^3} \text{ and } \sigma_A = \frac{R}{2}\frac{\Delta P}{L} \quad (2)$$

where R is the capillary radius, $\Delta P$ is the measured pressure drop across the capillary, L is the capillary length, and Q is the imposed flow rate. Bagley and Rabinowitsch corrections are applied to obtain more realistic shear stress value at the wall ($\sigma_W$) and shear rate ($\dot{\gamma}_W$) respectively according to equation 3:

$$\sigma_W = \frac{R}{2}\frac{(\Delta P - P_o)}{L} \text{ and } \dot{\gamma}_W = \left(\frac{3+b}{4}\right)\dot{\gamma}_A \quad (3)$$

where $P_O$ is measured pressure for the orifice die and b= d(log $\dot{\gamma}_A$)/d(log $\sigma_W$). Extrudates can be collected at different shear rates and imaged using an optical microscope to identify onset critical stresses and shear rates of the melt fractures.

In an embodiment, PE base resins of the type disclosed herein display a surface melt fracture (SMF) that occurs at a critical stress of less than about 200 kiloPascals (kPa), alternatively from about 30 kPa to about 180 kPa. The critical stress refers to the wall shear stresses that serves as the trigger for the onset of a particular extrudate distortion or melt fracture. SMF may also be referred to as the smooth to matte transition or the sharkskin melt fracture (SSMF). The onset of SMF is a polymer instability in the PE base resin that originates at the exit of a die during extrusion of melted resin (i.e., melt) through the die. The SMF may be attributable to the acceleration (high stretching rate) of the melt as it exits the die. Without wishing to be limited by theory, it is hypothesized that melt leaving the die in the neighborhood of the wall experiences a large, rapid, tensile deformation as the velocity field adjusts from the no-slip boundary condition to the free-surface condition. The large stresses on the free surface cause periodic cracks that result into small amplitude periodic distortions termed sharkskin, which is a visible surface defect present in the product being produced from the die (e.g., pipe). The critical stress is related to the onset of SMF.

In an embodiment, the PE base resins of this disclosure display a reduced amount of slip-stick fracture (SSF) when compared to a unimodal PE base resin or a PE that is not made using a dual-metallocene catalyst. SSF is believed to occur when the shear stress at the die wall exceeds the critical stress. When this occurs, the melt jerks forward as a plug, relieving the pressure behind it and allowing the oriented chain segments to recoil somewhat. Once the pressure is relieved, the rate of movement of the polymer slows and it re-establishes the non-slip boundary condition. During SSF the pressure within the die fluctuates and the polymer output is unsteady. The magnitude of SSF pressure oscillation is recorded and correlated with the onset of melt fractures. In an embodiment, a PE base resin of the type disclosed herein displays a tendency to SSF pressure oscillation that is less than a unimodal PE base resin or a PE that is not made using a dual-metallocene catalyst. In an embodiment, a PE base resin of the type disclosed herein is characterized by a magnitude of slip-stick of from about 300 psi to about 1500 psi, alternatively from about 500 psi to about 1500 psi, alternatively from about 500 psi to about 900 psi, or alternatively from about 600 psi to about 800 psi.

In an embodiment, a PE base resin of the type disclosed herein may display surface melt fracture that occurs at a critical shear rate of from about 10 s$^{-1}$ to about 100 s$^{-1}$, alternatively from about 10 s$^{-1}$ to about 50 s$^{-1}$, or alternatively from about 20 s$^{-1}$ to about 40 s$^{-1}$. Herein, the shear rate refers to the extrusion speed that serves as the trigger for the onset of a particular extrudate distortion or melt fracture. This relates to the critical stress discussed previously and the melt flow index/viscosity of a PE base resin.

Figure 1B:
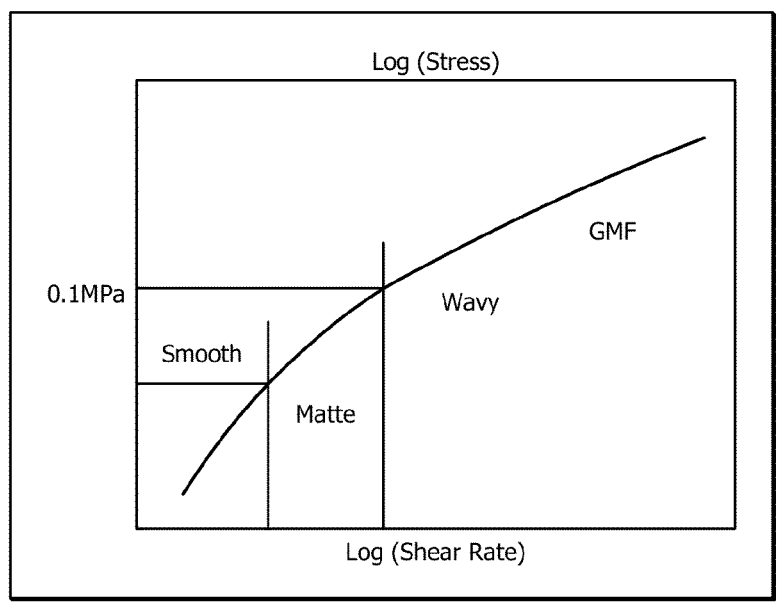
FIG. 1B is a schematic of the melt fracture behavior of a multimodal polyethylene base resin of the type disclosed herein.

The melt fracture behavior of a conventional unimodal PE base resin and a PE base resin of the type disclosed herein is schematized in FIGS. 1A and 1B, respectively. FIG. 1 show plots of the log of shear rate in MegaPascals (MPa) units with the log of shear stress in inverse seconds (1/s) units, each of which were determined as described in more detail herein. In an embodiment, a PE base resin displaying melt fracture behavior consistent with FIG. 1B (e.g., the same as or substantially similar thereto) may be referred to as having an about smooth curve of the log of shear stress as a function of the log of shear rate. FIG. 1A shows four regions associated with characteristics of the melt, namely smooth, sharkskin, slip-stick, and gross melt fracture (GMF). FIG. 1B shows four regions associated with characteristics of the melt, namely smooth, matte, wavy, and gross melt fracture (GMF).

In an embodiment, a plurality of PE base resins of the type disclosed herein are subjected to capillary rheometry. In an embodiment, a method of identifying a PE base resin having a reduced tendency to melt fracture comprises identifying a PE base resin having a magnitude of slip-stick of greater than about 300 psi, a smooth to matte transition of greater than about 90 kPa of stress and a shear rate of greater than about 10 s⁻¹. Such resins having a magnitude of slip-stick of greater than about 300 psi, a smooth to matte transition of greater than about 90 kPa of stress and a shear rate of greater than about 10 s⁻¹ and thus a reduced tendency to melt fracture, are termed polymers with a reduced melt fracture tendency (PRMT). The PRMTs may be selected and further processed into articles (e.g., pipes) as described in more detail herein.

In an embodiment, capillary extrusion experiments are carried out and identify PE base resins characterized by at least one of the following conditions a magnitude of slip-stick less than about 300 psi; a smooth to matte transition of less than about 90 kPa of stress and a shear rate less than about 10 s⁻¹. Such resins may display an increased tendency to melt fracture and are herein termed resins with increased melt fracture (RIM).

As disclosed herein a PRMT (e.g, metallocene-catalyzed multimodal PE base resin) having a reduced tendency to melt fracture may be characterized by a magnitude of slip-stick greater than about 300 psi, a smooth to matte transition of greater than about 90 kPa of stress and a shear rate greater than about 10 s⁻¹. Further as disclosed herein, measurement of the magnitude of slip-stick pressure oscillation and the stress and shear rate for the smooth to matte transition may be made by capillary extrusion experiments. As will be understood by one of ordinary skill in the art, capillary extrusion experiments are both time and labor intensive. In an embodiment, an alternative methodology for identifying PE base resins having a reduced tendency to melt fracture (e.g., PRMT) comprises relating one or more processing characteristics of a PE base resin of the type disclosed herein (e.g., melt fracture behavior) to measurements carried out using techniques that inform on polymer microstructure such as Gel Permeation Chromatography (GPC).

In an embodiment, an analytical relationship between the polymer microstructure and processing characteristic is defined by chemometric analysis. The analytical relationship may be in the form of a mathematical equation. Chemometric analysis refers to the application of statistical and pattern recognition techniques to data provided by chemical analysis such as GPC data.

In an embodiment, the methodology of relating one or more processing characteristics of a PE base resin of the type disclosed herein (e.g., melt fracture behavior) to measurements carried out using techniques that inform on polymer microstructure such as GPC is used to identify a RIM, and such RIM may be modified as disclosed herein to yield a PRMT. In an embodiment, a method comprises relating the MWD profile of a polymer to the melt fracture properties as determined by capillary rheometry.

In an embodiment, chemometric analysis is performed on data obtained from a series of at least two training samples of PE base resins of the type disclosed herein having different, known compositions, which are studied to ascertain interrelationships between the data and one or more known sample characteristics. In an embodiment, the data comprises information on the polymer microstructure (e.g., data as determined by GPC) and the one or more sample characteristics comprise melt fracture behavior (e.g., melt fracture behavior of the type alternatively provided via capillary analysis as described herein, that is the characteristics used to identify a RIM or a PRMT). Alternatively, at least 5 training samples, or at least 10 training samples, or at least 20 training samples, or at least 30 training samples, or at least 40 training samples, or at least 50 training samples can be analyzed. The limit to the number of training samples that can be analyzed together usually is dictated by limitations of the software and computer hardware employed, and no specific upper limit to the number of samples to be used is contemplated.

Normally (as here), a range of training samples having different compositions is tested so the differences in the data obtained for the respective samples can be evaluated to find changes in a pertinent dependent variable arising from changes in an independent variable. One can, however, employ a set of training samples that include some duplicate, triplicate, or more redundant samples. The inclusion of redundant training samples in a set that also includes many diverse training samples may reduce the statistical error. Training samples optionally can be samples characterized in prior work, the literature, by interpolation or extrapolation from other training samples, or other sources, as opposed to samples that are made physically available.

Another issue is the nature of the training samples selected. Training samples normally will closely resemble the desired test samples, so the properties of the test samples and the training samples can readily be compared. The set of training samples should include members having a range of properties that goes beyond the expected properties of the test samples. Selecting a broad range of training samples will allow a more robust model to be developed, so the data obtained from the training samples can be used for samples that may have properties somewhat different from the expected ones.

Selecting a broad range of samples also allows the use of interpolation instead of extrapolation to relate the properties of the training samples to the test samples. The training samples can, but need not be made by separating fractions of a test sample. In an embodiment, materials other than those of the test samples can be used as training samples or constituents of training samples. Analytical data for the training samples can be measured, obtained from literature values, derived from prior work, or obtained from a combination of sources. The polymer microstructure data results (e.g., as provided by GPC) or other polymer microstructure information for the training samples are analyzed to find correlations between polymer microstructure and the predicted melt fracture behavior of the polymer. Analysis of the relationship between the polymer microstructure (e.g., as provided by GPC data) and the predicted melt fracture behavior may be carried out using any suitable chemometric software. In an embodiment, the chemometric software compares the polymer microstructure results from the training samples and finds correlations between the polymer microstructure results (e.g., GPC data) of the polymer and the melt fracture behavior.

In an embodiment, chemometric analysis of the relevant data (e.g., GPC data) is carried out using any suitable chemometric technique. Examples of suitable chemometric techniques include but are not limited to Partial Least Squares Regression (PLS), Multilinear Regression Analysis (MLR), Principal Components Regression (PCR), Principal Component Analysis (PCA) and Discriminant Analysis, as well as Design of Experiment (DOE) and Response Surface Methodologies. In an embodiment, the chemometric analysis is carried out using PLS2. PLS refers to a wide class of methods for modeling relations between sets of observed variables by means of latent variables. The underlying assumption of all PLS methods is that the observed data is generated by a system or process which is driven by a small number of latent variables.

In an embodiment, a methodology for evaluating the melt fracture characteristics of a polymer sample comprises identifying at least two polymer training samples having different but known melt fracture characteristics. The training samples may be subjected to GPC to determine various characteristics of the polymer sample such as the molecular weight distribution, amount of each constituent present in the polymer sample, weight average molecular weight and the like. Typically, the results of the GPC analysis are determined using standard computer software to plot and/or analyze the results of the chromatographic separation. In the alternative, GPC data for the training samples may be obtained from any suitable source (e.g., literature values). Analysis of the GPC data may then be carried out to determine at least one parameter that correlates with the known difference in melt fracture characteristics among the training samples. Chemometric analysis may be carried out to define the number of polymer microstructure data, type of polymer microstructure data and relationship between the polymer microstructure data that would serve as a proxy for the observed melt fracture characteristics of the PE base resins. It is to be understood that establishing that a relationship exists between the proxy data (e.g., GPC) and the actual characteristic being observed (e.g., melt fracture) and analytically defining that relationship will be dependent on the nature of the training samples chosen as discussed previously herein.

In an embodiment, GPC data for polymer samples having unknown melt fracture characteristics (test samples) are provided. The values of the parameters determined to be correlated to melt fracture characteristics in the training samples are identified for the test samples. The analytical relationship found by analysis of the training samples is applied to these parameter values identified in the test samples and as a result the melt fracture characteristics of the test samples are predicted. From such predicted characteristics, the sample may be identified as a RIM or a PRMT. For example, DOE of the GPC data for a set of training samples may define a relationship between a melt fracture characteristic (Y) and the polymer microstructure as an equation having measurable variables (e.g., $M_p$) and constants determined by chemometric analysis of the training sample. Thus, utilizing the data obtained from GPC analysis of the test samples (e.g., Mp) and the mathematical relationship identified by chemometric analysis of the training samples a melt fracture characteristic for the test samples can be predicted.

In an embodiment, a method of identifying PE base resins having one or more desired processing characteristics comprises obtaining a plurality of PE base resins of the type disclosed herein having a known molecular weight distribution, a known magnitude of slip-stick, a known stress for a smooth to matte transition, and a known shear rate (i.e., training samples). The method may further comprise performing chemometric analysis to determine an analytical relationship between the known molecular weight distribution, the known magnitude of slip-stick, the known stress for a smooth to matte transition, and the known shear rate for the plurality of PE resins (i.e., training samples). The method may further comprise obtaining a plurality of samples of multimodal metallocene-catalyzed PE resins, each having a known molecular weight distribution, an unknown magnitude of slip-stick, an unknown stress for a smooth to matte transition, and an unknown shear rate (i.e., test samples) and utilizing the analytical relationship to determine a value for the unknown magnitude of slip-stick, a value for the unknown stress for a smooth to matte transition, and a value for the unknown shear rate for each of the plurality of multimodal metallocene-catalyzed PE samples (i.e., test samples). Based on the predicted melt fracture characteristics the method may further comprise identifying multimodal metallocene-catalyzed PE resins (e.g., PRMPs) having a reduced tendency to melt fracture characterized by samples having a magnitude of slip-stick greater than about 300 psi, a smooth to matte transition of greater than about 90 kPa of stress and a shear rate greater than about 10 $s^{-1}$. The method may further comprise forming the PRMPs into articles such as pipe.

In an alternative embodiment, based on the predicted melt fracture characteristics the method may further comprise identifying multimodal metallocene-catalyzed PE resins (e.g., RIMs) having an increased tendency to melt fracture characterized by samples having a magnitude of slip-stick less than about 300 psi, a smooth to matte transition of less than about 90 kPa of stress and a shear rate less than about 10 $s^{-1}$. The method may further comprise modifying the identified RIM to decrease the tendency of the material to melt fracture. The modified RIM may be analyzed (e.g., via GPC) to determine molecular weight distribution, and thereby predict melt fracture behavior (as described herein) of the modified RIM, e.g., to determine whether the RIM has been modified to yield a PRMP. The method may further comprise forming the PRMT into articles such as pipe.

As described herein the flow properties determined by capillary rheometry may be related to the entire MWD profile of the polymer. Herein, the MWD is the metric used to inform on the polymer microstructure. As will be understood by one of ordinary skill in the art, the MWD of the polymer is dependent on several factors. In an embodiment, a method comprises performing chemometric analysis in order to establish the relationship between one or more factors contributing to the MWD and the melt fracture behavior of the polymer. For example, using statistical design of experiment (DOE) and response surface methodology, the MWD profile of a polymer in terms of its molecular weight components and their subsequent effect on the capillary results may be determined.

In an embodiment, the MWD profile of a particular polymer is described as the linear combination of n factors where n is equal to or greater than 2, alternatively equal to or greater than about 3, or alternatively equal to or greater than about 4. In an embodiment, n is 2 and the components are designated P1 and P2. In such embodiments, P1 and P2 can each be assigned a $M_p$, PDI, and weight fraction composition. Using a combination of these two components (i.e., P1 and P2), the effects of various MWD profiles on the melt fracture characteristics of the polymer (i.e, capillary response) can be explored in a systematic manner. The components of the MWD (i.e., P1 and P2) can be represented using any suitable peak shape such as Gaussian or Schluz-Flory. In an embodiment, the components of the MWD (i.e., P1 and P2) are represented using log normal (i.e., Gaussian) shaped peaks. In an embodiment, the polymer is a physical blend or mixture of polymers where the exact number of components is known as well as the nature of these components in terms of $M_w$ and $M_n$. In an embodiment, the MWD of a polymer having been described initially as the linear combination of two components (i.e., P1 and P2) can be further characterized by the peak molecular weight of each component ($M_p$ P1 and $M_p$ P2), the PDI of each component, and the weight fraction of each component.

Figure 7:
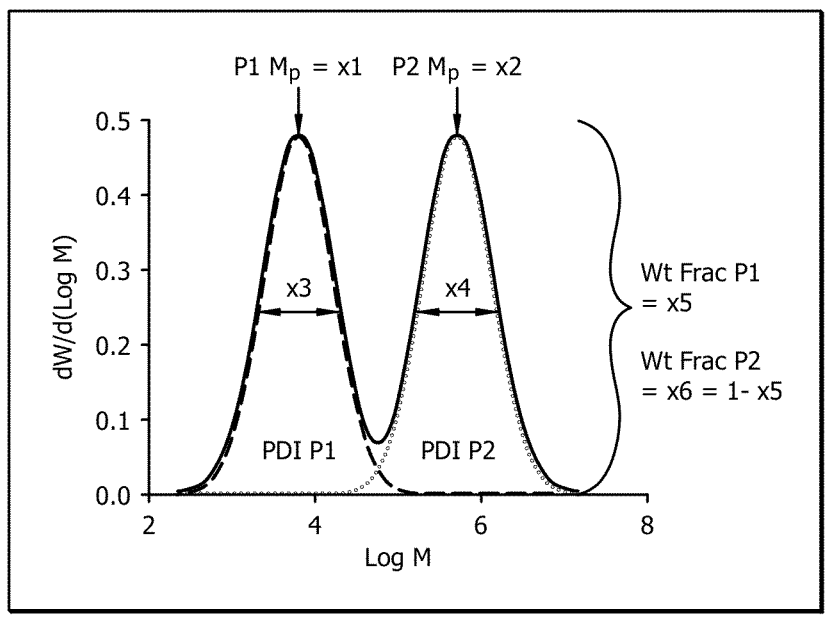
FIG. 7 is a depiction of the molecular weight distribution of a bimodal polymer sample.

In an embodiment, the method further comprises digitally generating MWD profiles by varying the individual parameters that characterize the MWD (i.e., $M_p$, PDI and weight fraction of each component). Given that the MWD distribution is equal to unity (i.e., 1) and is described by two component peaks (i.e., n=2), the number of parameters that are used to describe the MWD can be reduced from six to five, where the weight fraction composition of P2 can be written in terms of the weight fraction of P1 (i.e., wt frac. P2=1-wt frac. P1). Each of these parameters is illustrated in FIG. 7. The MWD profile generated for each variation of parameters may be utilized to predict a melt fracture characteristic (e.g., magnitude of slip-stick). Digitally varying the parameters and identifying the relative contribution of each parameter and/or combination of parameters to the particular melt fracture characteristic may aid in elucidating the analytical relationship between a particular parameter and/or combination of parameters and the resultant melt fracture characteristic (e.g., magnitude of slip-stick). In an embodiment, the relationship between one or more of the varied parameters and the result (e.g., magnitude of slip-stick) may be codified in the form of a mathematical algorithm of the type previously disclosed herein and exemplified below. In some embodiments, the algorithm includes all of the parameters of the MWD identified to contribute to the resultant melt fracture characteristic (e.g., magnitude of slip-stick).

In an embodiment, the method further comprises statistical analysis of the results of the chemometric determinations to identify parameters that significantly contribute to the resultant melt fracture characteristic (e.g., magnitude of slip-stick). Herein, "significant" refers to statistical significance which is defined as the likelihood that the result obtained has occurred by chance. The statistical significance of the analysis can determined using any suitable methodology. For example, the method may further comprise analysis of the variance in the results of the chemometric determinations. Analysis of Variance (ANOVA) methods are used in data analysis to determine differential expressions under different experimental conditions. In a one-way ANOVA, there is one experimental factor under investigation. For example, the factor may be the effect of the peak molecular weight on the magnitude of slip-stick. In a two-way ANOVA, there are two factors under investigation, for example, the effect of the amount of the LMW component and PDI of the LMW component on the magnitude of the slip-stick. Each factor may have multiple levels. Interaction between the two factors is also included in the ANOVA analysis. ANOVA may also be carried out in order to determine whether there are statistical differences among the means of measurements in different measurement groups. As an example, the different measurement groups may contain measurements of the magnitude of slip-stick at different weight fractions of a particular component. In each group, there may be several replicate measurements under the same conditions. First, one finds the within-group variance and the between-group variance. The within-group variance is the measurement variance of measurements within a set of experiments carried out under the same conditions. The between-group variance is the measurement variance of the means of experiments carried out under different conditions. The within-group variance reflects the measurement error of the measurement technology, and the between-group variance includes both the measurement error of the measurement technology and changes caused by different conditions. Then the between-group variance is compared to the within-group variance. If the between-group variance is significantly larger than the within-group variance, it may be concluded that the different conditions have produced statistically significant changes in the determinations of the melt fracture characteristics (e.g., magnitude of slip-stick). In ANOVA analysis, the underlying null-hypothesis is that all conditions have the same mean. With the estimated mean squares and degrees of freedom, a p-value of F-statistics can be calculated. The p-value is the probability that the null-hypothesis may be accepted. When the p-value is lower than a given threshold, for example p-value<0.01, the null-hypothesis can be rejected and the alternative hypothesis, which means that some of the experimental conditions have different means, can be accepted. In other words, some experimental conditions have produced changes in the melt fracture characteristics In an embodiment, the algorithm describing the relationship between one or more of the varied parameters and the result (e.g., magnitude of slip-stick) is modified to reflect only those parameters found to contribute significantly to the result. As will be understood by one of ordinary skill in the art, statistical models may be constructed and extrapolated to produce values of parameters that lie outside of the range observable or probable for actual samples. For example, utilizing the methodologies disclosed herein, models may be constructed which predict a negative value for the magnitude of slip-stick. In such instances, the limitations of the model are realized and the negative values obtained can be assumed to have a value of zero.

The results of determining the relationship between the individual parameters contributing to the MWD and a particular melt fracture characteristic may be employed to identify the parameters and/or combination of parameters that can be adjusted to modify the melt fracture characteristic of a particular resin. In an embodiment, a PMRT is prepared by blending n components having one or more parameters (e.g., wt fraction of each component, PDI of each component) determined to provide a polymer blend having one or more desirable melt fracture characteristics. As will be understood by one of ordinary skill in the art, the particular design of a polymer having a reduced tendency to melt fracture (e.g., PRMT) will be dependent on the results of the chemometric and statistical analysis which will identify any relationships that exist between the parameters contributing to the MWD and the particular melt fracture characteristic. For example, the results of the chemometric analysis may indicate that one of the significant factors in the stress for the smooth to matte transition is peak molecular weight of the LMW component. Consequently, adjusting the peak molecular weight of the LMW component to within a range indicated by the results of the chemometric analysis (e.g., adjustments responsive to the chemometric analysis results) would be expected to produce a resin having a stress for the smooth to matte transition within some user and/or process desired range. Consequently there can be numerous polymer designs which display a reduced tendency to melt fracture as such solutions to the problem of melt fracture are dependent on a variety of parameters but may be understood and employed in view of the disclosure herein (e.g., responsive to chemometric analysis).

For example, a method for reducing or eliminating melt fracture (e.g., SMF) in a RIM of the type disclosed herein comprises increasing the molecular weight of the LMW component. In an embodiment, a method for reducing or eliminating melt fracture (e.g., SMF) in a RIM of the type disclosed herein comprises decreasing both the amount of the LMW component and the $M_w$ of the HMW component. In an embodiment, a method for reducing or eliminating melt fracture (e.g., SMF) in a RIM of the type disclosed herein comprises introducing a polymer component having a MWD peak mode that is disposed between the MWD peak modes of the LMW component and HMW component. Such modifications may be carried out by altering one or more process conditions during polymerization of the LMW component and/or the HMW component (e.g., during formation of a reactor blend) and/or by replacing and/or adding one or more components during formation of a mechanical blend such as selecting an alternative LMW component and/or HMW component than that present in the RIM and/or by adding an additional component having a MWD peak mode between those of the LMW and HMW components. In various embodiments, such modifications of the RIM are effective to convert the RIM to a PRMT.

It is to be understood that the methodologies disclosed herein are intended to provide modifications to components that are constituents of a multimodal polymeric material. Further, it is to be understood that in the case of a polymer blend it may be difficult or impossible to independently act upon or characterize a single component of the multicomponent blend without the influence and/or presence of the other components of the blend. Thus, the methods disclosed herein when referring to a component of a polymer blend (e.g., HMW component) refer to the ability to act upon or modify a portion of the polymer designated as the particular component with the understanding that these components may not be independent entities and/or that some impact may occur on another component of the polymer.

Without wishing to be limited by theory, RIMs of the type disclosed herein may exhibit the aforementioned melt fracture characteristics such as shown in FIG. 1B as a result of the composition having components that behave as discrete entities. Under the processing conditions typically employed for manufacture of an article from a RIM of the type disclosed herein, the LMW component may result in migration toward the surface that is not impeded by molecular entanglements to the HMW component. Thus, the unique melt fracture and slip behaviors of RIMs of the type disclosed herein are attributable to the fact that the MWD peaks of the two components are considerably separated and the low mode has a significant amount of LMW component such that entanglements are limited within this mode. The molecular segregation of the LMW components results in the concentration of these components near the die wall during the extrusion flow which in turn results in significant apparent wall slip and less elastic effects that influence the melt fracture behavior. Accordingly, various embodiments for modifying the melt fracture characteristics of the RIM include holding constant the MWD peak associated with the HMW component and modifying the MWD of the LMW component (e.g., moving the location of and/or adjusting the size of the MWD peak associated with the LWM component).

In an embodiment, the PRMT is a multimodal metallocene-catalyzed resin. Further, such resins displaying a magnitude of slip-stick greater than about 300 psi, a smooth to matte transition of greater than about 90 kPa of stress, and a shear rate greater than about 10 s$^{-1}$ are characterized by a reduced tendency to melt fracture.

PRMTs as described herein may be formed into various articles, including but not limited to, household containers, utensils, film products, drums, fuel tanks, pipes, geomembranes, and liners. In an aspect, the PRMT of this disclosure is fabricated into a pipe by a plastics shaping process such as extrusion. A method of making a polymeric pipe comprises extruding the polymer or copolymer in a molten state through a die to form the polymeric pipe and cooling the pipe.

Pipe extrusion in the simplest terms is performed by melting, conveying polyethylene pellets into a particular shape (generally an annular shape), and solidifying that shape during a cooling process. There are numerous steps to pipe extrusion as provided below. The polymer feedstock can either be a pre-pigmented polyethylene resin or it can be a mixture of natural polyethylene and color concentrate (referred to as "Salt and Pepper blends"). In North America, the most common feedstock for pipe extrusion is "Salt and Pepper blends." In Europe and other areas of the world, the most common feedstock for pipe extrusion is pre-pigmented polyethylene resin. Feedstock is rigidly controlled to obtain the proper finished product (pipe) and ultimate consumer specifications.

The feedstock is then fed into an extruder. The most common extruder system for pipe production is a single-screw extruder. The purpose of the extruder is to melt, convey, and homogenize the polyethylene pellets. Extrusion temperatures typically range from 178° C. to 250° C. depending upon the extruder screw design and flow properties of the polyethylene.

The molten polymer is then passed through a die. The die distributes the homogenous polyethylene polymer melt around a solid mandrel, which forms it into an annular shape. Adjustments can be made at the die exit to try to compensate for polymer sag through the rest of the process. In order for the pipe to meet the proper dimensional parameters, the pipe is then sized. There are two methods for sizing: vacuum or pressure. Both employ different techniques and different equipment.

Next, the pipe is cooled and solidified in the desired dimensions. Cooling is accomplished by the use of several water tanks where the outside pipe is either submerged or water is sprayed on the pipe exterior. The pipe is cooled from the outside surface to the inside surface. The interior wall and inside surfaces of the pipe can stay very hot for a long period of time, as polyethylene is a poor conductor of heat. Finally, the pipe is printed and either coiled or cut to length.

In an embodiment, the PRMT is used to prepare the pipe has a density of greater than about 0.925 g/ml to about 0.942 g/ml, alternatively from about 0.928 to about 0.940 g/ml or alternatively from about 0.930 g/ml to about 0.940 g/ml as determined in accordance with ASTM D1505.

A majority of the field failures in pressure pipe (gas transport) applications are attributable to a brittle fracture mode referred to as slow crack growth (SCG). This has led to the development of many lab-scale tests, such as the Pennsylvania Notch Tensile Test (PENT; ASTM F1473) and the Full Notch Creep Test (FNCT; ISO 16770.3), to predict the resistance to SCG of various polyethylenes. In the PENT test, rectangular bars notched (to ensure brittle fracture) are subjected to a constant load at 80° C. until they finally break. The time to failure is recorded and is generally thought to be reflective of the SCG resistance of the polymer. A pipe prepared from the PRMTs disclosed herein may display PENT values of from about 500 hours to about 20,000 hours, alternatively from about 550 hours to about 20,000 hours, or alternatively from about 600 hours to about 20,000 hours.

A modified Charpy impact test, referred to as the Razor-Notched Charpy Impact Test, has emerged as a useful indicator of the resistance to RCP fractures. This modified Charpy test is described in detail in ASTM F2231. This test involves measuring the impact energy when a thin molded rectangular plaque (with a razor notch) is impacted by a swinging pendulum. This test can be performed at multiple temperatures; enabling one to determine the temperature at which the failure mode changes from ductile to brittle. The results from this test are as follows: (i) impact energy (in Joules) at room temperature and (ii) the lowest temperature at which the failure was clearly ductile (hinge break with an impact energy >0.15 J); for convenience, this temperature will be referred to as the Charpy ductile to brittle critical temperature, Charpy $T_{db}$. Generally speaking, a higher room-temperature impact energy and a lower Charpy $T_{db}$ means the ensuing pipe will have better RCP resistance.

A pipe prepared from the PRMTs disclosed herein may have a Charpy $T_{db}$ less than about −25° C.; alternatively, the Charpy $T_{db}$ is less than about −15° C., or alternatively, the Charpy $T_{db}$ may be less than about −10° C. Charpy impact energy is a measure of an article's impact toughness. Test articles of polymer produced in accordance with the present disclosure may have a Charpy impact energy of from about 1.0 J to about 3.0 J, or alternatively from about 1.0 J to about 2.58 J as determined in accordance with ASTM F2231 razor-notched Charpy impact test at room temperature.

In an embodiment, a pipe prepared from a PRMT of the type disclosed herein is characterized by the flexural modulus. The flexural modulus may be defined as the ratio, within the elastic limit, of the applied stress on a test specimen in flexure, to the corresponding strain in the outermost fibers of the specimen. In an embodiment, a pipe prepared from a PRMT of the type disclosed herein has a flexural modulus, 2% secant of from about 80 kpsi to about 110 kpsi, alternatively from about 85 kpsi to about 105 kpsi, or alternatively from about 90 kpsi to about 100 kpsi as determined in accordance with ASTM D790 using an injection molded test specimen having a 16.1 inch span depth at a rate of 0.5 in/min.

In an embodiment, a pipe prepared from a PRMT of the type described herein exhibits an elongation at break of greater than about 400%, alternatively greater than about 450% or alternatively greater than about 500% as determined in accordance with ASTM D638. The elongation at break refers to the elongation which corresponds to the tensile breaking strength.

In an embodiment, a pipe prepared from a PRMT of the type described herein displays an increased Young's modulus. Young's modulus is a measure of the stiffness of a material and is defined as the ratio of the rate of change of stress with strain. Young's modulus can be determined experimentally from the slope of a stress-strain curve created during tensile tests conducted on a sample of a material, as determined in accordance with ASTM D638. In an embodiment, the PRMT is used to make a Type IV bar and exhibits a Young's modulus ranging from about 120 kpsi to about 190 kpsi, alternatively from about 120 kpsi to about 185 kpsi, or alternatively from about 120 kpsi to about 180 kpsi when determined in accordance with ASTM D638 at a speed of 2 in/min.

In an embodiment, a pipe prepared from a PRMT of the type described herein exhibits a tensile strength at yield of from about 2600 psi to less than about 3,000 psi, alternatively from 2600 psi to about 2950 psi, or alternatively 2600 psi to about 2,900 psi as determined in accordance with ASTM D638. The tensile strength at yield refers to the tensile stress where an increase in expansion is admitted without an increase in gaining the weight on stress-strain curve. In an embodiment, a pipe prepared from a PRMT of the type described herein exhibits a tensile strength at break of greater than about 4000 psi, alternatively greater than about 4500 psi, or alternatively greater than about 5000 psi as determined in accordance with ASTM D638. The tensile strength at break refers to the tensile stress at the moment the material is destroyed. For both the tensile strength at yield and the tensile strength at break, the pipe prepared from the PRMT was a Type IV bar which was tested at 2 in/min.

In an embodiment, a pipe prepared from a PRMT of the type described herein displays a thermal stability of greater than about 220° C. as determined in accordance with ASTM D3350.

In an embodiment, a pipe prepared from a PRMT of the type disclosed herein is characterized by the extent to which it can resist rapid crack propagation (RCP). The Small-Scale Steady-State (S4) test is the current standard for measuring the RCP resistance of polyethylene pipes. In the S4 test, the pipe specimens are seven diameters long and are sealed at both ends and pressurized with air. Typically, pipe specimens are conditioned externally at the test temperature, and then moved to the S4 rig for testing. A sharp chisel-edged striker impacts the pipe at one end and drives a fast-running crack through the main section of the pipe. While the crack propagates, internal disc baffles spaced along the pipe length suppress axial decompression ahead of it, so that the pressure at the crack-tip is approximately equal to the test pressure during the entire course of crack growth. This promotes steady-state crack growth. Further, in the S4 test, a containment cage around the specimen prevents flaring of the pipe. This also limits the failure mode to steady-state crack propagation while minimizing ductile transient bursting. The S4 test details and procedures are described in the ISO 13477 standard. The test can be performed at a fixed temperature to determine the critical pressure ($P_c$) required to sustain RCP. Alternatively, a series of tests at a given/fixed operating pressure (usually 5 bars) and at various temperatures can be used to measure the critical temperature ($T_c$) for RCP to be sustained. Generally speaking, the temperature of a pipe must be below a critical limit even for RCP to be initiated. Once RCP is initiated, the pressure within the pipe must exceed a critical value to sustain steady state crack propagation. Therefore, for a pipe, low S4 $T_c$ and high S4 $P_c$ will help minimize RCP failures.

The lower the S4 critical temperature the better, since it results in a broader end-use temperature range for the pipe. A pipe fabricated from the PRMTs disclosed herein, having an 8-inch nominal outer diameter with a standard diameter ratio (SDR=OD/t, where t=wall thickness) of about 11, may have a critical temperature value ($T_c$) determined according to ISO DIS 13477 (S4 test) of equal to or less than about 0° C.

Another method of evaluating the SCG resistance is by determining the tensile natural draw ratio (tensile NDR) of the resin. There is some evidence that the tensile NDR is directly related to the SCG resistance of HDPE such that the lower the tensile NDR the higher the resistance to SCG. A description of the correlation of SCG to tensile NDR may be found in: E. Laurent, *Comprehensive Evaluation of the Long-Term Mechanical Properties of PE100 Resin Meeting the Requirements of Modern Installation Techniques*, Plastic Pipes XI Proceedings of the International Conference, Woodhead Publishing Limited (2001); and in an article by L. Hubert, et al published in 2002 in the Journal of Applied Polymer Science Volume 84 page 2308 each of which is incorporated herein by reference in its entirety. In an embodiment, a pipe prepared from a PRMT of the type disclosed herein has a NDR of less than about 500% as determined in accordance with ASTM D 638 for a Type IV bar at a rate of 2 in/min.

In an embodiment, a PRMT of the type disclosed herein displays a melt flow rate (MFR) of less than about 0.4 g/10 min. The MFR is a measurement of the viscosity of a polymer through a defined orifice at a constant temperature and may be determined in accordance with ASTM D1238 using a 2.16 kg loading.

In an embodiment, a pipe prepared from a PRMT of the type disclosed herein is characterized by a hydrostatic design basis (HDB) at 23° C. of from about 1200 psi to less than about 1530 psi and a HDB at 60° C. of from about 960 psi to less than about 1200 psi. The HDB test is used for the purpose of determining the long-term strength characteristic of a plastic pipe and may be determined in accordance with ASTM D2837.

The design stress of a plastic pipe is often referred to as its long-term hydrostatic strength (LTHS) or the minimum required strength (MRS). LTHS, estimated using ASTM D 2837 (USA standard), is the estimated tensile stress in the wall of a pipe in the circumferential orientation which, when applied continuously, will cause failure of the pipe at 100,000 hours. The MRS of a pipe, estimated using the ISO 9080 standard, is the functional equivalent of the LTHS (with a desired lifetime of 50 years) used internationally. The LTHS and/or MRS of a pipe are used to certify gas pipes according to either ASTM D2513 and/or ISO 4437. In other words, these values determine the maximum load that such pipes can bear during their utilization for the transportation of natural gas. In an aspect, the PRMTs disclosed herein may be fabricated into pipe having a MRS of ranging from about $8 \leq \sigma LPL < 10$ MPa.

In an embodiment, a method of assessing melt fracture potential comprises obtaining at least one metallocene-catalyzed polymer sample and performing a capillary extrusion test on the at least one metallocene-catalyzed polymer sample. The method may further comprise identifying a metallocene-catalyzed polymer sample having a magnitude of slip-stick greater than about 300 psi; a smooth to matte transition greater than about 90 kPa and a shear rate of greater than about 10 s$^{-1}$ wherein said identified polymer sample has an increased melt fracture potential when compared to a conventional resin.

In an embodiment, a method of assessing melt fracture potential comprises obtaining at least one metallocene-catalyzed polymer sample. The method may further comprise performing a capillary extrusion test on the at least one metallocene-catalyzed polymer sample. The method may further comprise identifying a metallocene-catalyzed polymer sample having a magnitude of slip-stick less than about 300 psi; a smooth to matte transition less than about 90 kPa and a shear rate of less than about 10 s$^{-1}$ wherein said identified polymer sample has an increased melt fracture potential when compared to a conventional resin not having a magnitude of slip-stick greater than about 300 psi; a smooth to matte transition greater than about 90 kPa and a shear rate of greater than about 10 s$^{-1}$.

In a method of assessing melt fracture potential comprises performing capillary rheometry on a polymer sample to obtain measurements of the shear stress as a function of the shear rate. The method may further comprise plotting the shear stress as a function of shear rate to obtain a plot of the melt fracture behavior. The method may further comprise comparing the plot of melt fracture behavior of the polymer sample to a plot of the melt fracture behavior of a conventional resin. In an embodiment, the method further comprises identifying polymer samples having melt fracture behavior characterized by a magnitude of slip-stick greater than about 300 psi; a smooth to matte transition of greater than about 90 kPa and a shear rate greater than about 10 s$^{-1}$.

In an embodiment, a method of identifying polymer samples having poor processing characteristics comprises obtaining a plurality of metallocene-catalyzed multimodal polyethylene polymer samples. The method may further comprise measuring the shear stress as a function of shear rate for the plurality of dual metallocene-catalyzed polyethylene polymer samples. The method may further comprises identifying dual metallocene-catalyzed polyethylene polymer samples having melt fracture behavior characterized by a magnitude of slip-stick greater than about 300 psi; a smooth to matte transition greater than about 90 kPa and a shear rate greater than about 10 s$^{-1}$.

In an embodiment, a method of assessing melt fracture characteristics of one or more multimodal metallocene-catalyzed polyethylene resins comprises for a training set comprising a plurality of multimodal metallocene-catalyst polyethylene resins, determining melt fracture characteristics comprising a magnitude of slip-stick, a stress for a smooth to matte transition and a shear rate. The method may further comprise measuring a molecular weight distribution for each resin in the training set. The method may further comprise determining a relationship between the melt fracture characteristics and the molecular weight distribution of the training set. The method may further comprise providing one or more validation samples of multimodal metallocene-catalyzed resin having a known molecular weight distribution and an unknown melt fracture characteristic. The method may further comprise predicting the melt fracture characteristics of the validation samples via the relationship.

In an embodiment, a method of predicting melt fracture behavior of a multimodal metallocene-catalyzed polyethylene resin comprises determining the melt fracture behavior of at least two polyethylene resins by capillary rheometry. The method may further comprise determining the molecular weight distribution of the at least two polyethylene resins. The method may further comprise performing chemometric analysis to establish a mathematical relationship between the melt fracture behavior and the molecular weight distribution for the at least two polyethylene resins. The method may further comprise obtaining the molecular weight distribution of the multimodal metallocene-catalyzed polyethylene resin. The method may further comprise utilizing the mathematical relationship to predict the melt fracture behavior of the multimodal metallocene-catalyzed polyethylene resin.

In an embodiment, a method of identifying polyethylene (PE) resins having one or more desired processing characteristics comprises obtaining a plurality of PE resins each having a known molecular weight distribution, a known magnitude of slip-stick, a known stress for a smooth to matte transition, and a known shear rate. The method may further comprise performing chemometric analysis to determine a mathematical relationship between the known molecular weight distribution, the known magnitude of slip-stick, the known stress for a smooth to matte transition, and the known shear rate for the plurality of PE resins. The method may further comprise obtaining a plurality of samples of the multimodal metallocene-catalyzed PE resins, each having a known molecular weight distribution, an unknown magnitude of slip-stick, an unknown stress for a smooth to matte transition, and an unknown shear rate. The method may further comprise utilizing the mathematical relationship to determine a value for the unknown magnitude of slip-stick, a value for the unknown stress for a smooth to matte transition, and a value for the unknown shear rate for each of the plurality of multimodal metallocene-catalyzed PE samples. The method may further comprise identifying the multimodal metallocene-catalyzed PE resins having a reduced tendency to melt fracture characterized by samples having a magnitude of slip-stick greater than about 300 psi; a smooth to matte transition of greater than about 90 kPa of stress and a shear rate greater than about 10 s$^{-1}$.

In an embodiment, a method of preparing pipe comprises identifying a multimodal metallocene-catalyzed PE resin having a reduced tendency to melt fracture characterized a magnitude of slip-stick greater than about 300 psi; a smooth to matte transition of greater than about 90 kPa of stress, and a shear rate greater than about 10 s$^{-1}$. The method may further comprise forming the multimodal metallocene-catalyzed PE resin into the pipe.

In an embodiment, a pipe formed from a multimodal metallocene-catalyzed PE resin having a reduced tendency to melt fracture is characterized by a magnitude of slip-stick greater than about 300 psi; a smooth to matte transition of greater than about 90 kPa of stress and a shear rate greater than about 10 s$^{-1}$.

In an embodiment, a method of preparing a medium-density polyethylene pipe comprise identifying a multimodal metallocene-catalyzed PE resin having a density of greater than about 0.925 g/ml to about 0.940 g/ml, a magnitude of slip-stick greater than about 300 psi; a smooth to matte transition of greater than about 90 kPa of stress, and a shear rate greater than about 10 s$^{-1}$. The method may further comprise forming the multimodal metallocene-catalyzed PE resin into pipe.

In an embodiment, a method comprises identifying a multimodal metallocene-catalyzed PE resin a higher molecular weight (HMW) component and a lower molecular weight (LMW) component; and characterized by at least one of the following conditions a magnitude of slip-stick less than about 300 psi; a smooth to matte transition of greater than about 90 kPa of stress and a shear rate less than about 10 s$^{-1}$. The method may further comprise treating the multimodal metallocene-catalyzed PE resin to provide a modified polymer wherein the treatment comprises at least one of the following (i) increasing the weight average molecular weight of the LMW component; (ii) introducing a bridging polymer; (iii) decreasing the amount of LMW component and decreasing a weight average molecular weight of the HMW component; and (iv) introducing a polymer processing aid to the multimodal metallocene-catalyzed PE resin wherein the modified polymer is characterized by a magnitude of slip-stick greater than about 300 psi; a smooth to matte transition of greater than about 90 kPa of stress, and a shear rate greater than about 10 s$^{-1}$.

Figure 10:
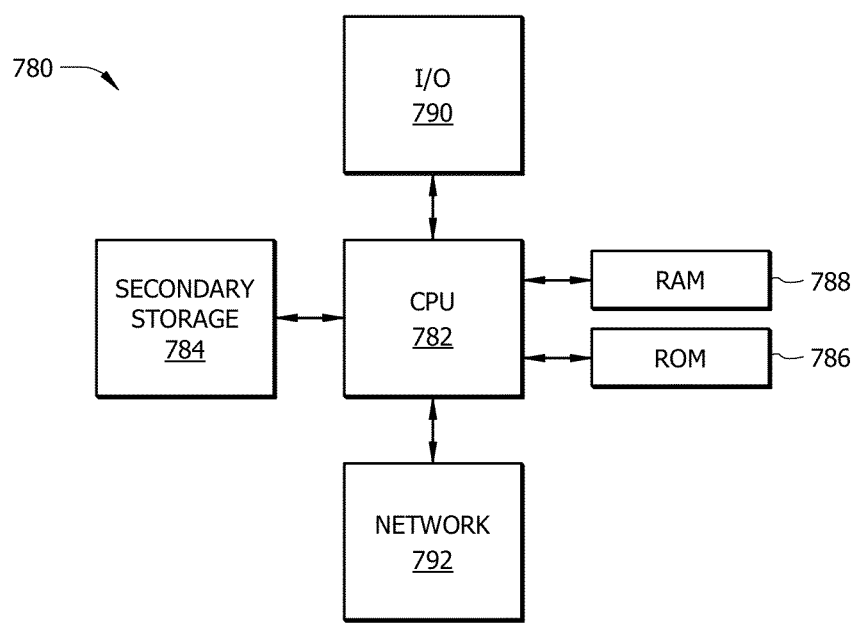
FIG. 10 is a schematic illustration of an embodiment of a computer program product for implementing the disclosed functionalities.

FIG. 10 illustrates a computer system 780 suitable for implementing one or more embodiments disclosed herein. The computer system 780 includes a processor 782 (which may be referred to as a central processor unit or CPU) that is in communication with memory devices including secondary storage 784, read only memory (ROM) 786, random access memory (RAM) 788, input/output (I/O) devices 790, and network connectivity devices 792. The processor 782 may be implemented as one or more CPU chips.

It is understood that by programming and/or loading executable instructions onto the computer system 780, at least one of the CPU 782, the RAM 788, and the ROM 786 are changed, transforming the computer system 780 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 784 is typically comprised of one or more disk drives or tape drives and is used for non-volatile storage of data and as an over-flow data storage device if RAM 788 is not large enough to hold all working data. Secondary storage 784 may be used to store programs which are loaded into RAM 788 when such programs are selected for execution. The ROM 786 is used to store instructions and perhaps data which are read during program execution. ROM 786 is a non-volatile memory device which typically has a small memory capacity relative to the larger memory capacity of secondary storage 784. The RAM 788 is used to store volatile data and perhaps to store instructions. Access to both ROM 786 and RAM 788 is typically faster than to secondary storage 784. The secondary storage 784, the RAM 788, and/or the ROM 786 may be referred to in some contexts as computer readable storage media and/or non-transitory computer readable media.

I/O devices 790 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 792 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 792 may enable the processor 782 to communicate with an Internet or one or more intranets. With such a network connection, it is contemplated that the processor 782 might receive information from the network, or might output information to the network in the course of performing the above-described method steps. Such information, which is often represented as a sequence of instructions to be executed using processor 782, may be received from and outputted to the network, for example, in the form of a computer data signal embodied in a carrier wave.

Such information, which may include data or instructions to be executed using processor 782 for example, may be received from and outputted to the network, for example, in the form of a computer data baseband signal or signal embodied in a carrier wave. The baseband signal or signal embodied in the carrier wave generated by the network connectivity devices 792 may propagate in or on the surface of electrical conductors, in coaxial cables, in waveguides, in an optical conduit, for example an optical fiber, or in the air or free space. The information contained in the baseband signal or signal embodied in the carrier wave may be ordered according to different sequences, as may be desirable for either processing or generating the information or transmitting or receiving the information. The baseband signal or signal embodied in the carrier wave, or other types of signals currently used or hereafter developed, may be generated according to several methods well known to one skilled in the art.

The baseband signal and/or signal embedded in the carrier wave may be referred to in some contexts as a transitory signal.

The processor 782 executes instructions, codes, computer programs, scripts which it accesses from hard disk, floppy disk, optical disk (these various disk based systems may all be considered secondary storage 784), ROM 786, RAM 788, or the network connectivity devices 792. While only one processor 782 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 784, for example, hard drives, floppy disks, optical disks, and/or other device, the ROM 786, and/or the RAM 788 may be referred to in some contexts as non-transitory instructions and/or non-transitory information.

In an embodiment, the computer system 780 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 780 to provide the functionality of a number of servers that is not directly bound to the number of computers in the computer system 780. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 780, at least portions of the contents of the computer program product to the secondary storage 784, to the ROM 786, to the RAM 788, and/or to other non-volatile memory and volatile memory of the computer system 780. The processor 782 may process the executable instructions and/or data structures in part by directly accessing the computer program product, for example by reading from a CD-ROM disk inserted into a disk drive peripheral of the computer system 780. Alternatively, the processor 782 may process the executable instructions and/or data structures by remotely accessing the computer program product, for example by downloading the executable instructions and/or data structures from a remote server through the network connectivity devices 792. The computer program product may comprise instructions that promote the loading and/or copying of data, data structures, files, and/or executable instructions to the secondary storage 784, to the ROM 786, to the RAM 788, and/or to other non-volatile memory and volatile memory of the computer system 780.

In some contexts, a baseband signal and/or a signal embodied in a carrier wave may be referred to as a transitory signal. In some contexts, the secondary storage 784, the ROM 786, and the RAM 788 may be referred to as a non-transitory computer readable medium or a computer readable storage media. A dynamic RAM embodiment of the RAM 788, likewise, may be referred to as a non-transitory computer readable medium in that while the dynamic RAM receives electrical power and is operated in accordance with its design, for example during a period of time during which the computer 780 is turned on and operational, the dynamic RAM stores information that is written to it. Similarly, the processor 782 may comprise an internal RAM, an internal ROM, a cache memory, and/or other internal non-transitory storage blocks, sections, or components that may be referred to in some contexts as non-transitory computer readable media or computer readable storage media. In an embodiment, the computer system 780 is utilized to improve the processing of polymers of the type disclosed herein (e.g., PE base resin). In such an embodiment, information obtained as described herein may serve as input to an analysis component of the computer stored in memory that when executed on the processor, configures the processor to receive a shear stress as a function of shear rate for a plurality of multimodal metallocene-catalyzed polyethylene samples, wherein the determination of the shear stress as a function of the shear rate comprises using capillary rheometry determine values for a slip-stick, a smooth to matte transition, and a shear rate for each of the plurality of multimodal metallocene-catalyzed polyethylene samples based on the shear stress and the shear rate identify individual multimodal metallocene-catalyzed polyethylene resins from the plurality of multimodal metallocene-catalyzed polyethylene samples having a reduced tendency to melt fracture characterized by a magnitude of slip-stick greater than about 300 psi, a smooth to matte transition of greater than about 90 kPa of stress, and a shear rate greater than about $10\ s^{-1}$; an output an identification of the individual multimodal metallocene-catalyzed polyethylene resins to the output device.

The following are additional enumerated embodiments of the concepts disclosed herein.

A first embodiment which is a method of preparing a medium-density polyethylene pipe comprising melting a multimodal metallocene-catalyzed polyethylene resin to form a molten polyethylene, wherein the multimodal metallocene-catalyzed polyethylene resin has a density of from about 0.925 g/ml to about 0.942 g/ml, a magnitude of slip-stick greater than about 300 psi, a stress for smooth to matte transition of greater than about 90 kPa of stress, and a shear rate for smooth to matte transition greater than about $10\ s^{-1}$, wherein the magnitude of slip-stick, stress for smooth to matte transition, and shear rate for smooth to matte transition are determined by a capillary rheology test; and forming the molten polyethylene resin into pipe.

A second embodiment which is the method of the first embodiment wherein the polyethylene resin has a density of from about 0.928 g/ml to about 0.940 g/ml.

A third embodiment which is the method of any of the first through second embodiments wherein the polyethylene resin has a melt flow rate of less than about 0.4 g/10 min.

A fourth embodiment which is the method of any of the first through third embodiments wherein the pipe has a PENT value of from about 500 hours to about 20,000 hours.

A fifth embodiment which is the method of any of the first through fourth embodiments wherein the pipe has a Charpy $T_{db}$ of less than about −25° C.

A sixth embodiment which is the method of any of the first through fifth embodiments wherein the pipe has a Charpy impact energy of from about 1.0 J to about 3.0 J.

A seventh embodiment which is the method of any of the first through sixth embodiments wherein the pipe has a flexural modulus, 2% secant of from about 80 kpsi to about 110 kpsi.

An eighth embodiment which is the method of any of the first through seventh embodiments wherein the pipe has an elongation at break of greater than about 450%.

A ninth embodiment which is the method of any of the first through eighth embodiments wherein the pipe has a Young's modulus of from about 120 kpsi to about 190 kpsi.

A tenth embodiment which is the method of any of the first through ninth embodiments wherein the pipe has a tensile strength at yield of from about 2600 psi to less than about 3,000 psi.

An eleventh embodiment which is the method of any of the first through tenth embodiments wherein the pipe has a tensile strength at break of greater than about 3000 psi.

A twelfth embodiment which is the method of any of the first through eleventh embodiments wherein the pipe has a thermal stability of greater than about 220° C.

A thirteenth embodiment which is the method of any of the first through twelfth embodiments wherein the pipe has a critical temperature value ($T_a$) of equal to or less than about 0° C.

A fourteenth embodiment which is the method of any of the first through thirteenth embodiments wherein the pipe has a critical pressure value ($P_c$) of greater than about 12 bar.

A fifteenth embodiment which is the method of any of the first through fourteenth embodiments wherein the pipe has a tensile natural draw ratio of less than about 500%.

A sixteenth embodiment which is the method of any of the first through fifteenth embodiments wherein the pipe has a hydrostatic design basis at 23° C. of from about 1200 psi to less than about 1530 psi and at 60° C. of from about 960 psi to less than about 1200 psi.

A seventeenth embodiment which is the method of any of the first through sixteenth embodiments wherein the pipe has a minimum required strength of from about 8≤σLPL<10 MPa.

An eighteenth embodiment which is a pipe prepared from a multimodal metallocene-catalyzed polyethylene resin having a density of from about 0.925 g/ml to about 0.942 g/ml, a magnitude of slip-stick greater than about 300 psi; a stress for smooth to matte transition of greater than about 90 kPa, and a shear rate for smooth to matte transition greater than about 10 $s^{-1}$, wherein the magnitude of slip-stick, stress for smooth to matte transition, and shear rate for smooth to matte transition are determined by a capillary rheology test.

A nineteenth embodiment which is the pipe of the eighteenth embodiment having a PENT value of from about 500 hours to about 20,000 hours.

A twentieth embodiment which is the pipe of any of the eighteenth through nineteenth embodiments having a Charpy $T_{db}$ of less than about −25° C.

EXAMPLES

For each of the following examples molecular weights and molecular weight distributions were obtained using a PL 220 GPC/SEC high temperature chromatography unit (Polymer Laboratories, now an Agilent Company) with 1,2,4-trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 400 μL was used with a nominal polymer concentration of 1.0 mg/mL. Dissolution of the sample in stabilized TCB was carried out by heating at 150° C. for about 5 hours with occasional, gentle agitation. The columns used were three PLgel 20 m Mixed A LS columns (7.5×300 mm) and were calibrated with the integral method using a broad linear polyethylene standard (Chevron Phillips Chemical Company Marlex® BHB 5003 polyethylene) for which the molecular weight distribution had been determined. An IR4 detector (Polymer Char, Spain) was used for the concentration detection.

A PLS2 calibration curve was generated using Pirouette chemometric software (Infometrix) to correlate the polymer microstructure obtained by GPC] to the melt fracture behavior as determined by capillary rheometry. A four component calibration model was calculated and optimized using the process of cross validation. The calibration model was verified using a cross-validation approach.

Example 1

Figure 2:
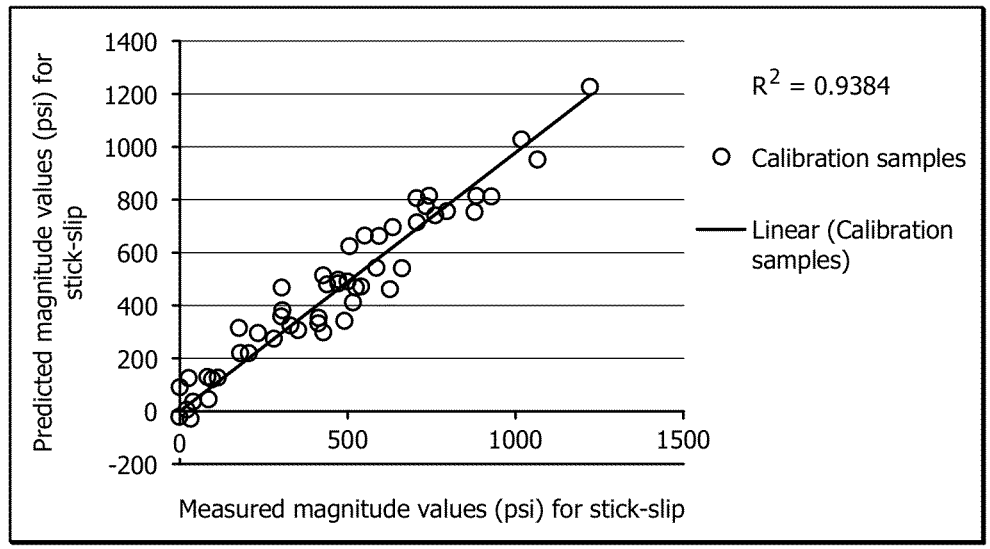
FIG. 2 is a plot of the predicted slip-stick values as a function of the measured slip-stick values for the calibration samples from Example 1.
Figure 3:
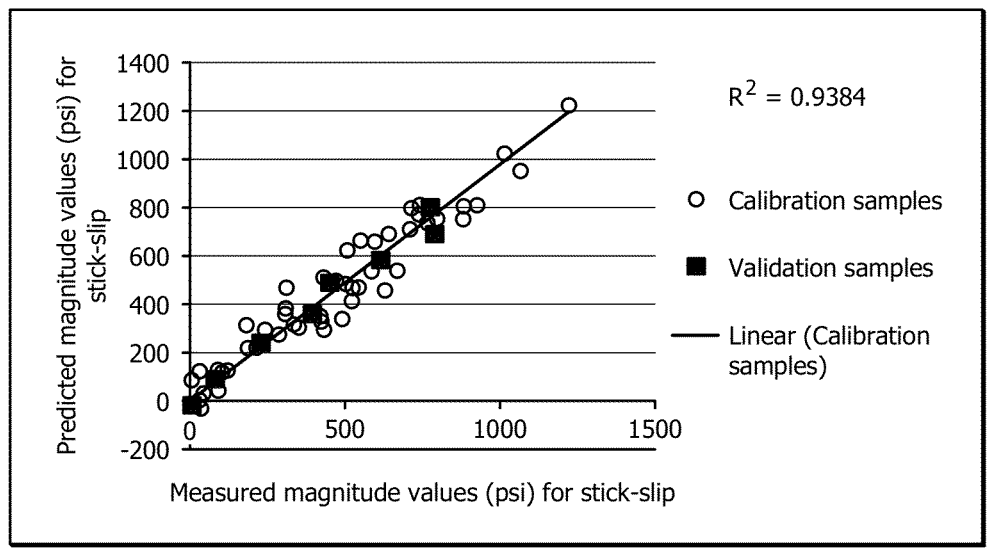
FIG. 3 is a plot of the predicted slip-stick values as a function of the measured slip-stick values for the calibration and validation samples from Example 1.

PLS analysis of the MWD data of various metallocene polyethylenes (M-PE) and Ziegler-Natta polyethylenes (ZN-PE) provided a predicted melt fracture characteristic (Y) which was compared to the measured characteristic. Table 1 provides data on the predicted and measured slip-stick values (psi) (Y=slip-stick value) for 55 polyethylene samples while FIG. 2 is a graphical representation of a calibration curve prepared from the data in Table 1. The slip-stick values of nine polyethylene samples were predicted using the calibration curve of FIG. 2 and the results are presented in Table 2. FIG. 3 is plot of the predicted magnitude values (psi) for slip-stick as a function of the measured magnitude values (psi) for slip-stick for both the calibration samples and validation samples. In addition to the predicted and measured values of Y, each table provides conventional measures of the statistical significance of the data in the form of the Mahalanobis distance, F ratio, probability and leverage. These samples were used to validate the calibration training set.

Figure 4:
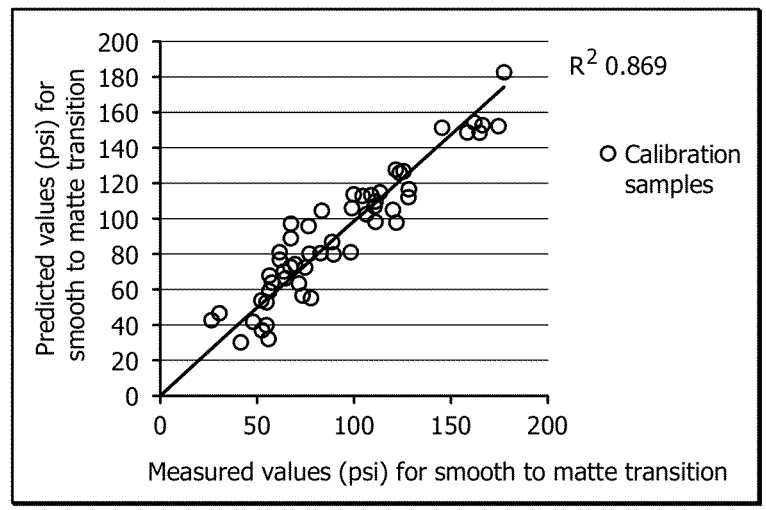
FIG. 4 is a plot of the predicted onset for smooth to matte transition as a function of the measured onset for smooth to matte transition for the calibration samples from Example 1.
Figure 5:
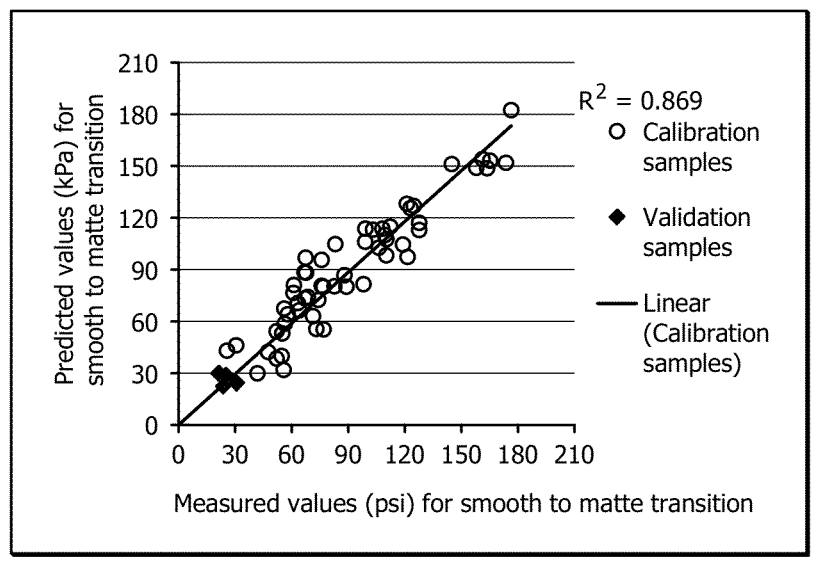
FIG. 5 is a plot of the predicted onset for smooth to matte transition as a function of the measured onset for smooth to matte transition for the calibration and validation samples from Example 1.
Figure 6:
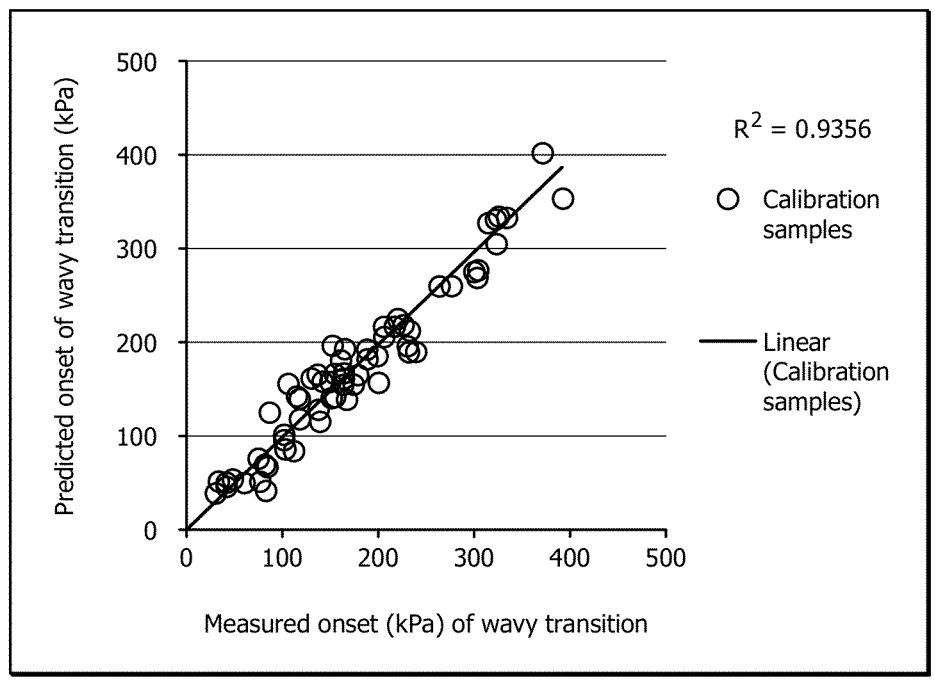
FIG. 6 is a plot of the predicted onset for the matte to wavy transition as a function of the measured onset for the matte to wavy transition for the calibration samples from Example 1.

Table 3 provides data on the predicted and measured values in kiloPascal (kPa) for the smooth to matte transition (Y=smooth to matte transition) for 55 polyethylene samples while FIG. 4 is a graphical representation of a calibration curve prepared from the data in Table 3. The values for the smooth to matte transition for several polyethylene samples were predicted using the calibration curve of FIG. 4 and the results are presented in Tables 4-6. These samples were used to validate the calibration training set. FIG. 4 is plot of the predicted magnitude values (kPa) for the smooth to matte transition as a function of the measured magnitude values (kPa) for the smooth to matte transition for the calibration samples. FIG. 5 is a plot of the predicted magnitude values (kPa) for smooth to matte transition as a function of the measured magnitude values (kPa) for the smooth to matte transition for both the calibration samples and validation samples. FIG. 6 is a plot of the predicted magnitude values (kPa) for the onset of wavy transition as a function of the measured magnitude values (kPa) for the onset of wavy transition for the calibration samples.

TABLE 1

| Sample No. | Cat type. | Structure type | Measured Y | Predicted Y | Residual Y | Upper Limit | Lower Limit | Mahalanobis Distance | F Ratio | Probability | Leverage |
|---|---|---|---|---|---|---|---|---|---|---|---|
| 1 | M-PE | BM | 0 | 88 | −88 | 253 | −77 | 4.689452 | 0.633723 | 0.570243 | 0.086842 |
| 2 | M-PE | BM | 0 | −28 | 28 | 139 | −194 | 5.800618 | 0.835267 | 0.63486 | 0.107419 |
| 3 | M-PE | BM | 0 | −26 | 26 | 136 | −188 | 2.633439 | 0.741116 | 0.606587 | 0.048767 |
| 4 | M-PE | BM | 0 | −17 | 17 | 157 | −191 | 11.267695 | 2.460193 | 0.876928 | 0.208661 |
| 5 | M-PE | BM | 0 | −16 | 16 | 150 | −183 | 5.725693 | 1.174878 | 0.7164 | 0.106031 |
| 6 | M-PE | BM | 23 | 9 | 14 | 170 | −152 | 1.923788 | 0.193044 | 0.337712 | 0.035626 |
| 7 | M-PE | BM | 26 | 125 | −99 | 290 | −40 | 4.577909 | 1.075055 | 0.695205 | 0.084776 |
| 8 | M-PE | BM | 29 | −29 | 58 | 138 | −197 | 6.864896 | 2.990719 | 0.910087 | 0.127128 |
| 9 | M-PE | BM | 39 | 33 | 6 | 201 | −134 | 6.656994 | 0.469325 | 0.503538 | 0.123278 |
| 10 | M-PE | BM | 82 | 129 | −47 | 297 | −38 | 6.340309 | 0.229147 | 0.365756 | 0.117413 |
| 11 | M-PE | BM | 85 | 43 | 42 | 204 | −118 | 1.801648 | 0.440555 | 0.490096 | 0.033364 |
| 12 | M-PE | BM | 96 | 120 | −24 | 283 | −43 | 3.287461 | 0.429704 | 0.484861 | 0.060879 |
| 13 | M-PE | BM | 98 | 124 | −26 | 287 | −39 | 3.52283 | 0.64812 | 0.575402 | 0.065238 |
| 14 | M-PE | TM | 115 | 129 | −14 | 290 | −32 | 2.059048 | 1.0367 | 0.686508 | 0.038131 |
| 15 | M-PE | BM | 177 | 318 | −141 | 481 | 155 | 3.497214 | 0.827687 | 0.632693 | 0.064763 |
| 16 | M-PE | TM | 181 | 221 | −40 | 382 | 59 | 2.273243 | 0.258925 | 0.386902 | 0.042097 |
| 17 | M-PE | TM | 205 | 222 | −17 | 388 | 56 | 5.390471 | 0.663727 | 0.580889 | 0.099824 |
| 18 | M-PE | TM | 235 | 296 | −61 | 457 | 136 | 1.278223 | 1.215226 | 0.724422 | 0.023671 |
| 19 | M-PE | TM | 280 | 278 | 2 | 439 | 118 | 1.522296 | 0.984203 | 0.67406 | 0.028191 |
| 20 | M-PE | TM | 300 | 362 | −62 | 522 | 201 | 1.297488 | 1.053023 | 0.690249 | 0.024028 |
| 21 | M-PE | BM | 302 | 385 | −83 | 561 | 208 | 13.109332 | 0.853596 | 0.640025 | 0.242765 |
| 22 | M-PE | BM | 305 | 470 | −165 | 629 | 311 | 0.628161 | 0.242451 | 0.375403 | 0.011633 |
| 23 | M-PE | TM | 329 | 319 | 10 | 483 | 155 | 4.188392 | 0.271828 | 0.39559 | 0.077563 |
| 24 | M-PE | BM | 346 | 308 | 38 | 475 | 141 | 6.075836 | 1.784714 | 0.812379 | 0.112515 |
| 25 | M-PE | BM | 415 | 333 | 82 | 497 | 168 | 4.458403 | 0.747879 | 0.608721 | 0.082563 |
| 26 | M-PE | TM | 415 | 353 | 62 | 514 | 192 | 1.635425 | 0.142301 | 0.292399 | 0.030286 |
| 27 | M-PE | BM | 424 | 513 | −89 | 673 | 353 | 1.172451 | 2.288236 | 0.863346 | 0.021712 |
| 28 | M-PE | TM | 425 | 299 | 126 | 460 | 138 | 1.718942 | 0.57019 | 0.546274 | 0.031832 |
| 29 | ZN-PE | BM | 440 | 480 | −40 | 640 | 320 | 1.064778 | 0.324859 | 0.428746 | 0.019718 |
| 30 | M-PE | TM | 469 | 486 | −17 | 647 | 325 | 2.041597 | 1.036271 | 0.686409 | 0.037807 |
| 31 | M-PE | BM | 469 | 500 | −31 | 660 | 341 | 0.766478 | 0.316317 | 0.423658 | 0.014194 |
| 32 | M-PE | TM | 485 | 343 | 142 | 503 | 183 | 1.222706 | 0.56069 | 0.542509 | 0.022643 |
| 33 | M-PE | BM | 499 | 488 | 10 | 654 | 323 | 5.17874 | 0.355525 | 0.446308 | 0.095903 |
| 34 | ZN-PE | BM | 503 | 627 | −124 | 791 | 463 | 4.157712 | 0.830472 | 0.633491 | 0.076995 |
| 35 | M-PE | TM | 517 | 415 | 102 | 576 | 254 | 1.824844 | 1.438857 | 0.764022 | 0.033793 |
| 36 | M-PE | TM | 518 | 471 | 47 | 631 | 310 | 1.750413 | 0.309239 | 0.419372 | 0.032415 |
| 37 | M-PE | BM | 537 | 474 | 62 | 640 | 309 | 5.147545 | 0.443338 | 0.491424 | 0.095325 |
| 38 | ZN-PE | BM | 547 | 665 | −118 | 827 | 503 | 2.504622 | 0.990738 | 0.675645 | 0.046382 |
| 39 | ZN-PE | BM | 580 | 538 | 42 | 697 | 379 | 0.317906 | 0.306911 | 0.417948 | 0.005887 |
| 40 | ZN-PE | BM | 590 | 663 | −73 | 825 | 502 | 2.199406 | 0.889679 | 0.6499 | 0.04073 |
| 41 | M-PE | TM | 625 | 462 | 163 | 622 | 302 | 1.120593 | 0.449243 | 0.494221 | 0.020752 |
| 42 | ZN-PE | BM | 634 | 695 | −61 | 856 | 535 | 1.57108 | 1.183749 | 0.718189 | 0.029094 |
| 43 | M-PE | BM | 663 | 539 | 124 | 704 | 375 | 4.274136 | 1.670804 | 0.797908 | 0.079151 |
| 44 | M-PE | BM | 705 | 713 | −9 | 879 | 548 | 5.195957 | 0.228689 | 0.365418 | 0.096221 |
| 45 | M-PE | BM | 707 | 804 | −97 | 972 | 636 | 6.814694 | 1.341158 | 0.747668 | 0.126198 |
| 46 | M-PE | BM | 731 | 778 | −47 | 944 | 611 | 5.682072 | 0.809082 | 0.627296 | 0.105224 |
| 47 | ZN-PE/M-PE | TM | 740 | 814 | −74 | 977 | 651 | 3.360436 | 0.085846 | 0.229261 | 0.06223 |
| 48 | M-PE | BM | 759 | 745 | 14 | 910 | 579 | 5.213402 | 0.524056 | 0.52751 | 0.096545 |
| 49 | M-PE | BM | 790 | 757 | 34 | 921 | 592 | 4.548491 | 0.367159 | 0.452702 | 0.084231 |
| 50 | ZN-PE | BM | 875 | 755 | 120 | 916 | 595 | 1.876904 | 1.482164 | 0.770849 | 0.034757 |
| 51 | ZN-PE/M-PE | TM | 879 | 810 | 69 | 973 | 648 | 3.194673 | 0.171523 | 0.319467 | 0.059161 |
| 52 | ZN-PE/M-PE | TM | 920 | 813 | 108 | 976 | 650 | 3.257771 | 0.130208 | 0.280263 | 0.060329 |
| 53 | ZN-PE/M-PE | TM | 1011 | 1026 | −14 | 1193 | 858 | 6.690147 | 0.331866 | 0.432853 | 0.123892 |
| 54 | ZN-PE/M-PE | TM | 1062 | 956 | 105 | 1126 | 787 | 7.956915 | 0.705278 | 0.594986 | 0.14735 |
| 55 | M-PE | BM | 1218 | 1227 | −10 | 1402 | 1053 | 11.668286 | 1.841389 | 0.819117 | 0.216079 |

TABLE 2

| Sample No. | Cat type. | Structure type | Measured Y | Predicted Y | Residual Y | Upper Limit | Lower Limit | Mahalanobis Distance | F Ratio | Probability | Leverage |
|---|---|---|---|---|---|---|---|---|---|---|---|
| 56 | M-PE | BM | 0 | −13 | 13 | 156 | −182 | 7.6880 | 2.0368 | 0.8403 | 0.1424 |
| 57 | M-PE | BM | 0 | −16 | 16 | 150 | −183 | 5.7257 | 1.1749 | 0.7164 | 0.1060 |
| 58 | M-PE | BM | 76 | 94 | −19 | 261 | −73 | 6.2220 | 0.5418 | 0.5349 | 0.1152 |
| 59 | M-PE | TM | 224 | 245 | −21 | 406 | 84 | 1.9931 | 0.1997 | 0.3431 | 0.0369 |
| 60 | M-PE | BM | 389 | 363 | 26 | 528 | 197 | 4.9512 | 0.8698 | 0.6445 | 0.0917 |
| 61 | ZN-PE | BM | 445 | 489 | −44 | 648 | 329 | 0.9934 | 0.4117 | 0.4760 | 0.0184 |
| 62 | M-PE | BM | 610 | 585 | 25 | 747 | 424 | 2.3449 | 1.0511 | 0.6898 | 0.0434 |
| 63 | M-PE | BM | 771 | 805 | −34 | 973 | 636 | 7.0441 | 1.7967 | 0.8138 | 0.1304 |
| 64 | ZN-PE | BM | 785 | 692 | 93 | 853 | 531 | 1.9709 | 0.6158 | 0.5637 | 0.0365 |

TABLE 3

| Sample No. | Cat type. | Structure type | Measured Y (kPa) | Predicted Y (kPa) | Residual Y (kPa) | 95% CL Upper Limit (kPa) | 95% CL Lower Limit (kPa) | Mahalanobis Distance | F Ratio | Probability | Leverage |
|---|---|---|---|---|---|---|---|---|---|---|---|
| 65 | M-PE | BM | 26 | 43 | −17 | 70 | 15 | 5.28302 | 0.60381 | 0.559417 | 0.09434 |
| 66 | M-PE | BM | 30 | 46 | −16 | 73 | 19 | 2.703169 | 3.544509 | 0.934763 | 0.048271 |
| 67 | M-PE | BM | 41 | 30 | 11 | 58 | 2 | 6.791506 | 0.674373 | 0.58479 | 0.121277 |
| 68 | M-PE | BM | 47 | 42 | 5 | 69 | 15 | 2.04752 | 0.21828 | 0.357731 | 0.036563 |
| 69 | M-PE | BM | 52 | 54 | −2 | 82 | 26 | 4.292444 | 1.905774 | 0.826772 | 0.076651 |
| 70 | M-PE | BM | 52 | 38 | 14 | 65 | 10 | 3.331579 | 0.99675 | 0.677365 | 0.059492 |
| 71 | M-PE | BM | 54 | 40 | 14 | 67 | 13 | 2.209805 | 0.063193 | 0.197509 | 0.039461 |
| 72 | M-PE | TM | 54 | 53 | 1 | 80 | 26 | 1.938798 | 0.871222 | 0.64515 | 0.034621 |
| 73 | M-PE | BM | 55 | 32 | 23 | 60 | 5 | 2.820709 | 0.170083 | 0.318298 | 0.05037 |
| 74 | M-PE | BM | 56 | 59 | −3 | 87 | 31 | 5.889243 | 0.878045 | 0.647012 | 0.105165 |
| 75 | M-PE | BM | 56 | 68 | −12 | 95 | 41 | 2.342684 | 1.210574 | 0.723809 | 0.041834 |
| 76 | M-PE | TM | 57 | 64 | −7 | 91 | 37 | 2.000884 | 0.347987 | 0.442239 | 0.03573 |
| 77 | M-PE | TM | 61 | 81 | −20 | 108 | 54 | 1.083685 | 0.492962 | 0.514319 | 0.019352 |
| 78 | M-PE | TM | 61 | 77 | −16 | 104 | 50 | 1.602323 | 0.437354 | 0.488733 | 0.028613 |
| 79 | M-PE | BM | 63 | 70 | −7 | 98 | 43 | 2.992918 | 3.138032 | 0.917765 | 0.053445 |
| 80 | M-PE | TM | 64 | 66 | −2 | 93 | 39 | 1.210406 | 0.848122 | 0.638743 | 0.021614 |
| 81 | M-PE | BM | 67 | 89 | −22 | 116 | 61 | 4.573915 | 1.435869 | 0.76386 | 0.081677 |
| 82 | M-PE | BM | 67 | 89 | −22 | 117 | 61 | 4.189096 | 0.565609 | 0.544664 | 0.074805 |
| 83 | M-PE | TM | 67 | 73 | −6 | 100 | 46 | 1.356554 | 0.496362 | 0.515812 | 0.024224 |
| 84 | ZN-PE | BM | 67 | 97 | −30 | 124 | 71 | 0.109069 | 0.124188 | 0.274066 | 0.001948 |
| 85 | M-PE | BM | 69 | 74 | −5 | 102 | 47 | 2.373091 | 3.201317 | 0.920706 | 0.042377 |
| 86 | M-PE | TM | 71 | 63 | 8 | 90 | 36 | 1.078215 | 0.910404 | 0.655661 | 0.019254 |
| 87 | M-PE | TM | 73 | 57 | 16 | 84 | 30 | 1.915975 | 0.474808 | 0.506211 | 0.034214 |
| 88 | M-PE | TM | 74 | 72 | 2 | 99 | 46 | 1.092725 | 0.523947 | 0.527654 | 0.019513 |
| 89 | M-PE | TM | 76 | 81 | −5 | 107 | 54 | 0.881971 | 0.871174 | 0.645137 | 0.015749 |
| 90 | M-PE | BM | 76 | 96 | −20 | 122 | 69 | 0.295858 | 1.400256 | 0.758039 | 0.005283 |
| 91 | M-PE | TM | 77 | 55 | 22 | 82 | 28 | 2.559104 | 2.04462 | 0.841386 | 0.045698 |
| 92 | M-PE | TM | 77 | 80 | −3 | 107 | 53 | 1.272153 | 1.285069 | 0.73794 | 0.022717 |
| 93 | M-PE | BM | 82 | 81 | 1 | 108 | 53 | 2.981837 | 0.206155 | 0.348348 | 0.053247 |
| 94 | ZN-PE | BM | 83 | 105 | −22 | 132 | 78 | 1.942585 | 1.262393 | 0.733738 | 0.034689 |
| 95 | M-PE | BM | 88 | 87 | 1 | 113 | 60 | 0.35911 | 1.416235 | 0.760672 | 0.006413 |
| 96 | M-PE | TM | 89 | 80 | 9 | 107 | 53 | 0.894821 | 0.874843 | 0.64614 | 0.015979 |
| 97 | M-PE | BM | 98 | 81 | 17 | 109 | 54 | 3.877832 | 0.222874 | 0.361203 | 0.069247 |
| 98 | ZN-PE | BM | 99 | 106 | −7 | 133 | 79 | 1.446633 | 0.767448 | 0.615039 | 0.025833 |
| 99 | M-PE | BM | 100 | 114 | −14 | 141 | 86 | 4.174528 | 2.378543 | 0.871038 | 0.074545 |
| 100 | ZN-PE | BM | 104 | 113 | −9 | 140 | 86 | 0.799369 | 1.105997 | 0.702275 | 0.014274 |
| 101 | M-PE | BM | 106 | 102 | 4 | 132 | 73 | 12.342955 | 0.444051 | 0.491936 | 0.22041 |
| 102 | M-PE | BM | 108 | 114 | −6 | 141 | 86 | 4.454492 | 0.779766 | 0.618799 | 0.079545 |
| 103 | ZN-PE | BM | 110 | 110 | 0 | 136 | 83 | 0.949288 | 0.526221 | 0.528609 | 0.016952 |
| 104 | ZN-PE | BM | 110 | 108 | 2 | 135 | 81 | 1.241156 | 0.488042 | 0.512144 | 0.022163 |
| 105 | ZN-PE | BM | 110 | 107 | 3 | 134 | 81 | 1.12129 | 0.436844 | 0.488487 | 0.020023 |
| 106 | M-PE | BM | 110 | 98 | 12 | 126 | 71 | 3.647568 | 0.588353 | 0.55354 | 0.065135 |
| 107 | M-PE | BM | 113 | 115 | −2 | 143 | 88 | 4.201627 | 1.382741 | 0.75511 | 0.075029 |
| 108 | M-PE | BM | 120 | 105 | 15 | 132 | 77 | 3.490929 | 0.811559 | 0.628265 | 0.062338 |
| 109 | ZN-PE/M-PE | TM | 121 | 128 | −7 | 154 | 101 | 1.465725 | 0.091316 | 0.236306 | 0.026174 |
| 110 | M-PE | BM | 121 | 98 | 24 | 125 | 70 | 3.35217 | 0.587111 | 0.553062 | 0.05986 |
| 111 | ZN-PE/M-PE | TM | 123 | 126 | −3 | 153 | 99 | 1.524436 | 0.077956 | 0.218827 | 0.027222 |
| 112 | ZN-PE/M-PE | TM | 125 | 127 | −2 | 154 | 100 | 1.587229 | 0.067539 | 0.204038 | 0.028343 |
| 113 | M-PE | BM | 128 | 117 | 11 | 144 | 89 | 4.179567 | 0.307286 | 0.418318 | 0.074635 |
| 114 | M-PE | BM | 128 | 112 | 16 | 140 | 85 | 3.750068 | 2.928592 | 0.907129 | 0.066966 |
| 115 | ZN-PE/M-PE | TM | 145 | 151 | −6 | 179 | 124 | 3.673731 | 0.130649 | 0.280803 | 0.065602 |
| 116 | ZN-PE/M-PE | TM | 158 | 149 | 9 | 176 | 121 | 3.22575 | 0.17626 | 0.323696 | 0.057603 |
| 117 | ZN-PE/M-PE | TM | 162 | 154 | 8 | 182 | 126 | 5.568025 | 0.263315 | 0.390016 | 0.099429 |
| 118 | ZN-PE/M-PE | TM | 164 | 149 | 15 | 177 | 122 | 3.470207 | 0.203697 | 0.346405 | 0.061968 |
| 119 | ZN-PE/M-PE | TM | 166 | 153 | 13 | 181 | 125 | 5.457026 | 0.214731 | 0.355018 | 0.097447 |
| 120 | ZN-PE/M-PE | TM | 174 | 152 | 22 | 180 | 125 | 5.088583 | 0.358921 | 0.448342 | 0.090868 |
| 121 | M-PE | BM | 177 | 183 | −6 | 211 | 155 | 7.493027 | 0.616065 | 0.563992 | 0.133804 |

TABLE 4

| | Cat type. | Structure type | Measured Y (kPa) | Predicted Y (kPa) | Residual Y (kPa) | 95% CL Upper Limit (kPa) | 95% CL Lower Limit (kPa) | Mahalanobis Distance | F Ratio | Probability | Leverage |
|---|---|---|---|---|---|---|---|---|---|---|---|
| 112 | M-PE | BM | 24 | 23 | 1 | 51 | −5 | 5.982789 | 1.99459 | 0.836293 | 0.106836 |
| 113 | M-PE | BM | 21 | 30 | −9 | 59 | 1 | 9.041662 | 3.48069 | 0.932372 | 0.161458 |
| 114 | M-PE | BM | 25 | 28 | −3 | 56 | −1 | 8.167974 | 2.390947 | 0.872009 | 0.145857 |
| 115 | M-PE | BM | 30 | 24 | 6 | 53 | −4 | 7.772788 | 1.569992 | 0.784292 | 0.1388 |

TABLE 5

| Pipe Resins | Measured Y (kPa) | Predicted Y (kPa) | 95% CL Upper Limit | 95% CL Lower Limit | Observed SS-MF | PPA |
|---|---|---|---|---|---|---|
| C1 | 48 | 55 | 82 | 27 | yes | yes |
| C2 | 44 | 45 | 72 | 18 | yes | yes |
| C3 | 44 | 45 | 72 | 18 | yes | yes |
| C4 | 82 | 64 | 18 | 114 | NA | no |
| C5 | NA | 69 | 96 | 41 | yes | yes |
| C6 | NA | 89 | 116 | 62 | NA | no |
| C7 | NA | 89 | 116 | 62 | yes | yes |
| I1 | 108 | 116 | 143 | 88 | NA | no |
| I2 | NA | 116 | 144 | 88 | no | no |
| I3 | NA | 116 | 144 | 88 | no | yes |

TABLE 6

| Pipe Resins | Measured Y (kPa) | Measured shear rate (1/s) | Observed SS-MF | PPA |
|---|---|---|---|---|
| C1 | 48 | 16 | yes | yes |
| C2 | 44 | 17 | yes | yes |
| C3 | 47 | 2.5 | NA | no |
| C4 | 44 | 11 | yes | yes |
| C5 | NA | NA | yes | yes |
| C6 | NA | NA | yes | yes |
| C7 | NA | NA | yes | yes |
| I1 | 108 | 26 | NA | no |
| I2 | NA | NA | no | yes |
| I3 | NA | NA | no | yes |

Example 2

Figure 8:
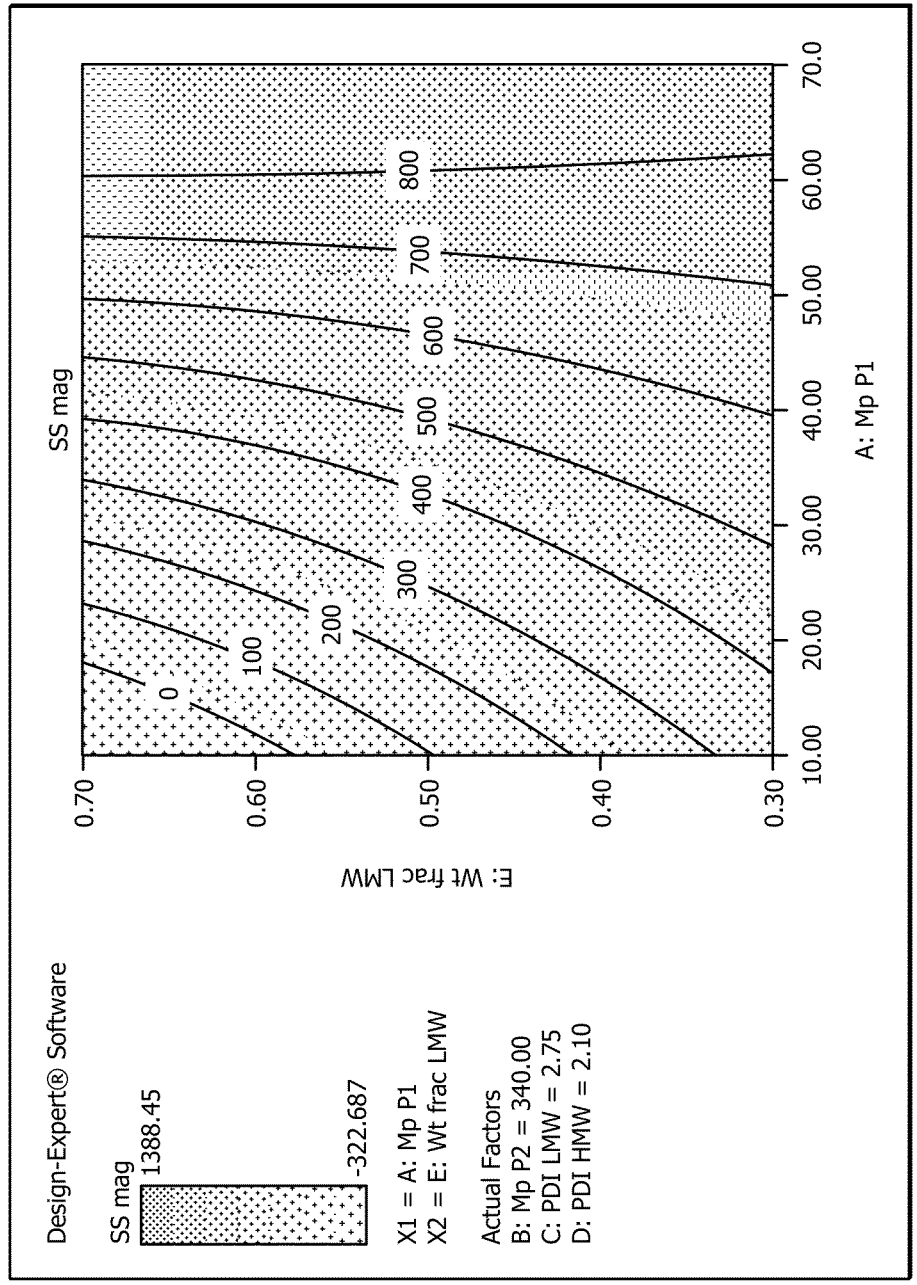
FIG. 8 is a FIG. 8 is a plot of the magnitude of slip-stick as a function of the weight fraction of the lower molecular weight (LMW) component and the peak molecular weight.

Using two Gaussian peak shapes, various MWD profiles were digitally generated by varying six parameters, the Mp, PDI and weight fraction of peak 1 (P1) and Mp, PDI and weight fraction of peak 2 (P2). P1 is also referred to as the lower molecular weight (LMW) component while P2 is also referred to as the higher molecular weight (HMW) component. Recognizing that if the area under the MWD distribution is equal to unity (i.e., 1) and is described by two component peaks, the number of variables can be reduced to five, where the weight fraction composition of peak 2 can be written in terms of the weight fraction of peak 1 (i.e., wt frac. p2=1-wt frac. p1). These parameters are illustrated in FIG. 8. To explore the influence of these five parameters on the magnitude of slip-stick as predicted as from the above PLS2 method, a DOE of the five parameters was generated as below in Table 7. Also appearing in Table 7 are the $M_w$, $M_n$ and PDI of the results MWD profile obtained by the combination of the two components as well as the values for the predicted magnitude of the slip-stick generated from the analysis of the resulting MWD profile using the PLS2 model.

TABLE 7

| Std Order | Run | Mp P1 | Mp P2 | PDI P1 | PDI P2 | Wt Frac P1 | Magnitude Slip-stick | Matte | Mw P1 | Mw P2 | Mn P1 | Mn P2 | Blend Mw kg/mol | Blend Mn kg/mol | Blend PDI |
|---|---|---|---|---|---|---|---|---|---|---|---|---|---|---|---|
| 21 | 1 | 63.24555 | 94.86833 | 2.5 | 2.5 | 0.3 | 1388 | 189 | 100 | 150 | 40 | 60 | 135 | 52 | 2.5875 |
| 25 | 2 | 11.18034 | 505.9644 | 5 | 2.5 | 0.3 | 167 | 36 | 25 | 800 | 5 | 320 | 568 | 16 | 35.29141 |
| 27 | 3 | 32.27486 | 245.2889 | 3.75 | 3.75 | 0.5 | 645 | 116 | 63 | 475 | 17 | 127 | 269 | 29 | 9.123355 |
| 19 | 4 | 11.18034 | 212.4265 | 5 | 5 | 0.3 | 629 | 107 | 25 | 475 | 5 | 95 | 340 | 15 | 22.90526 |
| 10 | 5 | 32.27486 | 245.2889 | 3.75 | 3.75 | 0.5 | 562 | 130 | 63 | 475 | 17 | 127 | 269 | 29 | 9.123355 |
| 31 | 6 | 12.90994 | 67.08204 | 3.75 | 5 | 0.3 | 583 | 115 | 25 | 150 | 7 | 30 | 113 | 15 | 7.6875 |
| 28 | 7 | 15.81139 | 413.1182 | 2.5 | 3.75 | 0.7 | −323 | 24 | 25 | 800 | 10 | 213 | 258 | 14 | 18.38711 |
| 14 | 8 | 44.72136 | 505.9644 | 5 | 2.5 | 0.3 | 428 | 65 | 100 | 800 | 20 | 320 | 590 | 58 | 10.14063 |
| 20 | 9 | 27.95085 | 357.7709 | 5 | 5 | 0.3 | 560 | 93 | 63 | 800 | 13 | 160 | 579 | 35 | 16.42203 |
| 7 | 10 | 63.24555 | 505.9644 | 2.5 | 2.5 | 0.7 | 580 | 101 | 100 | 800 | 40 | 320 | 310 | 54 | 5.715625 |
| 9 | 11 | 63.24555 | 67.08204 | 2.5 | 5 | 0.7 | 1179 | 170 | 100 | 150 | 40 | 30 | 115 | 36 | 3.1625 |
| 29 | 12 | 11.18034 | 212.4265 | 5 | 5 | 0.3 | 712 | 93 | 25 | 475 | 5 | 95 | 340 | 15 | 22.90526 |
| 11 | 13 | 11.18034 | 94.86833 | 5 | 2.5 | 0.3 | 1097 | 162 | 25 | 150 | 5 | 60 | 113 | 14 | 8.0625 |
| 26 | 14 | 63.24555 | 67.08204 | 2.5 | 5 | 0.3 | 1041 | 158 | 100 | 150 | 40 | 30 | 135 | 32 | 4.1625 |
| 17 | 15 | 15.81139 | 94.86833 | 2.5 | 2.5 | 0.7 | 74 | 70 | 25 | 150 | 10 | 60 | 63 | 13 | 4.6875 |
| 23 | 16 | 63.24555 | 505.9644 | 2.5 | 2.5 | 0.3 | 428 | 65 | 100 | 800 | 40 | 320 | 590 | 103 | 5.715625 |
| 8 | 17 | 63.24555 | 357.7709 | 2.5 | 5 | 0.3 | 899 | 125 | 100 | 800 | 40 | 160 | 590 | 84 | 7.00625 |
| 12 | 18 | 12.90994 | 67.08204 | 3.75 | 5 | 0.3 | 666 | 102 | 25 | 150 | 7 | 30 | 113 | 15 | 7.6875 |
| 22 | 19 | 15.81139 | 94.86833 | 2.5 | 2.5 | 0.3 | 927 | 149 | 25 | 150 | 10 | 60 | 113 | 24 | 4.6875 |
| 13 | 20 | 11.18034 | 505.9644 | 5 | 2.5 | 0.7 | −65 | 32 | 25 | 800 | 5 | 320 | 258 | 7 | 36.29141 |
| 15 | 21 | 44.72136 | 67.08204 | 5 | 5 | 0.3 | 851 | 142 | 100 | 150 | 20 | 30 | 135 | 26 | 5.175 |
| 32 | 22 | 31.62278 | 260.8746 | 2.5 | 5 | 0.7 | 459 | 104 | 50 | 583 | 20 | 117 | 210 | 27 | 7.89 |
| 3 | 23 | 44.72136 | 94.86833 | 5 | 2.5 | 0.7 | 935 | 149 | 100 | 150 | 20 | 60 | 115 | 25 | 4.6 |
| 6 | 24 | 44.72136 | 357.7709 | 5 | 5 | 0.7 | 687 | 119 | 100 | 800 | 20 | 160 | 310 | 27 | 11.43125 |
| 2 | 25 | 15.81139 | 413.1182 | 2.5 | 3.75 | 0.7 | −240 | 10 | 25 | 800 | 10 | 213 | 258 | 14 | 18.38711 |
| 24 | 26 | 44.72136 | 94.86833 | 5 | 2.5 | 0.3 | 1241 | 177 | 100 | 150 | 20 | 60 | 135 | 38 | 3.6 |
| 4 | 27 | 11.18034 | 67.08204 | 5 | 5 | 0.7 | 203 | 75 | 25 | 150 | 5 | 30 | 63 | 7 | 9.375 |
| 30 | 28 | 27.95085 | 357.7709 | 5 | 5 | 0.3 | 477 | 107 | 63 | 800 | 13 | 160 | 579 | 35 | 16.42203 |
| 16 | 29 | 15.81139 | 67.08204 | 2.5 | 5 | 0.5 | 171 | 79 | 25 | 150 | 10 | 30 | 88 | 15 | 5.833333 |
| 18 | 30 | 31.62278 | 260.8746 | 2.5 | 5 | 0.7 | 376 | 118 | 50 | 583 | 20 | 117 | 210 | 27 | 7.89 |
| 5 | 31 | 15.81139 | 505.9644 | 2.5 | 2.5 | 0.3 | 4 | 25 | 25 | 800 | 10 | 320 | 568 | 31 | 18.26641 |
| 1 | 32 | 12.24745 | 357.7709 | 4.166667 | 5 | 0.566666667 | 99 | 54 | 25 | 800 | 6 | 160 | 361 | 10 | 35.05596 |

An analysis of variance (ANOVA) was carried out on the values calculated from the PLS2 data for the slip-stick melt fracture and the results are given in Tables 8, 9, and 110.

TABLE 8

| Source | Sum of Squares | df | Mean Square | F Value | p-value Prob > F |
|---|---|---|---|---|---|
| Model | 5527071 | 15 | 368471.4164 | 36.91696 | <0.0001 |
| A-Mp P1 | 1600828 | 1 | 1600827.965 | 160.3861 | <0.0001 |
| B-Mp P2 | 783015.4 | 1 | 783015.3965 | 78.4499 | <0.0001 |
| C-PDI LMW | 97880.79 | 1 | 97880.79312 | 9.806625 | 0.0064 |
| D-PDI HMW | 428.771 | 1 | 428.7710289 | 0.042958 | 0.8384 |
| E-Wt frac LMW | 175349.7 | 1 | 175349.7336 | 17.5682 | 0.0007 |
| AB | 85.06823 | 1 | 85.06823224 | 0.008523 | 0.9276 |
| AC | 132153 | 1 | 132152.9765 | 13.24034 | 0.0022 |
| AD | 6772.471 | 1 | 6772.470625 | 0.67853 | 0.4222 |
| AE | 357916.6 | 1 | 357916.5942 | 35.85947 | <0.0001 |
| BC | 403.4945 | 1 | 403.4944702 | 0.040426 | 0.8432 |
| BD | 293699.2 | 1 | 293699.1753 | 29.42556 | <0.0001 |
| BE | 78878.29 | 1 | 78878.29386 | 7.902774 | 0.0125 |
| CD | 7930.625 | 1 | 7930.625265 | 0.794565 | 0.3859 |
| CE | 14450.72 | 1 | 14450.72244 | 1.44781 | 0.2464 |
| DE | 72350.18 | 1 | 72350.18158 | 7.248726 | 0.0160 |
| Residual | 159697.4 | 16 | 9981.089078 | | |
| Lack of Fit | 129697.4 | 10 | 12969.74253 | 2.593949 | 0.1278 |
| Pure Error | 30000 | 6 | 5000 | | |
| Cor Total | 5686769 | 31 | | | |

The Model F-value of 36.92 implies the model is significant. There is only a 0.01% chance that a "Model F-Value" this large could occur due to noise. Further, the values of "Prob>F" less than 0.0500 indicate model terms are significant The results demonstrate that in this case A, B, C, E, AC, AE, BD, BE, DE are significant model terms as values greater than 0.1000 indicate the model terms are not significant. A better model can be obtained by removing insignificant model terms (not counting those required to support hierarchy), in order to demonstrate the influence of all the terms. The "Lack of Fit F-value" of 2.59 implies the Lack of Fit is not significant relative to the pure error. There is a 12.78% chance that a "Lack of Fit F-value" this large could occur due to noise. Further statistical evaluation provided the following:

TABLE 9

| Std. Dev. | 99.9054 | R-Squared | 0.971918 |
|---|---|---|---|
| Mean | 545.1094 | Adj R-Squared | 0.945591 |
| C.V. % | 18.32759 | Pred R-Squared | 0.87355 |
| PRESS | 719089.8 | Adeq Precision | 22.77148 |

The "Pred R-Squared" of 0.8736 is in reasonable agreement with the "Adj R-Squared" of 0.9456. This value improves to 0.9277 with insignificant terms removed. "Adeq Precision" is a measure of the signal to noise ratio. A ratio greater than 4 is desirable. The observed ratio of 22.771 indicates an adequate signal suggesting this model can be used to navigate the design space.

TABLE 10

| Factor | Coefficient Estimate | df | Standard Error | 95% CI Low | 95% CI High | VIF |
|---|---|---|---|---|---|---|
| Intercept | 593.1529 | 1 | 22.40955147 | 545.6468 | 640.659 | |
| A-Mp P1 | 364.2112 | 1 | 28.75874163 | 303.2453 | 425.177 | 1.461032 |
| B-Mp P2 | −249.026 | 1 | 28.11571834 | −308.629 | −189.424 | 1.456545 |
| C-PDI LMW | 73.14195 | 1 | 23.35644523 | 23.6285 | 122.6554 | 1.481018 |
| D-PDI HMW | −4.69935 | 1 | 22.67325858 | −52.7645 | 43.36581 | 1.416389 |
| E-Wt frac LMW | −89.574 | 1 | 21.37068513 | −134.878 | −44.2702 | 1.240368 |
| AB | −3.07806 | 1 | 33.34130335 | −73.7585 | 67.60234 | 1.536049 |
| AC | −108.375 | 1 | 29.78381408 | −171.514 | −45.2363 | 1.395963 |
| AD | 24.59074 | 1 | 29.85292932 | −38.6946 | 87.87612 | 1.599554 |
| AE | 166.8858 | 1 | 27.86874874 | 107.8067 | 225.9649 | 1.398294 |
| BC | 5.444599 | 1 | 27.07921396 | −51.9608 | 62.84997 | 1.24382 |
| BD | 152.3825 | 1 | 28.09134774 | 92.83146 | 211.9335 | 1.328869 |
| BE | 74.52588 | 1 | 26.51046512 | 18.32621 | 130.7256 | 1.245329 |
| CD | −20.955 | 1 | 23.50841841 | −70.7906 | 28.8806 | 1.387308 |
| CE | 27.04579 | 1 | 22.47728138 | −20.6039 | 74.69549 | 1.261851 |
| DE | 59.39209 | 1 | 22.05960613 | 12.62781 | 106.1564 | 1.272873 |

The sign of the coefficient estimate indicated the magnitude of influence and direction of effect for the particular parameter or combination of parameters. For example increasing the $M_p$ P1, increased the slip-stick magnitude while increasing the $M_p$ of P2 decreased the slip-stick magnitude (greater MW difference between components, therefore less overlap).

The analysis of the variance was recalculated omitting runs 7, 15, 25, and 29 in the analysis. These runs were omitted because the chemometric model identified these runs as outliers with a probability greater than the cutoff of 0.999. The results of this second ANOVA analysis are presented in Tables 11-13.

TABLE 11

ANOVA for Response Surface 2FI Model
Analysis of variance table [Partial sum of squares - Type III]

| Source | Sum of Squares | df | Mean Square | F Value | p-value Prob > F |
|---|---|---|---|---|---|
| Model | 3646082 | 15 | 243072.1025 | 41.75056 | <0.0001 |
| A-Mp P1 | 895118.2 | 1 | 895118.2205 | 153.7473 | <0.0001 |
| B-Mp P2 | 600640.3 | 1 | 600640.3064 | 103.1672 | <0.0001 |
| C-PDI P1 | 21689.74 | 1 | 21689.73544 | 3.725473 | 0.0776 |
| D-PDI P2 | 5012.122 | 1 | 5012.121606 | 0.860892 | 0.3718 |
| E-Wt frac P1 | 115814 | 1 | 115814.024 | 19.89245 | 0.0008 |
| AB | 1790.978 | 1 | 1790.978376 | 0.307622 | 0.5893 |
| AC | 57380.55 | 1 | 57380.54663 | 9.855799 | 0.0085 |
| AD | 4863.659 | 1 | 4863.658861 | 0.835392 | 0.3787 |
| AE | 110499.6 | 1 | 110499.6017 | 18.97963 | 0.0009 |
| BC | 4646.01 | 1 | 4646.009525 | 0.798008 | 0.3893 |
| BD | 240247.8 | 1 | 240247.8178 | 41.26545 | <0.0001 |
| BE | 36791.94 | 1 | 36791.93615 | 6.319457 | 0.0272 |
| CD | 2766.34 | 1 | 2766.340376 | 0.475152 | 0.5037 |
| CE | 3.189822 | 1 | 3.189821631 | 0.000548 | 0.9817 |
| DE | 12859.12 | 1 | 12859.11567 | 2.208708 | 0.1630 |
| Residual | 69864.11 | 12 | 5822.008807 | | |
| Lack of Fit | 52641.61 | 7 | 7520.229384 | 2.183257 | 0.2035 |
| Pure Error | 17222.5 | 5 | 3444.5 | | |
| Cor Total | 3715946 | 27 | | | |

The Model F-value of 41.75 implies the model is significant. There is only a 0.01% chance that a "Model F-Value" this large could occur due to noise. Values of "Prob>F" less than 0.0500 indicate model terms are significant. In this case A, B, E, AC, AE, BD, BE are significant model terms. Values greater than 0.1000 indicate the model terms are not significant. The "Lack of Fit F-value" of 2.18 implies the Lack of Fit is not significant relative to the pure error. There is a 20.35% chance that a "Lack of Fit F-value" this large could occur due to noise.

TABLE 12

| Std. Dev. | 76.30209 | R-Squared | 0.981199 |
|---|---|---|---|
| Mean | 634.3231 | Adj R-Squared | 0.957697 |
| C.V. % | 12.0289 | Pred R-Squared | 0.830489 |
| PRESS | 629894.2 | Adeq Precision | 25.6499 |

The "Pred R-Squared" of 0.8305 is in reasonable agreement with the "Adj R-Squared" of 0.9577. "Adeq Precision" measures the signal to noise ratio. A ratio greater than 4 is desirable. The ratio of 25.650 indicates an adequate signal. This model can be used to navigate the design space.

TABLE 13

| Factor | Coefficient Estimate | df | Standard Error | 95% CI Low | 95% CI High | VIF |
|---|---|---|---|---|---|---|
| Intercept | 610.5575 | 1 | 19.66770497 | 567.7052 | 653.4097 | |
| A-Mp P1 | 326.8809 | 1 | 26.36244948 | 269.442 | 384.3197 | 1.922928 |
| B-Mp P2 | −269.068 | 1 | 26.49052347 | −326.785 | −211.35 | 1.939074 |
| C-PDI P1 | 41.86738 | 1 | 21.69127339 | −5.39385 | 89.1286 | 1.835677 |
| D-PDI P2 | −20.6497 | 1 | 22.25555151 | −69.1403 | 27.84103 | 2.163345 |
| E-Wt frac P1 | −81.5786 | 1 | 18.29077861 | −121.431 | −41.7264 | 1.288823 |
| AB | 16.49979 | 1 | 29.74882271 | −48.3173 | 81.31691 | 1.853276 |
| AC | −78.4567 | 1 | 24.99101268 | −132.907 | −24.0059 | 1.178035 |
| AD | 24.90805 | 1 | 27.25176476 | −34.4684 | 84.28455 | 2.108865 |
| AE | 132.2034 | 1 | 30.34580877 | 66.08557 | 198.3212 | 2.466812 |
| BC | 22.86528 | 1 | 25.59604243 | −32.9037 | 78.63426 | 1.630753 |
| BD | 142.7778 | 1 | 22.22631509 | 94.35085 | 191.2048 | 1.263168 |
| BE | 64.64975 | 1 | 25.71739256 | 8.616362 | 120.6831 | 1.848938 |
| CD | −16.1917 | 1 | 23.48968122 | −67.3714 | 34.98788 | 2.184276 |
| CE | −0.59048 | 1 | 25.22645567 | −55.5542 | 54.37325 | 2.482783 |
| DE | 32.96268 | 1 | 22.17958266 | −15.3625 | 81.28784 | 2.116413 |

The ANOVA analysis identified parameters and combinations of parameters that significantly contribute to the final result (i.e., melt fracture characteristic.) Thus, the following equation for the magnitude of slip-stick was as follows:

Example 3

The influence of the $M_p$, weight fraction, and PDI of each component on the stress for the smooth-matte transition as predicted as from the PLS2 method was investigated as described in Example 2. ANOVA analyses of the results are as given in Tables 14-16.

TABLE 14

ANOVA for Response Surface 2FI Model
Analysis of variance table [Partial sum of squares - Type III]

| Source | Sum of Squares | df | Mean Square | F Value | p-value Prob > F |
|---|---|---|---|---|---|
| Model | 51102.59 | 15 | 3406.839578 | 39.88098 | <0.0001 |
| A-Mp P1 | 7643.991 | 1 | 7643.991138 | 89.48172 | <0.0001 |
| B-Mp P2 | 11607.42 | 1 | 11607.42056 | 135.8782 | <0.0001 |
| C-PDI P1 | 0.031347 | 1 | 0.031346975 | 0.000367 | 0.9850 |
| D-PDI P2 | 68.18712 | 1 | 68.18712105 | 0.798209 | 0.3892 |
| E-Wt frac P1 | 3.847193 | 1 | 3.847192622 | 0.045036 | 0.8355 |
| AB | 102.232 | 1 | 102.2320311 | 1.196744 | 0.2954 |
| AC | 41.02346 | 1 | 41.02346341 | 0.480227 | 0.5015 |
| AD | 374.6486 | 1 | 374.648561 | 4.385693 | 0.0581 |
| AE | 169.4842 | 1 | 169.4841845 | 1.984007 | 0.1843 |
| BC | 126.7865 | 1 | 126.7865247 | 1.484182 | 0.2465 |
| BD | 4510.72 | 1 | 4510.720235 | 52.80317 | <0.0001 |
| BE | 469.385 | 1 | 469.3850287 | 5.494692 | 0.0371 |
| CD | 32.88382 | 1 | 32.88382283 | 0.384943 | 0.5466 |
| CE | 466.9518 | 1 | 466.9518388 | 5.466209 | 0.0375 |
| DE | 2.65918 | 1 | 2.659179683 | 0.031129 | 0.8629 |

TABLE 14-continued

ANOVA for Response Surface 2FI Model
Analysis of variance table [Partial sum of squares - Type III]

| Source | Sum of Squares | df | Mean Square | F Value | p-value Prob > F |
|---|---|---|---|---|---|
| Residual | 1025.102 | 12 | 85.42517353 | | |
| Lack of Fit | 542.3064 | 7 | 77.47234358 | 0.802331 | 0.6191 |
| Pure Error | 482.7957 | 5 | 96.55913545 | | |
| Cor Total | 52127.7 | 27 | | | |

The Model F-value of 39.88 implies the model is significant. There is only a 0.01% chance that a "Model F-Value" this large could occur due to noise. Values of "Prob>F" less than 0.0500 indicate model terms are significant. In this case A, B, BD, BE, CE are significant model terms. Values greater than 0.1000 indicate the model terms are not significant. The "Lack of Fit F-value" of 0.80 implies the Lack of Fit is not significant relative to the pure error. There is a 61.91% chance that a "Lack of Fit F-value" this large could occur due to noise.

TABLE 15

| Std. Dev. | 9.242574 | R-Squared | 0.980335 |
|---|---|---|---|
| Mean | 109.8957 | Adj R-Squared | 0.955753 |
| C.V. % | 8.410316 | Pred R-Squared | 0.791041 |
| PRESS | 10892.57 | Adeq Precision | 23.48872 |

The "Pred R-Squared" of 0.7910 is in reasonable agreement with the "Adj R-Squared" of 0.9558. "Adeq Precision" measures the signal to noise ratio. A ratio greater than 4 is desirable. The ratio of 23.489 indicates an adequate signal. This model can be used to navigate the design space.

TABLE 16

| Factor | Coefficient Estimate | df | Standard Error | 95% CI Low | 95% CI High | VIF |
|---|---|---|---|---|---|---|
| Intercept | 112.537 | 1 | 2.382375371 | 107.3463 | 117.7278 | |
| A-Mp P1 | 30.20713 | 1 | 3.193318715 | 23.24948 | 37.16477 | 1.922928 |
| B-Mp P2 | −37.4043 | 1 | 3.208832488 | −44.3958 | −30.4129 | 1.939074 |
| C-PDI P1 | −0.05033 | 1 | 2.627492916 | −5.77515 | 5.674483 | 1.835677 |
| D-PDI P2 | −2.40854 | 1 | 2.695844679 | −8.28228 | 3.465205 | 2.163345 |
| E-Wt frac P1 | 0.470184 | 1 | 2.215586442 | −4.35716 | 5.297532 | 1.288823 |
| AB | 3.942093 | 1 | 3.603514627 | −3.90929 | 11.79348 | 1.853276 |
| AC | −2.0978 | 1 | 3.027194744 | −8.69349 | 4.497893 | 1.178035 |
| AD | 6.913059 | 1 | 3.301042663 | −0.2793 | 14.10541 | 2.108865 |
| AE | 5.177581 | 1 | 3.675828346 | −2.83136 | 13.18652 | 2.466812 |
| BC | 3.777226 | 1 | 3.100482806 | −2.97815 | 10.5326 | 1.630753 |
| BD | 19.56383 | 1 | 2.692303232 | 13.69781 | 25.42986 | 1.263168 |
| BE | 7.302224 | 1 | 3.115182109 | 0.514825 | 14.08962 | 1.848938 |
| CD | 1.765354 | 1 | 2.845336458 | −4.4341 | 7.96481 | 2.184276 |
| CE | −7.14424 | 1 | 3.055714267 | −13.8021 | −0.48641 | 2.482783 |
| DE | 0.474014 | 1 | 2.686642471 | −5.37968 | 6.327705 | 2.116413 |

The ANOVA analysis identified parameters and combinations of parameters that significantly contribute to the final result (i.e., melt fracture characteristic.) Thus, the following equation for the magnitude of slip-stick was determined to be:

| SS mag | = | |
|---|---|---|
| 1812.278 | | |
| 9.036292 | | * Mp P1 |
| −4.03563 | | * Mp P2 |
| 189.7406 | | * PDI P1 |
| −185.012 | | * PDI P2 |
| −3555.25 | | * Wt frac P1 |
| −3.22874 | | * Mp P1 * PDI P1 |
| 33.63554 | | * Mp P1 * Wt frac P1 |
| 0.533459 | | * Mp P2 * PDI P2 |
| 1.775348 | | * Mp P2 * Wt frac P1 |
| −21.6275 | | * PDI P1 * PDI P2 |
| 130.5963 | | * PDI P1 * Wt frac P1 |
| 219.8794 | | * PDI P2 * Wt frac P1 |

Figure 9:
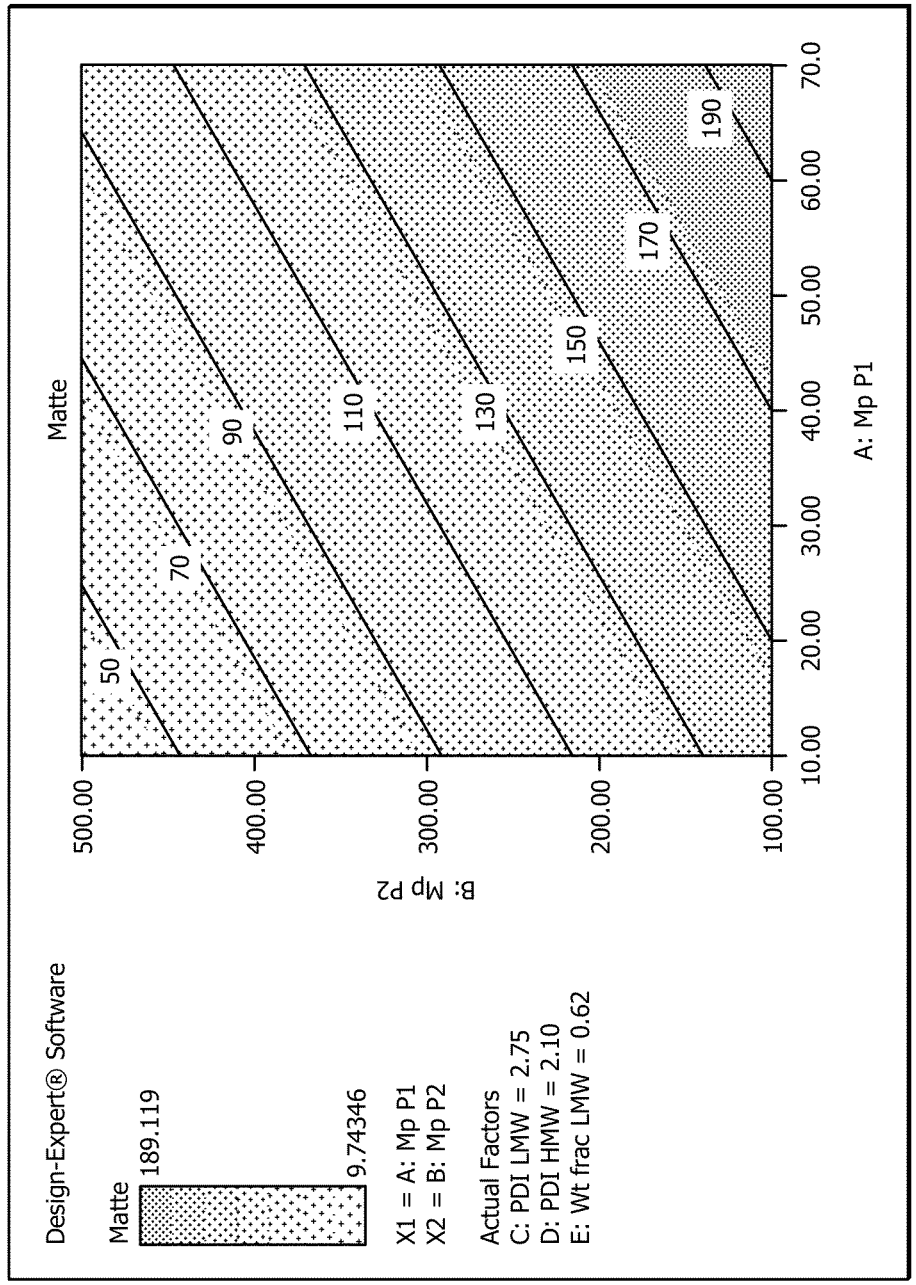
FIG. 9 is a plot of the stress for the smooth to matte transition as a function of the peak molecular weights of components P1 and P2.

The methodologies disclosed herein may be used to optimize the design of a polymer blend having designated melt fracture characteristics. Tables 17a-24a provide the optimization constraints for chemometric analysis while tables 17b-27b provide the solutions determined based on the constraints. FIG. 8 is a plot of the magnitude of slip-stick as a function of the weight fraction of the lower molecular weight (LMW) component and the peak molecular weight for the based on the results of chemometric analysis while FIG. 9 is a plot of the stress for the smooth to matte transition as a function of the peak molecular weights of components P1 and P2.

TABLE 17a

| | | Constraints | | | | |
|---|---|---|---|---|---|---|
| Name | Goal | Lower Limit | Upper Limit | Lower Weight | Upper Weight | Importance |
| Mp P1 | is in range | 11.18 | 63.25 | 1 | 1 | 3 |
| Mp P2 | is in range | 67.08 | 505.964425 | 1 | 1 | 3 |
| PDI LMW | is in range | 2 | 5 | 1 | 1 | 3 |
| PDI HMW | is in range | 2 | 5 | 1 | 1 | 3 |
| Wt frac LMW | maximize | 0.3 | 0.7 | 1 | 1 | 3 |
| SS mag | is in range | 300 | 1388.445312 | 1 | 1 | 3 |
| Matte | is in range | 90 | 189.119156 | 1 | 1 | 3 |

TABLE 17b

| | | | | | Wt | | | P1 Mw | P1 Mn | P2 Mw | P2 Mn | Blend Mw | Blend Mn | Blend |
|---|---|---|---|---|---|---|---|---|---|---|---|---|---|---|
| Number | Mp P1 | Mp P2 | PDI P1 | PDI P2 | frac P1 | SS mag | Matte | kg/mol | kg/mol | kg/mol | kg/mol | kg/mol | kg/mol | PDI |
| 54 | 18.51 | 67.08 | 4.07 | 4.87 | 0.7 | 300 | 92 | 37 | 9 | 148 | 30 | 71 | 12 | 6.1 |
| 55 | 11.18 | 79.18 | 2 | 2.42 | 0.68 | 300 | 141 | 16 | 8 | 123 | 51 | 50 | 11 | 4.6 |
| 16 | 14.91 | 70.91 | 2.25 | 3.16 | 0.7 | 309 | 130 | 22 | 10 | 126 | 40 | 53 | 13 | 4.2 |
| 45 | 20.97 | 82.23 | 2.01 | 4.13 | 0.7 | 312 | 120 | 30 | 15 | 167 | 40 | 71 | 18 | 3.9 |
| 46 | 20.63 | 217.37 | 3.94 | 3.77 | 0.7 | 317 | 98 | 41 | 10 | 422 | 112 | 155 | 14 | 10.9 |
| 22 | 22.11 | 232.99 | 3.84 | 2.92 | 0.7 | 346 | 105 | 43 | 11 | 398 | 136 | 150 | 16 | 9.6 |
| 5 | 15.81 | 94.87 | 2.5 | 2.5 | 0.7 | 373 | 138 | 25 | 10 | 150 | 60 | 62 | 13 | 4.7 |
| 15 | 28.25 | 276.03 | 3.66 | 4.51 | 0.7 | 375 | 100 | 54 | 15 | 586 | 130 | 214 | 20 | 10.6 |
| 53 | 33.69 | 387.2 | 2.92 | 4.47 | 0.7 | 380 | 103 | 58 | 20 | 819 | 183 | 286 | 27 | 10.6 |
| 37 | 21.65 | 102.47 | 4.86 | 4.74 | 0.7 | 388 | 92 | 48 | 10 | 223 | 47 | 100 | 13 | 7.8 |
| 6 | 28.3 | 296.51 | 4.38 | 4.83 | 0.7 | 399 | 94 | 59 | 14 | 652 | 135 | 237 | 19 | 12.8 |
| 48 | 17.84 | 111.27 | 4.91 | 4.09 | 0.7 | 399 | 97 | 40 | 8 | 225 | 55 | 95 | 11 | 8.8 |
| 32 | 22.1 | 240.8 | 4.68 | 2.85 | 0.7 | 399 | 99 | 48 | 10 | 407 | 143 | 155 | 14 | 11.0 |
| 2 | 31.62 | 260.87 | 2.5 | 5 | 0.7 | 406 | 110 | 50 | 20 | 583 | 117 | 210 | 27 | 7.9 |
| 29 | 11.34 | 68.44 | 2.82 | 2.02 | 0.7 | 417 | 147 | 19 | 7 | 97 | 48 | 43 | 9 | 4.7 |
| 35 | 34.84 | 347.06 | 3.12 | 4.3 | 0.7 | 428 | 107 | 62 | 20 | 720 | 167 | 259 | 27 | 9.7 |
| 11 | 27.43 | 174.94 | 2.59 | 2.98 | 0.7 | 442 | 129 | 44 | 17 | 302 | 101 | 121 | 23 | 5.3 |
| 26 | 28 | 187.31 | 2.56 | 2.15 | 0.7 | 464 | 135 | 45 | 18 | 275 | 128 | 114 | 24 | 4.8 |
| 24 | 27.07 | 75.37 | 4.94 | 4.87 | 0.7 | 465 | 100 | 60 | 12 | 166 | 34 | 92 | 15 | 6.1 |
| 12 | 42.25 | 452.43 | 2.59 | 4.2 | 0.7 | 476 | 110 | 68 | 26 | 927 | 221 | 326 | 36 | 9.1 |
| 8 | 13.45 | 102.46 | 4.35 | 2.2 | 0.7 | 510 | 129 | 28 | 6 | 152 | 69 | 65 | 9 | 7.4 |
| 38 | 40.57 | 322.68 | 4.68 | 3.14 | 0.7 | 568 | 107 | 88 | 19 | 572 | 182 | 233 | 26 | 9.1 |
| 20 | 55.85 | 424.07 | 4.43 | 2.17 | 0.7 | 596 | 99 | 118 | 27 | 625 | 288 | 270 | 36 | 7.4 |
| 42 | 39.29 | 230.1 | 4.35 | 4.73 | 0.7 | 608 | 115 | 82 | 19 | 500 | 106 | 207 | 25 | 8.3 |
| 43 | 61.89 | 477.51 | 4.81 | 2.34 | 0.7 | 623 | 93 | 136 | 28 | 730 | 312 | 314 | 39 | 8.1 |
| 10 | 55.4 | 418.54 | 3.62 | 2.72 | 0.7 | 637 | 110 | 105 | 29 | 690 | 254 | 281 | 40 | 7.1 |
| 44 | 30.04 | 134.32 | 3.76 | 2.47 | 0.7 | 644 | 140 | 58 | 15 | 211 | 85 | 104 | 21 | 5.1 |
| 56 | 11.18 | 68.56 | 5 | 2.03 | 0.67 | 671 | 138 | 25 | 5 | 98 | 48 | 49 | 7 | 6.9 |
| 3 | 44.72 | 357.77 | 5 | 5 | 0.7 | 672 | 113 | 100 | 20 | 800 | 160 | 310 | 27 | 11.4 |
| 34 | 61.94 | 462.08 | 2.58 | 2.58 | 0.7 | 673 | 113 | 99 | 39 | 742 | 288 | 292 | 52 | 5.6 |
| 9 | 54.17 | 424.34 | 4.63 | 3.38 | 0.7 | 678 | 109 | 117 | 25 | 780 | 231 | 316 | 34 | 9.2 |
| 40 | 50.52 | 389.58 | 4.78 | 3.75 | 0.7 | 681 | 112 | 110 | 23 | 754 | 201 | 304 | 31 | 9.7 |
| 7 | 41.26 | 84.62 | 4.5 | 4.69 | 0.7 | 697 | 126 | 88 | 19 | 183 | 39 | 116 | 23 | 5.1 |
| 36 | 59.44 | 407.26 | 4.25 | 3.01 | 0.7 | 749 | 117 | 123 | 29 | 707 | 235 | 298 | 39 | 7.6 |
| 50 | 59.77 | 501.49 | 4.64 | 3.96 | 0.7 | 765 | 115 | 129 | 28 | 998 | 252 | 390 | 38 | 10.3 |
| 41 | 57.16 | 354.59 | 2.24 | 2.97 | 0.7 | 776 | 135 | 86 | 38 | 611 | 206 | 243 | 51 | 4.8 |
| 31 | 52.33 | 324.83 | 2.94 | 4.23 | 0.7 | 786 | 135 | 90 | 31 | 668 | 158 | 263 | 40 | 6.5 |
| 52 | 38.76 | 96.39 | 2.49 | 2.26 | 0.7 | 827 | 168 | 61 | 25 | 145 | 64 | 86 | 30 | 2.9 |
| 25 | 59.34 | 451.14 | 3.48 | 4.19 | 0.7 | 829 | 130 | 111 | 32 | 923 | 220 | 355 | 43 | 8.3 |
| 13 | 56.66 | 316.85 | 2.89 | 3.54 | 0.7 | 845 | 140 | 96 | 33 | 596 | 168 | 246 | 44 | 5.6 |
| 18 | 56.36 | 363.99 | 4.2 | 4.63 | 0.7 | 849 | 133 | 116 | 28 | 783 | 169 | 316 | 37 | 8.6 |
| 14 | 50.34 | 157.45 | 3.15 | 4.52 | 0.7 | 850 | 145 | 89 | 28 | 335 | 74 | 163 | 35 | 4.7 |
| 27 | 62.09 | 396.93 | 2.3 | 3.42 | 0.7 | 865 | 137 | 94 | 41 | 734 | 215 | 286 | 54 | 5.3 |

TABLE 17b-continued

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 33 | 55.83 | 267.12 | 2.93 | 3.3 | 0.7 | 875 | 145 | 96 | 33 | 485 | 147 | 212 | 43 | 5.0 |
| 49 | 51.82 | 112.73 | 3.33 | 4.85 | 0.7 | 876 | 145 | 95 | 28 | 248 | 51 | 141 | 33 | 4.3 |
| 21 | 60.21 | 344.68 | 3.36 | 3.74 | 0.7 | 890 | 139 | 110 | 33 | 667 | 178 | 277 | 43 | 6.4 |
| 51 | 48.75 | 123.5 | 2.49 | 3.52 | 0.7 | 902 | 159 | 77 | 31 | 232 | 66 | 123 | 37 | 3.4 |
| 28 | 61 | 435.35 | 4.39 | 4.69 | 0.7 | 906 | 135 | 128 | 29 | 943 | 201 | 372 | 39 | 9.5 |
| 47 | 58.76 | 272.81 | 2.35 | 3.22 | 0.7 | 931 | 151 | 90 | 38 | 490 | 152 | 210 | 49 | 4.2 |
| 17 | 62.43 | 474.6 | 2.03 | 4.51 | 0.7 | 943 | 145 | 89 | 44 | 1008 | 223 | 365 | 58 | 6.3 |
| 19 | 54.95 | 197.64 | 2.2 | 3.86 | 0.7 | 946 | 157 | 82 | 37 | 388 | 101 | 174 | 46 | 3.8 |
| 4 | 44.72 | 94.87 | 5 | 2.5 | 0.7 | 956 | 158 | 100 | 20 | 150 | 60 | 115 | 25 | 4.6 |
| 39 | 45.3 | 93.11 | 3.88 | 2.27 | 0.7 | 974 | 169 | 89 | 23 | 140 | 62 | 105 | 28 | 3.7 |
| 23 | 58.83 | 213.65 | 4 | 2.46 | 0.7 | 986 | 155 | 118 | 29 | 335 | 136 | 183 | 38 | 4.8 |
| 30 | 49.54 | 80 | 3.28 | 2.28 | 0.7 | 1061 | 180 | 90 | 27 | 121 | 53 | 99 | 32 | 3.1 |
| 1 | 63.25 | 67.08 | 2.5 | 5 | 0.7 | 1147 | 168 | 100 | 40 | 150 | 30 | 115 | 36 | 3.2 |

TABLE 18a

Constraints

| Name | Goal | Lower Limit | Upper Limit | Lower Weight | Upper Weight | Importance |
|---|---|---|---|---|---|---|
| Mp P1 | is in range | 11.18 | 63.25 | 1 | 1 | 3 |
| Mp P2 | is in range | 67.08 | 505.964425 | 1 | 1 | 3 |
| PDI LMW | is in range | 2 | 5 | 1 | 1 | 3 |
| PDI HMW | is in range | 2 | 5 | 1 | 1 | 3 |
| Wt frac LMW | maximize | 0.3 | 0.7 | 1 | 1 | 3 |
| SS mag | is in range | 300 | 1388.445312 | 1 | 1 | 3 |
| Matte | is in range | 90 | 189.119156 | 1 | 1 | 3 |

TABLE 18b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 54 | 18.51 | 67.08 | 4.07 | 4.87 | 0.7 | 300 | 92 | 37 | 9 | 148 | 30 | 71 | 12 | 6.1 |
| 55 | 11.18 | 79.18 | 2 | 2.42 | 0.68 | 300 | 141 | 16 | 8 | 123 | 51 | 50 | 11 | 4.6 |
| 16 | 14.91 | 70.91 | 2.25 | 3.16 | 0.7 | 309 | 130 | 22 | 10 | 126 | 40 | 53 | 13 | 4.2 |
| 45 | 20.97 | 82.23 | 2.01 | 4.13 | 0.7 | 312 | 120 | 30 | 15 | 167 | 40 | 71 | 18 | 3.9 |
| 46 | 20.63 | 217.37 | 3.94 | 3.77 | 0.7 | 317 | 98 | 41 | 10 | 422 | 112 | 155 | 14 | 10.9 |
| 22 | 22.11 | 232.99 | 3.84 | 2.92 | 0.7 | 346 | 105 | 43 | 11 | 398 | 136 | 150 | 16 | 9.6 |
| 5 | 15.81 | 94.87 | 2.5 | 2.5 | 0.7 | 373 | 138 | 25 | 10 | 150 | 60 | 62 | 13 | 4.7 |
| 15 | 28.25 | 276.03 | 3.66 | 4.51 | 0.7 | 375 | 100 | 54 | 15 | 586 | 130 | 214 | 20 | 10.6 |
| 53 | 33.69 | 387.2 | 2.92 | 4.47 | 0.7 | 380 | 103 | 58 | 20 | 819 | 183 | 286 | 27 | 10.6 |
| 37 | 21.65 | 102.47 | 4.86 | 4.74 | 0.7 | 388 | 92 | 48 | 10 | 223 | 47 | 100 | 13 | 7.8 |
| 6 | 28.3 | 296.51 | 4.38 | 4.83 | 0.7 | 399 | 94 | 59 | 14 | 652 | 135 | 237 | 19 | 12.8 |
| 48 | 17.84 | 111.27 | 4.91 | 4.09 | 0.7 | 399 | 97 | 40 | 8 | 225 | 55 | 95 | 11 | 8.8 |
| 32 | 22.1 | 240.8 | 4.68 | 2.85 | 0.7 | 399 | 99 | 48 | 10 | 407 | 143 | 155 | 14 | 11.0 |
| 2 | 31.62 | 260.87 | 2.5 | 5 | 0.7 | 406 | 110 | 50 | 20 | 583 | 117 | 210 | 27 | 7.9 |
| 29 | 11.34 | 68.44 | 2.82 | 2.02 | 0.7 | 417 | 147 | 19 | 7 | 97 | 48 | 43 | 9 | 4.7 |
| 35 | 34.84 | 347.06 | 3.12 | 4.3 | 0.7 | 428 | 107 | 62 | 20 | 720 | 167 | 259 | 27 | 9.7 |
| 11 | 27.43 | 174.94 | 2.59 | 2.98 | 0.7 | 442 | 129 | 44 | 17 | 302 | 101 | 121 | 23 | 5.3 |
| 26 | 28 | 187.31 | 2.56 | 2.15 | 0.7 | 464 | 135 | 45 | 18 | 275 | 128 | 114 | 24 | 4.8 |
| 24 | 27.07 | 75.37 | 4.94 | 4.87 | 0.7 | 465 | 100 | 60 | 12 | 166 | 34 | 92 | 15 | 6.1 |
| 12 | 42.25 | 452.43 | 2.59 | 4.2 | 0.7 | 476 | 110 | 68 | 26 | 927 | 221 | 326 | 36 | 9.1 |
| 8 | 13.45 | 102.46 | 4.35 | 2.2 | 0.7 | 510 | 129 | 28 | 6 | 152 | 69 | 65 | 9 | 7.4 |
| 38 | 40.57 | 322.68 | 4.68 | 3.14 | 0.7 | 568 | 107 | 88 | 19 | 572 | 182 | 233 | 26 | 9.1 |
| 20 | 55.85 | 424.07 | 4.43 | 2.17 | 0.7 | 596 | 99 | 118 | 27 | 625 | 288 | 270 | 36 | 7.4 |
| 42 | 39.29 | 230.1 | 4.35 | 4.73 | 0.7 | 608 | 115 | 82 | 19 | 500 | 106 | 207 | 25 | 8.3 |
| 43 | 61.89 | 477.51 | 4.81 | 2.34 | 0.7 | 623 | 93 | 136 | 28 | 730 | 312 | 314 | 39 | 8.1 |
| 10 | 55.4 | 418.54 | 3.62 | 2.72 | 0.7 | 637 | 110 | 105 | 29 | 690 | 254 | 281 | 40 | 7.1 |
| 44 | 30.04 | 134.32 | 3.76 | 2.47 | 0.7 | 644 | 140 | 58 | 15 | 211 | 85 | 104 | 21 | 5.1 |
| 56 | 11.18 | 68.56 | 5 | 2.03 | 0.67 | 671 | 138 | 25 | 5 | 98 | 48 | 49 | 7 | 6.9 |
| 3 | 44.72 | 357.77 | 5 | 5 | 0.7 | 672 | 113 | 100 | 20 | 800 | 160 | 310 | 27 | 11.4 |
| 34 | 61.94 | 462.08 | 2.58 | 2.58 | 0.7 | 673 | 113 | 99 | 39 | 742 | 288 | 292 | 52 | 5.6 |
| 9 | 54.17 | 424.34 | 4.63 | 3.38 | 0.7 | 678 | 109 | 117 | 25 | 780 | 231 | 316 | 34 | 9.2 |
| 40 | 50.52 | 389.58 | 4.78 | 3.75 | 0.7 | 681 | 112 | 110 | 23 | 754 | 201 | 304 | 31 | 9.7 |
| 7 | 41.26 | 84.62 | 4.5 | 4.69 | 0.7 | 697 | 126 | 88 | 19 | 183 | 39 | 116 | 23 | 5.1 |
| 36 | 59.44 | 407.26 | 4.25 | 3.01 | 0.7 | 749 | 117 | 123 | 29 | 707 | 235 | 298 | 39 | 7.6 |

TABLE 18b-continued

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 50 | 59.77 | 501.49 | 4.64 | 3.96 | 0.7 | 765 | 115 | 129 | 28 | 998 | 252 | 390 | 38 | 10.3 |
| 41 | 57.16 | 354.59 | 2.24 | 2.97 | 0.7 | 776 | 135 | 86 | 38 | 611 | 206 | 243 | 51 | 4.8 |
| 31 | 52.33 | 324.83 | 2.94 | 4.23 | 0.7 | 786 | 135 | 90 | 31 | 668 | 158 | 263 | 40 | 6.5 |
| 52 | 38.76 | 96.39 | 2.49 | 2.26 | 0.7 | 827 | 168 | 61 | 25 | 145 | 64 | 86 | 30 | 2.9 |
| 25 | 59.34 | 451.14 | 3.48 | 4.19 | 0.7 | 829 | 130 | 111 | 32 | 923 | 220 | 355 | 43 | 8.3 |
| 13 | 56.66 | 316.85 | 2.89 | 3.54 | 0.7 | 845 | 140 | 96 | 33 | 596 | 168 | 246 | 44 | 5.6 |
| 18 | 56.36 | 363.99 | 4.2 | 4.63 | 0.7 | 849 | 133 | 116 | 28 | 783 | 169 | 316 | 37 | 8.6 |
| 14 | 50.34 | 157.45 | 3.15 | 4.52 | 0.7 | 850 | 145 | 89 | 28 | 335 | 74 | 163 | 35 | 4.7 |
| 27 | 62.09 | 396.93 | 2.3 | 3.42 | 0.7 | 865 | 137 | 94 | 41 | 734 | 215 | 286 | 54 | 5.3 |
| 33 | 55.83 | 267.12 | 2.93 | 3.3 | 0.7 | 875 | 145 | 96 | 33 | 485 | 147 | 212 | 43 | 5.0 |
| 49 | 51.82 | 112.73 | 3.33 | 4.85 | 0.7 | 876 | 145 | 95 | 28 | 248 | 51 | 141 | 33 | 4.3 |
| 21 | 60.21 | 344.68 | 3.36 | 3.74 | 0.7 | 890 | 139 | 110 | 33 | 667 | 178 | 277 | 43 | 6.4 |
| 51 | 48.75 | 123.5 | 2.49 | 3.52 | 0.7 | 902 | 159 | 77 | 31 | 232 | 66 | 123 | 37 | 3.4 |
| 28 | 61 | 435.35 | 4.39 | 4.69 | 0.7 | 906 | 135 | 128 | 29 | 943 | 201 | 372 | 39 | 9.5 |
| 47 | 58.76 | 272.81 | 2.35 | 3.22 | 0.7 | 931 | 151 | 90 | 38 | 490 | 152 | 210 | 49 | 4.2 |
| 17 | 62.43 | 474.6 | 2.03 | 4.51 | 0.7 | 943 | 145 | 89 | 44 | 1008 | 223 | 365 | 58 | 6.3 |
| 19 | 54.95 | 197.64 | 2.2 | 3.86 | 0.7 | 946 | 157 | 82 | 37 | 388 | 101 | 174 | 46 | 3.8 |
| 4 | 44.72 | 94.87 | 5 | 2.5 | 0.7 | 956 | 158 | 100 | 20 | 150 | 60 | 115 | 25 | 4.6 |
| 39 | 45.3 | 93.11 | 3.88 | 2.27 | 0.7 | 974 | 169 | 89 | 23 | 140 | 62 | 105 | 28 | 3.7 |
| 23 | 58.83 | 213.65 | 4 | 2.46 | 0.7 | 986 | 155 | 118 | 29 | 335 | 136 | 183 | 38 | 4.8 |
| 30 | 49.54 | 80 | 3.28 | 2.28 | 0.7 | 1061 | 180 | 90 | 27 | 121 | 53 | 99 | 32 | 3.1 |
| 1 | 63.25 | 67.08 | 2.5 | 5 | 0.7 | 1147 | 168 | 100 | 40 | 150 | 30 | 115 | 36 | 3.2 |

TABLE 19a

Constraints

| Name | Goal | Lower Limit | Upper Limit | Lower Weight | Upper Weight | Importance |
|---|---|---|---|---|---|---|
| Mp P1 | is in range | 11.18 | 63.25 | 1 | 1 | 3 |
| Mp P2 | is in range | 67.08 | 505.9644 | 1 | 1 | 3 |
| PDI P1 | is in range | 2 | 3 | 1 | 1 | 3 |
| PDI P2 | is in range | 2 | 3 | 1 | 1 | 3 |
| Wt frac P1 | maximize | 0.3 | 0.7 | 1 | 1 | 3 |
| SS mag | is in range | 300 | 1388.445 | 1 | 1 | 3 |
| Matte | is in range | 90 | 189.1192 | 1 | 1 | 3 |

TABLE 19b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 28 | 22.42 | 221.01 | 2.96 | 2.99 | 0.7 | 303 | 112 | 39 | 13 | 382 | 128 | 142 | 18 | 7.9 |
| 8 | 13.37 | 78.57 | 2.31 | 2.82 | 0.7 | 306 | 133 | 20 | 9 | 132 | 47 | 54 | 12 | 4.6 |
| 2 | 21.54 | 169.78 | 2.04 | 2.22 | 0.7 | 331 | 134 | 31 | 15 | 253 | 114 | 97 | 20 | 4.8 |
| 29 | 20.48 | 138.4 | 2.35 | 2.91 | 0.7 | 348 | 129 | 31 | 13 | 236 | 81 | 93 | 18 | 5.2 |
| 4 | 28.5 | 260.16 | 2.77 | 2.29 | 0.7 | 350 | 117 | 47 | 17 | 394 | 172 | 151 | 23 | 6.4 |
| 23 | 16.93 | 145.57 | 2.75 | 2.1 | 0.7 | 354 | 133 | 28 | 10 | 211 | 100 | 83 | 14 | 5.9 |
| 34 | 16.74 | 94.61 | 2.69 | 2.9 | 0.7 | 368 | 131 | 27 | 10 | 161 | 56 | 68 | 14 | 5.0 |
| 14 | 17.25 | 111.78 | 2.61 | 2.58 | 0.7 | 373 | 134 | 28 | 11 | 180 | 70 | 73 | 14 | 5.1 |
| 1 | 15.81 | 94.87 | 2.5 | 2.5 | 0.7 | 373 | 138 | 25 | 10 | 150 | 60 | 62 | 13 | 4.7 |
| 7 | 15.25 | 101.85 | 2.54 | 2.18 | 0.7 | 382 | 142 | 24 | 10 | 150 | 69 | 62 | 13 | 4.8 |
| 16 | 18.37 | 101.78 | 2.06 | 2.09 | 0.7 | 410 | 149 | 26 | 13 | 147 | 70 | 63 | 17 | 3.7 |
| 12 | 15.45 | 85.03 | 2.94 | 2.09 | 0.7 | 461 | 145 | 26 | 9 | 123 | 59 | 55 | 12 | 4.6 |
| 18 | 20.75 | 71.69 | 2.85 | 2.96 | 0.7 | 483 | 138 | 35 | 12 | 123 | 42 | 62 | 16 | 3.9 |
| 9 | 45.5 | 378.94 | 2.63 | 2.83 | 0.7 | 498 | 112 | 74 | 28 | 637 | 225 | 243 | 38 | 6.4 |
| 32 | 51.31 | 382.15 | 2.35 | 2.37 | 0.7 | 565 | 117 | 79 | 33 | 588 | 248 | 232 | 45 | 5.1 |
| 27 | 44.77 | 279.49 | 2.89 | 2.41 | 0.7 | 629 | 130 | 76 | 26 | 434 | 180 | 183 | 35 | 5.2 |
| 5 | 31.21 | 96.43 | 2.98 | 2.78 | 0.7 | 662 | 149 | 54 | 18 | 161 | 58 | 86 | 23 | 3.8 |
| 21 | 61.94 | 462.08 | 2.53 | 2.53 | 0.7 | 666 | 112 | 99 | 39 | 735 | 291 | 289 | 53 | 5.5 |
| 15 | 45.65 | 263.59 | 2.62 | 2.88 | 0.7 | 673 | 135 | 74 | 28 | 447 | 155 | 186 | 37 | 5.0 |
| 13 | 56.53 | 320.97 | 2.15 | 2.39 | 0.7 | 776 | 138 | 83 | 39 | 496 | 208 | 207 | 51 | 4.1 |
| 17 | 41.87 | 152.71 | 2.19 | 2.2 | 0.7 | 780 | 161 | 62 | 28 | 227 | 103 | 111 | 36 | 3.1 |
| 20 | 51.14 | 250.93 | 2.87 | 2.53 | 0.7 | 796 | 144 | 87 | 30 | 399 | 158 | 180 | 40 | 4.5 |
| 22 | 43.78 | 124.44 | 2.61 | 2.75 | 0.7 | 846 | 161 | 71 | 27 | 206 | 75 | 111 | 34 | 3.3 |
| 35 | 46.56 | 171.48 | 2.78 | 2.13 | 0.7 | 850 | 159 | 78 | 28 | 250 | 117 | 129 | 36 | 3.6 |
| 33 | 48.01 | 175.71 | 2.33 | 2.46 | 0.7 | 854 | 160 | 73 | 31 | 276 | 112 | 134 | 40 | 3.3 |
| 30 | 50.48 | 160.59 | 2.06 | 2.49 | 0.7 | 927 | 167 | 72 | 35 | 253 | 102 | 127 | 44 | 2.9 |
| 19 | 53.41 | 168.55 | 2.39 | 2.57 | 0.7 | 970 | 166 | 83 | 35 | 270 | 105 | 139 | 43 | 3.2 |

TABLE 19b-continued

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 3  | 46.12 | 79.16  | 2.06 | 2.14 | 0.7  | 1002 | 185 | 66  | 32 | 116 | 54  | 81  | 37 | 2.2  |
| 24 | 54.19 | 148.01 | 2.52 | 2.67 | 0.7  | 1014 | 170 | 86  | 34 | 242 | 91  | 133 | 42 | 3.2  |
| 10 | 51.39 | 102.27 | 2.11 | 2.75 | 0.7  | 1028 | 177 | 75  | 35 | 170 | 62  | 103 | 41 | 2.5  |
| 6  | 60.72 | 174.06 | 2.73 | 2.48 | 0.7  | 1100 | 173 | 100 | 37 | 274 | 111 | 152 | 46 | 3.3  |
| 25 | 55.53 | 102.14 | 2.99 | 2.04 | 0.7  | 1144 | 186 | 96  | 32 | 146 | 72  | 111 | 38 | 2.9  |
| 26 | 59.01 | 71.75  | 2.87 | 2.84 | 0.7  | 1202 | 188 | 100 | 35 | 121 | 43  | 106 | 37 | 2.9  |
| 31 | 60.49 | 87.99  | 2.79 | 2.77 | 0.7  | 1213 | 187 | 101 | 36 | 146 | 53  | 115 | 40 | 2.9  |
| 11 | 62.96 | 130.5  | 2.93 | 2.06 | 0.7  | 1224 | 187 | 108 | 37 | 187 | 91  | 132 | 45 | 2.9  |
| 36 | 11.68 | 244.73 | 3    | 2.97 | 0.51 | 300  | 97  | 20  | 7  | 422 | 142 | 217 | 13 | 17.2 |

TABLE 20a

Constraints

| Name | Goal | Lower Limit | Upper Limit | Lower Weight | Upper Weight | Importance |
|---|---|---|---|---|---|---|
| Name         | minimize        | 11.18034 | 63.24555 | 1 | 1 | 3 |
| Mp P1        | maximize        | 67.08204 | 505.9644 | 1 | 1 | 3 |
| Mp P2        | is in range     | 2.5      | 5        | 1 | 1 | 3 |
| PDI P1       | is equal to 2.50| 2.5      | 5        | 1 | 1 | 3 |
| PDI P2       | maximize        | 0.3      | 0.7      | 1 | 1 | 3 |
| Wt frac P1   | is in range     | 300      | 1388.445 | 1 | 1 | 3 |
| Matte        | is in range     | 90       | 189.1192 | 1 | 1 | 3 |

TABLE 20b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 29 | 14.96 | 249.08 | 5    | 2.5 | 0.7 | 300 | 90  | 33 | 7  | 394 | 158 | 142 | 9  | 15 |
| 24 | 22.27 | 287.88 | 4.97 | 2.5 | 0.7 | 341 | 90  | 50 | 10 | 455 | 182 | 171 | 14 | 12 |
| 25 | 24.21 | 298.49 | 4.97 | 2.5 | 0.7 | 353 | 90  | 54 | 11 | 472 | 189 | 179 | 15 | 12 |
| 26 | 19.48 | 273.47 | 4.95 | 2.5 | 0.7 | 320 | 90  | 43 | 9  | 432 | 173 | 160 | 12 | 13 |
| 18 | 22.78 | 296.63 | 4.74 | 2.5 | 0.7 | 314 | 90  | 50 | 10 | 469 | 188 | 175 | 15 | 12 |
| 14 | 21.97 | 293.87 | 4.67 | 2.5 | 0.7 | 300 | 90  | 47 | 10 | 465 | 186 | 173 | 14 | 12 |
| 7  | 24.75 | 312.94 | 4.51 | 2.5 | 0.7 | 300 | 90  | 53 | 12 | 495 | 198 | 185 | 16 | 11 |
| 5  | 24.88 | 313.9  | 4.5  | 2.5 | 0.7 | 300 | 90  | 53 | 12 | 496 | 199 | 186 | 16 | 11 |
| 11 | 26.16 | 320.87 | 4.5  | 2.5 | 0.7 | 310 | 90  | 55 | 12 | 507 | 203 | 191 | 17 | 11 |
| 9  | 25.28 | 317.39 | 4.46 | 2.5 | 0.7 | 300 | 90  | 53 | 12 | 502 | 201 | 188 | 17 | 11 |
| 3  | 25.61 | 319.05 | 4.45 | 2.5 | 0.7 | 300 | 90  | 54 | 12 | 504 | 202 | 189 | 17 | 11 |
| 6  | 26.27 | 323.11 | 4.43 | 2.5 | 0.7 | 303 | 90  | 55 | 12 | 511 | 204 | 192 | 17 | 11 |
| 1  | 26.73 | 326.94 | 4.38 | 2.5 | 0.7 | 300 | 90  | 56 | 13 | 517 | 207 | 194 | 18 | 11 |
| 10 | 26.46 | 324.74 | 4.37 | 2.5 | 0.7 | 300 | 90  | 55 | 13 | 513 | 205 | 193 | 18 | 11 |
| 16 | 25.54 | 313.87 | 4.37 | 2.5 | 0.7 | 300 | 91  | 53 | 12 | 496 | 199 | 186 | 17 | 11 |
| 2  | 26.93 | 328.36 | 4.36 | 2.5 | 0.7 | 300 | 90  | 56 | 13 | 519 | 208 | 195 | 18 | 11 |
| 39 | 36.62 | 380.5  | 4.36 | 2.5 | 0.7 | 379 | 90  | 76 | 18 | 602 | 241 | 234 | 24 | 10 |
| 4  | 27.63 | 333.47 | 4.31 | 2.5 | 0.7 | 300 | 90  | 57 | 13 | 527 | 211 | 198 | 19 | 11 |
| 8  | 28.14 | 336.6  | 4.27 | 2.5 | 0.7 | 300 | 90  | 58 | 14 | 532 | 213 | 200 | 19 | 11 |
| 28 | 34.97 | 374.83 | 4.24 | 2.5 | 0.7 | 353 | 90  | 72 | 17 | 593 | 237 | 228 | 24 | 10 |
| 23 | 31.92 | 358.8  | 4.22 | 2.5 | 0.7 | 325 | 90  | 66 | 16 | 567 | 227 | 216 | 22 | 10 |
| 21 | 28.1  | 331.13 | 4.15 | 2.5 | 0.7 | 300 | 92  | 57 | 14 | 524 | 209 | 197 | 19 | 10 |
| 13 | 30    | 348.83 | 4.1  | 2.5 | 0.7 | 300 | 91  | 61 | 15 | 552 | 221 | 208 | 21 | 10 |
| 12 | 30.7  | 355.75 | 4.08 | 2.5 | 0.7 | 300 | 90  | 62 | 15 | 562 | 225 | 212 | 21 | 10 |
| 15 | 31.65 | 362.87 | 4    | 2.5 | 0.7 | 300 | 90  | 63 | 16 | 574 | 229 | 216 | 22 | 10 |
| 17 | 31.15 | 356.61 | 3.99 | 2.5 | 0.7 | 300 | 91  | 62 | 16 | 564 | 226 | 213 | 22 | 10 |
| 19 | 32.59 | 369.98 | 3.92 | 2.5 | 0.7 | 300 | 90  | 65 | 16 | 585 | 234 | 221 | 23 | 10 |
| 27 | 34.39 | 379.94 | 3.91 | 2.5 | 0.7 | 315 | 90  | 68 | 17 | 601 | 240 | 228 | 24 | 9  |
| 22 | 33.24 | 374.92 | 3.86 | 2.5 | 0.7 | 300 | 90  | 65 | 17 | 593 | 237 | 224 | 23 | 10 |
| 38 | 33.19 | 345.89 | 3.29 | 2.5 | 0.7 | 307 | 99  | 60 | 18 | 547 | 219 | 206 | 25 | 8  |
| 32 | 37.11 | 394.15 | 3.17 | 2.5 | 0.7 | 300 | 94  | 66 | 21 | 623 | 249 | 233 | 29 | 8  |
| 33 | 37.25 | 395.52 | 3.15 | 2.5 | 0.7 | 300 | 94  | 66 | 21 | 625 | 250 | 234 | 29 | 8  |
| 35 | 39.66 | 425.65 | 3.14 | 2.5 | 0.7 | 300 | 90  | 70 | 22 | 673 | 269 | 251 | 31 | 8  |
| 34 | 35.78 | 375.69 | 3.12 | 2.5 | 0.7 | 300 | 97  | 63 | 20 | 594 | 238 | 222 | 28 | 8  |
| 40 | 38.3  | 400.26 | 2.91 | 2.5 | 0.7 | 300 | 96  | 65 | 22 | 633 | 253 | 236 | 31 | 8  |
| 41 | 39.48 | 413.82 | 2.85 | 2.5 | 0.7 | 300 | 94  | 67 | 23 | 654 | 262 | 243 | 32 | 8  |
| 51 | 37.22 | 286.55 | 2.79 | 2.5 | 0.7 | 445 | 120 | 62 | 22 | 453 | 181 | 179 | 30 | 6  |

TABLE 20b-continued

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 48 | 43.8 | 463.98 | 2.59 | 2.5 | 0.7 | 300 | 90 | 70 | 27 | 734 | 293 | 269 | 37 | 7 |
| 44 | 38.68 | 394.22 | 2.58 | 2.5 | 0.7 | 300 | 99 | 62 | 24 | 623 | 249 | 230 | 33 | 7 |
| 45 | 37.66 | 380.05 | 2.57 | 2.5 | 0.7 | 300 | 101 | 60 | 23 | 601 | 240 | 223 | 32 | 7 |
| 46 | 38.71 | 392.75 | 2.52 | 2.5 | 0.7 | 300 | 100 | 61 | 24 | 621 | 248 | 229 | 33 | 7 |
| 50 average | 37.17 30.6997619 | 286.18 | 2.5 | 2.5 | 0.7 | 429 | 122 | 59 | 24 | 452 | 181 | 177 | 32 | 6 |
| 20 | 23.69 | 309.32 | 4.5 | 2.5 | 0.69 | 300 | 90 | 50 | 11 | 489 | 196 | 186 | 16 | 12 |
| 31 | 29.59 | 328.19 | 5 | 2.5 | 0.69 | 398 | 90 | 66 | 13 | 519 | 208 | 207 | 19 | 11 |
| 42 | 39.78 | 421.67 | 2.93 | 2.5 | 0.69 | 300 | 92 | 68 | 23 | 667 | 267 | 254 | 32 | 8 |
| 30 | 21.12 | 292.68 | 4.71 | 2.5 | 0.67 | 328 | 91 | 46 | 10 | 463 | 185 | 183 | 14 | 13 |
| 36 | 27.8 | 321.45 | 5 | 2.5 | 0.67 | 396 | 90 | 62 | 12 | 508 | 203 | 209 | 18 | 12 |
| 37 | 13.62 | 255.86 | 4.85 | 2.5 | 0.66 | 300 | 90 | 30 | 6 | 405 | 162 | 157 | 9 | 17 |
| 43 | 11.18 | 246.86 | 4.87 | 2.5 | 0.65 | 300 | 90 | 25 | 5 | 390 | 156 | 153 | 8 | 20 |
| 47 | 20.11 | 295.39 | 5 | 2.5 | 0.61 | 391 | 90 | 45 | 9 | 467 | 187 | 210 | 14 | 15 |
| 49 | 18.34 | 298.64 | 4.09 | 2.5 | 0.58 | 308 | 91 | 37 | 9 | 472 | 189 | 220 | 15 | 15 |
| 52 | 11.19 | 288 | 3.7 | 2.5 | 0.49 | 300 | 90 | 22 | 6 | 455 | 182 | 243 | 11 | 21 |
| 53 | 11.18 | 253.04 | 5 | 2.5 | 0.48 | 536 | 100 | 25 | 5 | 400 | 160 | 220 | 10 | 22 |

TABLE 21a

Constraints

| Name | Goal | Lower Limit | Upper Limit | Lower Weight | Upper Weight | Importance |
|---|---|---|---|---|---|---|
| Mp P1 | minimize | 11.18034 | 63.24555 | 1 | 1 | 3 |
| Mp P2 | maximize | 200 | 505.9644 | 1 | 1 | 3 |
| PDI P1 | is in range | 2 | 5 | 1 | 1 | 3 |
| PDI P2 | is equal to 2.00 | 2.5 | 5 | 1 | 1 | 3 |
| Wt frac P1 | is equal to 0.70 | 0.3 | 0.7 | 1 | 1 | 3 |
| SS mag | is in range | 300 | 1388.445 | 1 | 1 | 3 |
| Matte | is in range | 90 | 189.1192 | 1 | 1 | 3 |

TABLE 21b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 16 | 46.41 | 233.29 | 2.45 | 2 | 0.7 | 692 | 146 | 73 | 30 | 330 | 165 | 150 | 39 | 3.8 |
| 5 | 31.62 | 260.87 | 2.5 | 2 | 0.7 | 337 | 123 | 50 | 20 | 369 | 184 | 146 | 27 | 5.3 |
| 11 | 42.58 | 256.36 | 2.52 | 2 | 0.7 | 574 | 136 | 68 | 27 | 363 | 181 | 156 | 36 | 4.3 |
| 8 | 56.49 | 445.72 | 2.81 | 2 | 0.7 | 531 | 101 | 95 | 34 | 630 | 315 | 255 | 46 | 5.5 |
| 15 | 59.9 | 372.59 | 2.99 | 2 | 0.7 | 732 | 122 | 104 | 35 | 527 | 263 | 231 | 47 | 4.9 |
| 4 | 50.44 | 413.87 | 3.14 | 2 | 0.7 | 477 | 101 | 89 | 28 | 585 | 293 | 238 | 39 | 6.1 |
| 9 | 49.28 | 307.33 | 3.26 | 2 | 0.7 | 648 | 126 | 89 | 27 | 435 | 217 | 193 | 37 | 5.2 |
| 17 | 61.89 | 444.83 | 3.58 | 2 | 0.7 | 644 | 103 | 117 | 33 | 629 | 315 | 271 | 45 | 6.1 |
| 19 | 62.66 | 479.96 | 3.61 | 2 | 0.7 | 596 | 95 | 119 | 33 | 679 | 339 | 287 | 45 | 6.3 |
| 18 | 61.18 | 282.4 | 3.63 | 2 | 0.7 | 921 | 143 | 117 | 32 | 399 | 200 | 201 | 43 | 4.7 |
| 10 | 32.27 | 245.29 | 3.75 | 2 | 0.7 | 474 | 120 | 62 | 17 | 347 | 173 | 148 | 23 | 6.5 |
| 12 | 55.7 | 288.79 | 3.88 | 2 | 0.7 | 815 | 134 | 110 | 28 | 408 | 204 | 199 | 38 | 5.2 |
| 20 | 36.02 | 204.1 | 4.41 | 2 | 0.7 | 658 | 131 | 76 | 17 | 289 | 144 | 140 | 23 | 6.0 |
| 14 | 45.14 | 232 | 4.44 | 2 | 0.7 | 757 | 134 | 95 | 21 | 328 | 164 | 165 | 29 | 5.7 |
| 3 | 47.08 | 378.96 | 4.48 | 2 | 0.7 | 529 | 99 | 100 | 22 | 536 | 268 | 231 | 31 | 7.5 |
| 1 | 28.13 | 318.9 | 4.5 | 2 | 0.7 | 334 | 93 | 60 | 13 | 451 | 225 | 177 | 18 | 9.6 |
| 7 | 53.82 | 376.14 | 4.52 | 2 | 0.7 | 642 | 106 | 114 | 25 | 532 | 266 | 240 | 35 | 6.9 |
| 22 | 62.21 | 285.46 | 4.69 | 2 | 0.7 | 938 | 138 | 135 | 29 | 404 | 202 | 215 | 39 | 5.6 |
| 6 | 32.69 | 254.74 | 4.82 | 2 | 0.7 | 545 | 113 | 72 | 15 | 360 | 180 | 158 | 21 | 7.7 |
| 21 | 46.18 | 205.97 | 4.9 | 2 | 0.7 | 840 | 139 | 102 | 21 | 291 | 146 | 159 | 28 | 5.7 |
| 2 | 44.72 | 357.77 | 5 | 2 | 0.7 | 553 | 99 | 100 | 20 | 506 | 253 | 222 | 28 | 8.0 |
| 13 | 11.18 | 212.43 | 5 | 2 | 0.7 | 317 | 99 | 25 | 5 | 300 | 150 | 108 | 7 | 15.3 |

TABLE 22a

Constraints

| Name | Goal | Lower Limit | Upper Limit | Lower Weight | Upper Weight | Importance |
|---|---|---|---|---|---|---|
| Mp P1 | minimize | 11.18 | 63.25 | 1 | 1 | 3 |
| Mp P2 | maximize | 275 | 505.9644 | 1 | 1 | 3 |
| PDI P1 | is in range | 2.5 | 3 | 1 | 1 | 3 |
| PDI P2 | is in range | 2 | 2.3 | 1 | 1 | 3 |
| Wt frac P1 | is in range | 0.6 | 0.65 | 1 | 1 | 3 |
| SS mag | maximize | 300 | 1388.445 | 1 | 1 | 3 |
| Matte | maximize | 90 | 189.1192 | 1 | 1 | 3 |

TABLE 22b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 1 | 52.32 | 353.07 | 2.5 | 2.3 | 0.65 | 635 | 120 | 83 | 33 | 535 | 233 | 241 | 47 | 5.1 |
| 2 | 52.86 | 352.81 | 2.5 | 2.3 | 0.65 | 646 | 121 | 84 | 33 | 535 | 233 | 242 | 48 | 5.1 |
| 3 | 52.42 | 352.01 | 2.58 | 2.3 | 0.65 | 640 | 121 | 84 | 33 | 534 | 232 | 242 | 47 | 5.2 |
| 4 | 52.17 | 350.9 | 2.61 | 2.3 | 0.65 | 638 | 120 | 84 | 32 | 532 | 231 | 241 | 46 | 5.2 |
| 5 | 52.18 | 355.86 | 2.62 | 2.3 | 0.65 | 630 | 119 | 84 | 32 | 540 | 235 | 244 | 46 | 5.3 |
| 6 | 52.71 | 351.21 | 2.6 | 2.3 | 0.65 | 648 | 121 | 85 | 33 | 533 | 232 | 242 | 47 | 5.2 |
| 7 | 52.12 | 349.06 | 2.5 | 2.3 | 0.64 | 639 | 121 | 82 | 33 | 529 | 230 | 243 | 48 | 5.1 |
| 8 | 52.38 | 351.72 | 2.75 | 2.3 | 0.65 | 644 | 120 | 87 | 32 | 533 | 232 | 243 | 45 | 5.4 |
| 9 | 52.36 | 350.45 | 2.91 | 2.3 | 0.65 | 649 | 119 | 89 | 31 | 531 | 231 | 244 | 44 | 5.5 |
| 10 | 53.94 | 369.36 | 2.5 | 2.29 | 0.65 | 638 | 118 | 85 | 34 | 559 | 244 | 251 | 49 | 5.1 |
| 11 | 52.16 | 350.37 | 2.3 | 2.3 | 0.65 | 647 | 119 | 90 | 30 | 531 | 231 | 245 | 43 | 5.6 |
| 12 | 51.7 | 347.37 | 2.5 | 2.23 | 0.65 | 628 | 121 | 82 | 33 | 519 | 233 | 235 | 47 | 5.0 |
| 13 | 52.93 | 344.28 | 2.95 | 2.3 | 0.65 | 671 | 121 | 91 | 31 | 522 | 227 | 242 | 44 | 5.5 |
| 14 | 52.13 | 352.35 | 2.95 | 2.3 | 0.63 | 646 | 118 | 90 | 30 | 534 | 232 | 254 | 45 | 5.7 |
| 15 | 52.16 | 350.27 | 2.52 | 2.3 | 0.61 | 643 | 118 | 83 | 33 | 531 | 231 | 258 | 49 | 5.2 |
| 16 | 52.28 | 347.24 | 2.5 | 2.11 | 0.65 | 631 | 121 | 83 | 33 | 504 | 239 | 230 | 47 | 4.9 |
| 17 | 52.29 | 348.17 | 2.62 | 2.12 | 0.65 | 633 | 120 | 85 | 32 | 507 | 239 | 232 | 46 | 5.0 |
| 18 | 51.8 | 346.26 | 2.7 | 2.3 | 0.6 | 650 | 118 | 85 | 32 | 525 | 228 | 261 | 48 | 5.4 |
| 19 | 51.72 | 341.49 | 2.98 | 2.3 | 0.61 | 661 | 119 | 89 | 30 | 518 | 225 | 256 | 45 | 5.7 |
| 20 | 52.48 | 342.98 | 3 | 2.3 | 0.6 | 674 | 119 | 91 | 30 | 520 | 226 | 263 | 46 | 5.7 |

TABLE 23a

Constraints

| Name | Goal | Lower Limit | Upper Limit | Lower Weight | Upper Weight | Importance |
|---|---|---|---|---|---|---|
| Mp P1 | minimize | 11.18 | 63.25 | 1 | 1 | 3 |
| Mp P2 | is equal to 340.00 | 275 | 505.9644 | 1 | 1 | 3 |
| PDI P1 | is in range | 2.5 | 3 | 1 | 1 | 3 |
| PDI P2 | is equal to 2.10 | 2 | 2.3 | 1 | 1 | 3 |
| Wt frac P1 | maximize | 0.6 | 0.65 | 1 | 1 | 3 |
| SS mag | maximize | 300 | 1388.445 | 1 | 1 | 3 |
| Matte | maximize | 90 | 189.1192 | 1 | 1 | 3 |

TABLE 23b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 7 | 51.8 | 340 | 2.93 | 2.1 | 0.65 | 646 | 120 | 89 | 30 | 493 | 235 | 230 | 44 | 5.3 |
| 6 | 51.89 | 340 | 2.86 | 2.1 | 0.65 | 646 | 121 | 88 | 31 | 493 | 235 | 229 | 44 | 5.2 |
| 5 | 51.95 | 340 | 2.76 | 2.1 | 0.65 | 644 | 121 | 86 | 31 | 493 | 235 | 229 | 45 | 5.1 |
| 3 | 52.07 | 340 | 2.59 | 2.1 | 0.65 | 642 | 122 | 84 | 32 | 493 | 235 | 227 | 46 | 4.9 |
| 1 | 52.11 | 340 | 2.5 | 2.1 | 0.65 | 640 | 122 | 82 | 33 | 493 | 235 | 226 | 47 | 4.8 |
| 2 | 52.29 | 340 | 2.55 | 2.1 | 0.65 | 645 | 122 | 84 | 33 | 493 | 235 | 227 | 47 | 4.8 |
| 4 | 52.4 | 340 | 2.5 | 2.1 | 0.65 | 646 | 123 | 83 | 33 | 493 | 235 | 226 | 47 | 4.8 |
| 8 | 63.25 | 340 | 2.5 | 2.1 | 0.7 | 862 | 138 | 100 | 40 | 493 | 235 | 218 | 53 | 4.1 |

TABLE 24a

Constraints

| Name | Goal | Lower Limit | Upper Limit | Lower Weight | Upper Weight | Importance |
|---|---|---|---|---|---|---|
| Mp P1 | minimize | 11.18 | 63.25 | 1 | 1 | 3 |
| Mp P2 | is equal to 340.00 | 275 | 505.9644 | 1 | 1 | 3 |
| PDI P1 | is in range | 2.5 | 3 | 1 | 1 | 3 |
| PDI P2 | is equal to 2.10 | 2 | 2.3 | 1 | 1 | 3 |
| Wt frac P1 | maximize | 0.6 | 0.7 | 1 | 1 | 3 |
| SS mag | maximize | 300 | 1388.445 | 1 | 1 | 3 |
| Matte | maximize | 90 | 189.1192 | 1 | 1 | 3 |

TABLE 24b

Solutions

| Number | Mp P1 | Mp P2 | PDI P1 | PDI P2 | Wt frac P1 | SS mag | Matte | P1 Mw kg/mol | P1 Mn kg/mol | P2 Mw kg/mol | P2 Mn kg/mol | Blend Mw kg/mol | Blend Mn kg/mol | Blend PDI |
|---|---|---|---|---|---|---|---|---|---|---|---|---|---|---|
| 5 | 51.73 | 340 | 2.66 | 2.1 | 0.7 | 626 | 124 | 84 | 32 | 493 | 235 | 207 | 43 | 4.8 |
| 8 | 52.06 | 340 | 2.79 | 2.1 | 0.7 | 636 | 124 | 87 | 31 | 493 | 235 | 209 | 42 | 5.0 |
| 4 | 52.26 | 340 | 2.66 | 2.1 | 0.7 | 637 | 125 | 85 | 32 | 493 | 235 | 207 | 43 | 4.8 |
| 6 | 52.28 | 340 | 2.5 | 2.1 | 0.7 | 634 | 125 | 83 | 33 | 493 | 235 | 206 | 45 | 4.6 |
| 9 | 52.32 | 340 | 2.92 | 2.1 | 0.7 | 645 | 123 | 89 | 31 | 493 | 235 | 210 | 41 | 5.1 |
| 7 | 52.33 | 340 | 2.76 | 2.1 | 0.7 | 641 | 124 | 87 | 31 | 493 | 235 | 209 | 43 | 4.9 |
| 1 | 52.47 | 340 | 2.5 | 2.1 | 0.7 | 637 | 126 | 83 | 33 | 493 | 235 | 206 | 45 | 4.6 |
| 3 | 52.65 | 340 | 2.55 | 2.1 | 0.7 | 642 | 126 | 84 | 33 | 493 | 235 | 207 | 44 | 4.7 |
| 10 | 52.78 | 340 | 2.92 | 2.1 | 0.7 | 654 | 124 | 90 | 31 | 493 | 235 | 211 | 42 | 5.1 |
| 2 | 53.07 | 340 | 2.5 | 2.1 | 0.7 | 650 | 126 | 84 | 34 | 493 | 235 | 207 | 45 | 4.6 |
| 11 | 52.08 | 340 | 2.98 | 2.1 | 0.7 | 642 | 123 | 90 | 30 | 493 | 235 | 211 | 41 | 5.2 |

Example 4

Chemometric analysis and validation of the analysis was carried out on a variety of polymer samples. Additionally the results of the chemometric analysis allowed for the digital generation of samples having a variety of molecular weight distributions in order to assess parameters significant to the melt fracture characteristics investigated. Data relating to these analyses carried out using the methodologies disclosed herein for polyethylene resins are presented in Data sets A-X.

Without further elaboration, it is believed that one skilled in the art can, using the description herein, utilize the present invention to its fullest extent. While aspects of the invention have been shown and described, modifications thereof can be made by one skilled in the art without departing from the spirit and teachings of the invention. The aspects and examples described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

The invention claimed is:

1. A method of preparing a medium-density polyethylene pipe comprising: melting a multimodal metallocene-catalyzed polyethylene resin to form a molten polyethylene, wherein the multimodal metallocene-catalyzed polyethylene resin has a density of from about 0.925 g/ml to about 0.942 g/ml, a magnitude of slip-stick greater than about 300 psi, a stress for smooth to matte transition of greater than about 90 kPa of stress, and a shear rate for smooth to matte transition greater than about $10\,s^{-1}$, wherein the magnitude of slip-stick, stress for smooth to matte transition, and shear rate for smooth to matte transition are determined by a capillary rheology test; and forming the molten polyethylene resin into pipe.

2. The method of claim 1 wherein the polyethylene resin has a density of from about 0.928 g/ml to about 0.940 g/ml.

3. The method of claim 1 wherein the polyethylene resin has a melt flow rate of less than about 0.4 g/10 min.

4. The method of claim 1 wherein the pipe has a PENT value of from about 500 hours to about 20,000 hours.

5. The method of claim 1 wherein the pipe has a Charpy $T_{db}$ of less than about −25° C.

6. The method of claim 1 wherein the pipe has a Charpy impact energy of from about 1.0 J to about 3.0 J.

7. The method of claim 1 wherein the pipe has a flexural modulus, 2% secant of from about 80 kpsi to about 110 kpsi.

8. The method of claim 1 wherein the pipe has an elongation at break of greater than about 450%.

9. The method of claim 1 wherein the pipe has a Young's modulus of from about 120 kpsi to about 190 kpsi.

10. The method of claim 1 wherein the pipe has a tensile strength at yield of from about 2600 psi to less than about 3,000 psi.

11. The method of claim 1 wherein the pipe has a tensile strength at break of greater than about 3000 psi.

12. The method of claim 1 wherein the pipe has a thermal stability of greater than about 220° C.

13. The method of claim 1 wherein the pipe has a critical temperature value ($T_c$) of equal to or less than about 0° C.

14. The method of claim 1 wherein the pipe has a critical pressure value ($P_c$) of greater than about 12 bar.

15. The method of claim 1 wherein the pipe has a tensile natural draw ratio of less than about 500%.

16. The method of claim 1 wherein the pipe has a hydrostatic design basis at 23° C. of from about 1200 psi to less than about 1530 psi and at 60° C. of from about 960 psi to less than about 1200 psi.

17. The method of claim 1 wherein the pipe has a minimum required strength of from about 8≤σLPL<10 MPa.

18. A pipe prepared from a multimodal metallocene-catalyzed polyethylene resin having a density of from about 0.925 g/ml to about 0.942 g/ml, a magnitude of slip-stick greater than about 300 psi; a stress for smooth to matte transition of greater than about 90 kPa, and a shear rate for smooth to matte transition greater than about 10 s$^{-1}$, wherein the magnitude of slip-stick, stress for smooth to matte transition, and shear rate for smooth to matte transition are determined by a capillary rheology test.

19. The pipe of claim 18 having a PENT value of from about 500 hours to about 20,000 hours.

20. The pipe of claim 18 having a Charpy $T_{db}$ of less than about −25° C.

\* \* \* \* \*